US010994120B2

(12) United States Patent
Tuval et al.

(10) Patent No.: US 10,994,120 B2
(45) Date of Patent: May 4, 2021

(54) VENTRICULAR ASSIST DEVICE

(71) Applicant: Magenta Medical Ltd., Kadima (IL)

(72) Inventors: Yosi Tuval, Even Yehuda (IL); Zev Sohn, Karnei Shomron (IL); Ehud Schwammenthal, Ra'anana (IL); Gad Lubinsky, Ein Vered (IL)

(73) Assignee: MAGENTA MEDICAL LTD., Kadima (IL)

( * ) Notice: Subject to any disclaimer, the term of this patent is extended or adjusted under 35 U.S.C. 154(b) by 38 days.

(21) Appl. No.: 16/281,237

(22) Filed: Feb. 21, 2019

(65) Prior Publication Data

US 2019/0209753 A1    Jul. 11, 2019

Related U.S. Application Data

(63) Continuation of application No. PCT/IB2019/050186, filed on Jan. 10, 2019.
(Continued)

(51) Int. Cl.
*A61M 60/422* (2021.01)
*A61B 5/0215* (2006.01)
(Continued)

(52) U.S. Cl.
CPC ......... *A61M 60/422* (2021.01); *A61B 5/0215* (2013.01); *A61B 5/283* (2021.01);
(Continued)

(58) Field of Classification Search
CPC .............. A61M 1/1031; A61M 1/1098; A61M 1/1024; A61M 1/1012; A61M 1/1017;
(Continued)

(56) References Cited

U.S. PATENT DOCUMENTS

| 4,625,712 A | 12/1986 | Wampler |
| 4,753,221 A | 6/1988 | Kensey et al. |

(Continued)

FOREIGN PATENT DOCUMENTS

| AU | 2013205145 A1 | 5/2013 |
| EP | 0916359 A1 | 5/1999 |

(Continued)

OTHER PUBLICATIONS

Extended European Search Report for European Application No. 19172327.9 dated Aug. 23, 2019.
(Continued)

*Primary Examiner* — Gary Jackson
*Assistant Examiner* — Sebastian X Lukjan
(74) *Attorney, Agent, or Firm* — Dorsey & Whitney LLP

(57) ABSTRACT

Apparatus and methods are described including placing an impeller of a ventricular assist device inside a left ventricle of a subject, with a frame disposed around the impeller. The impeller is driven to pump blood from the left ventricle to an aorta of the subject, by rotating the impeller. The impeller is placed inside the left ventricle such that the impeller is allowed to undergo axial motion with respect to the frame, in response to cyclical changes in a pressure difference between the left ventricle and the aorta. Other applications are also described.

32 Claims, 41 Drawing Sheets

Related U.S. Application Data

(60) Provisional application No. 62/615,538, filed on Jan. 10, 2018, provisional application No. 62/665,718, filed on May 2, 2018, provisional application No. 62/681,868, filed on Jun. 7, 2018, provisional application No. 62/727,605, filed on Sep. 6, 2018.

(51) Int. Cl.
| | |
|---|---|
| *F04D 3/02* | (2006.01) |
| *F04D 15/00* | (2006.01) |
| *F04D 29/041* | (2006.01) |
| *F04D 29/042* | (2006.01) |
| *F04D 25/02* | (2006.01) |
| *F04D 29/18* | (2006.01) |
| *F04D 29/24* | (2006.01) |
| *F04D 7/00* | (2006.01) |
| *A61B 5/283* | (2021.01) |
| *A61M 60/40* | (2021.01) |
| *A61M 60/50* | (2021.01) |
| *A61M 60/135* | (2021.01) |
| *A61M 60/148* | (2021.01) |
| *A61M 60/205* | (2021.01) |
| *A61M 60/414* | (2021.01) |
| *A61M 60/419* | (2021.01) |
| *A61M 60/818* | (2021.01) |
| *A61M 60/824* | (2021.01) |
| *A61M 60/829* | (2021.01) |
| *A61M 60/833* | (2021.01) |
| *A61M 60/857* | (2021.01) |
| *A61M 60/896* | (2021.01) |

(52) U.S. Cl.
CPC ........ *A61M 60/135* (2021.01); *A61M 60/148* (2021.01); *A61M 60/205* (2021.01); *A61M 60/40* (2021.01); *A61M 60/414* (2021.01); *A61M 60/419* (2021.01); *A61M 60/50* (2021.01); *A61M 60/818* (2021.01); *A61M 60/824* (2021.01); *A61M 60/829* (2021.01); *A61M 60/833* (2021.01); *A61M 60/857* (2021.01); *A61M 60/896* (2021.01); *F04D 3/02* (2013.01); *F04D 7/00* (2013.01); *F04D 15/0066* (2013.01); *F04D 25/02* (2013.01); *F04D 29/041* (2013.01); *F04D 29/042* (2013.01); *F04D 29/181* (2013.01); *F04D 29/247* (2013.01); *A61M 2205/0266* (2013.01); *A61M 2205/3317* (2013.01); *A61M 2205/3327* (2013.01); *A61M 2205/3334* (2013.01); *A61M 2205/3344* (2013.01); *A61M 2205/3365* (2013.01); *A61M 2205/50* (2013.01); *A61M 2230/04* (2013.01); *A61M 2230/30* (2013.01)

(58) Field of Classification Search
CPC .. A61M 1/1008; A61M 1/125; A61M 1/1018; A61M 1/1029; A61M 1/1013; A61M 1/122; A61M 1/1086; A61M 1/1034; A61M 1/1036; A61M 1/102; A61M 2205/3334; A61M 2205/0266; A61M 2205/3344; A61M 2230/04; A61M 2205/3365; A61M 2230/30; A61M 2205/3317; A61M 2205/50; A61M 2205/3317; F04D 29/181; F04D 29/247; F04D 7/00; F04D 3/02; F04D 15/0066; F04D 29/041; F04D 29/042; F04D 25/02; A61B 5/0215; A61B 5/042

See application file for complete search history.

(56) References Cited

U.S. PATENT DOCUMENTS

| | | |
|---|---|---|
| 4,919,647 A | 4/1990 | Nash |
| 4,954,055 A | 9/1990 | Raible et al. |
| 4,969,865 A | 11/1990 | Hwang et al. |
| 4,985,014 A | 1/1991 | Orejola |
| 5,011,469 A | 4/1991 | Buckberg et al. |
| 5,061,256 A | 10/1991 | Wampler |
| 5,169,378 A | 12/1992 | Figuera |
| 5,275,580 A | 1/1994 | Yamazaki |
| 5,531,789 A | 7/1996 | Yamazaki et al. |
| 5,569,275 A | 10/1996 | Kotula et al. |
| 5,613,935 A | 3/1997 | Jarvik |
| 5,692,882 A | 12/1997 | Bozeman, Jr. et al. |
| 5,713,730 A | 2/1998 | Nose et al. |
| 5,749,855 A | 5/1998 | Reitan |
| 5,772,693 A | 6/1998 | Brownlee |
| 5,843,158 A | 12/1998 | Lenker et al. |
| 5,863,179 A | 1/1999 | Westphal et al. |
| 5,876,385 A | 3/1999 | Ikari et al. |
| 5,911,685 A | 6/1999 | Siess et al. |
| 5,928,132 A | 7/1999 | Leschinsky |
| 5,947,892 A | 9/1999 | Benkowski et al. |
| 5,964,694 A | 10/1999 | Siess et al. |
| 6,007,478 A | 12/1999 | Siess et al. |
| 6,086,527 A | 7/2000 | Talpade |
| 6,116,862 A | 9/2000 | Rau et al. |
| 6,135,729 A | 10/2000 | Aber |
| 6,162,017 A | 12/2000 | Raible |
| 6,217,541 B1 | 4/2001 | Yu |
| 6,247,892 B1 | 6/2001 | Kazatchkov et al. |
| 6,355,001 B1 | 3/2002 | Quinn et al. |
| 6,413,222 B1 | 7/2002 | Pantages et al. |
| 6,482,228 B1 | 11/2002 | Norred |
| 6,506,146 B1 | 1/2003 | Mohl |
| 6,533,716 B1 | 3/2003 | Schmutz-Rode et al. |
| 6,537,315 B2 | 3/2003 | Yamazaki et al. |
| 6,544,216 B1 | 4/2003 | Sammler et al. |
| 6,592,567 B1 | 7/2003 | Levin et al. |
| 6,616,624 B1 | 9/2003 | Kieval |
| 6,884,210 B2 | 4/2005 | Nose et al. |
| 6,949,066 B2 | 9/2005 | Bearnson et al. |
| 7,004,925 B2 | 2/2006 | Navia et al. |
| 7,010,954 B2 | 3/2006 | Siess et al. |
| 7,022,100 B1 | 4/2006 | Aboul-hosn et al. |
| 7,027,875 B2 | 4/2006 | Siess et al. |
| 7,144,364 B2 | 12/2006 | Barbut et al. |
| 7,159,593 B2 | 1/2007 | Mccarthy et al. |
| 7,258,679 B2 | 8/2007 | Moore et al. |
| 7,335,192 B2 | 2/2008 | Keren et al. |
| 7,338,521 B2 | 3/2008 | Antaki et al. |
| 7,341,570 B2 | 3/2008 | Keren et al. |
| 7,393,181 B2 | 7/2008 | Mcbride et al. |
| 7,485,104 B2 | 2/2009 | Kieval |
| 7,717,952 B2 | 5/2010 | Case et al. |
| 7,744,642 B2 | 6/2010 | Rittgers et al. |
| 7,762,941 B2 | 7/2010 | Jarvik |
| 7,766,892 B2 | 8/2010 | Keren et al. |
| 7,766,961 B2 | 8/2010 | Patel et al. |
| 7,780,628 B1 | 8/2010 | Keren et al. |
| 7,811,221 B2 | 10/2010 | Gross |
| 7,841,976 B2 | 11/2010 | McBride et al. |
| 7,914,436 B1 | 3/2011 | Kung |
| 7,914,503 B2 | 3/2011 | Goodson et al. |
| 8,012,121 B2 | 9/2011 | Goodson et al. |
| 8,079,948 B2 | 12/2011 | Shifflette |
| 8,118,723 B2 | 2/2012 | Richardson et al. |
| 8,123,669 B2 | 2/2012 | Siess et al. |
| 8,157,758 B2 | 4/2012 | Pecor et al. |
| 8,192,451 B2 | 6/2012 | Cambronne et al. |
| 8,216,122 B2 | 7/2012 | Kung |
| 8,221,492 B2 | 7/2012 | Case et al. |
| 8,235,933 B2 | 8/2012 | Keren et al. |
| 8,277,470 B2 | 10/2012 | Demarais et al. |
| 8,376,707 B2 | 2/2013 | Mcbride et al. |
| 8,439,859 B2 | 5/2013 | Pfeffer et al. |
| 8,449,443 B2 | 5/2013 | Rodefeld et al. |

(56) References Cited

U.S. PATENT DOCUMENTS

| | | |
|---|---|---|
| 8,485,961 B2 | 7/2013 | Campbell et al. |
| 8,489,190 B2 | 7/2013 | Pfeffer et al. |
| 8,512,262 B2 | 8/2013 | Gertner |
| 8,535,211 B2 | 9/2013 | Walters et al. |
| 8,538,535 B2 | 9/2013 | Ariav et al. |
| 8,579,858 B2 | 11/2013 | Reitan et al. |
| 8,591,393 B2 | 11/2013 | Walters et al. |
| 8,591,539 B2 | 11/2013 | Gellman |
| 8,597,170 B2 | 12/2013 | Walters et al. |
| 8,617,239 B2 | 12/2013 | Reitan |
| 8,672,868 B2 | 3/2014 | Simons |
| 8,721,517 B2 | 5/2014 | Zeng et al. |
| 8,734,331 B2 | 5/2014 | Evans et al. |
| 8,734,508 B2 | 5/2014 | Hastings et al. |
| 8,777,832 B1 | 7/2014 | Wang et al. |
| 8,814,543 B2 | 8/2014 | Liebing |
| 8,814,776 B2 | 8/2014 | Hastie et al. |
| 8,814,933 B2 | 8/2014 | Siess |
| 8,827,887 B2 | 9/2014 | Curtis et al. |
| 8,849,398 B2 | 9/2014 | Evans |
| 8,864,642 B2 | 10/2014 | Scheckel |
| 8,888,728 B2 | 11/2014 | Aboul-hosn et al. |
| 8,900,060 B2 | 12/2014 | Liebing |
| 8,926,492 B2 | 1/2015 | Scheckel |
| 8,932,141 B2 | 1/2015 | Liebing |
| 8,944,748 B2 | 2/2015 | Liebing |
| 8,979,493 B2 | 3/2015 | Roehn |
| 8,998,792 B2 | 4/2015 | Scheckel |
| 9,028,216 B2 | 5/2015 | Schumacher et al. |
| 9,072,825 B2 | 7/2015 | Pfeffer et al. |
| 9,138,518 B2 | 9/2015 | Campbell et al. |
| 9,162,017 B2 | 10/2015 | Evans et al. |
| 9,259,521 B2 | 2/2016 | Simons |
| 9,278,189 B2 | 3/2016 | Corbett |
| 9,314,558 B2 | 4/2016 | Er |
| 9,328,741 B2 | 5/2016 | Liebing |
| 9,358,329 B2 | 6/2016 | Fitzgerald et al. |
| 9,358,330 B2 | 6/2016 | Schumacher |
| 9,364,592 B2 | 6/2016 | Mcbride et al. |
| 9,364,593 B2 | 6/2016 | Mcbride et al. |
| 9,370,613 B2 | 6/2016 | Hsu et al. |
| 9,381,288 B2 | 7/2016 | Schenck et al. |
| 9,404,505 B2 | 8/2016 | Scheckel |
| 9,416,791 B2 | 8/2016 | Toellner |
| 9,421,311 B2 | 8/2016 | Tanner et al. |
| 9,446,179 B2 | 9/2016 | Keenan et al. |
| 9,474,840 B2 | 10/2016 | Siess |
| 9,512,839 B2 | 12/2016 | Liebing |
| 9,533,082 B2 | 1/2017 | Reichenbach et al. |
| 9,533,084 B2 | 1/2017 | Siess et al. |
| 9,545,468 B2 | 1/2017 | Aboul-hosn et al. |
| 9,550,017 B2 | 1/2017 | Spanier et al. |
| 9,561,314 B2 | 2/2017 | Aboul-hosn et al. |
| 9,597,205 B2 | 3/2017 | Tuval |
| 9,597,437 B2 | 3/2017 | Aboul-hosn et al. |
| 9,603,983 B2 | 3/2017 | Roehn et al. |
| 9,611,743 B2 | 4/2017 | Toellner et al. |
| 9,616,159 B2 | 4/2017 | Anderson et al. |
| 9,623,161 B2 | 4/2017 | Medvedev et al. |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,713,663 B2 | 7/2017 | Medvedev et al. |
| 9,717,833 B2 | 8/2017 | Mcbride et al. |
| 9,759,237 B2 | 9/2017 | Liebing |
| 9,764,113 B2 | 9/2017 | Tuval et al. |
| 9,789,238 B2 | 10/2017 | Aboul-hosn et al. |
| 9,795,727 B2 | 10/2017 | Schumacher |
| 9,814,814 B2 | 11/2017 | Corbett et al. |
| 9,821,146 B2 | 11/2017 | Tao et al. |
| 9,827,356 B2 | 11/2017 | Muller et al. |
| 9,833,550 B2 | 12/2017 | Siess |
| 9,835,550 B2 | 12/2017 | Kakuno et al. |
| 9,850,906 B2 | 12/2017 | Ozaki et al. |
| 9,872,947 B2 | 1/2018 | Keenan et al. |
| 9,872,948 B2 | 1/2018 | Siess |
| 9,878,079 B2 | 1/2018 | Pfeffer et al. |
| 9,889,242 B2 | 2/2018 | Pfeffer et al. |
| 9,907,890 B2 | 3/2018 | Muller |
| 9,919,087 B2 | 3/2018 | Pfeffer et al. |
| 9,962,475 B2 | 5/2018 | Campbell et al. |
| 9,974,893 B2 | 5/2018 | Toellner |
| 9,999,714 B2 | 6/2018 | Spanier et al. |
| 10,029,037 B2 | 7/2018 | Muller et al. |
| 10,029,040 B2 | 7/2018 | Taskin |
| 10,039,872 B2 | 8/2018 | Zeng et al. |
| 10,039,874 B2 | 8/2018 | Schwammenthal et al. |
| 10,052,420 B2 | 8/2018 | Medvedev et al. |
| 10,071,192 B2 | 9/2018 | Zeng |
| 10,086,121 B2 | 10/2018 | Fitzgerald et al. |
| 10,105,475 B2 | 10/2018 | Muller |
| 10,117,980 B2 | 11/2018 | Keenan et al. |
| 10,119,550 B2 | 11/2018 | Bredenbreuker et al. |
| 10,149,932 B2 | 12/2018 | Mcbride et al. |
| 10,183,104 B2 | 1/2019 | Anderson et al. |
| 10,221,866 B2 | 3/2019 | Liebing |
| 10,238,783 B2 | 3/2019 | Aboul-hosn et al. |
| 10,265,447 B2 | 4/2019 | Campbell et al. |
| 10,265,448 B2 | 4/2019 | Liebing |
| 10,279,095 B2 | 5/2019 | Aboul-hosn et al. |
| 10,300,185 B2 | 5/2019 | Aboul-hosn et al. |
| 10,300,186 B2 | 5/2019 | Aboul-hosn et al. |
| 10,316,853 B2 | 6/2019 | Toellner |
| 10,330,101 B2 | 6/2019 | Toellner |
| 10,363,349 B2 | 7/2019 | Muller et al. |
| 10,369,260 B2 | 8/2019 | Smith et al. |
| 10,376,162 B2 | 8/2019 | Edelman et al. |
| 10,449,276 B2 | 10/2019 | Pfeffer et al. |
| 10,449,279 B2 | 10/2019 | Muller |
| 2001/0041934 A1 | 11/2001 | Yamazaki et al. |
| 2002/0151799 A1 | 10/2002 | Pantages et al. |
| 2003/0055486 A1 | 3/2003 | Adams et al. |
| 2004/0064090 A1 | 4/2004 | Keren et al. |
| 2004/0064091 A1 | 4/2004 | Keren et al. |
| 2004/0116769 A1 | 6/2004 | Jassawalla et al. |
| 2004/0167415 A1 | 8/2004 | Gelfand et al. |
| 2004/0210236 A1 | 10/2004 | Allers et al. |
| 2004/0260389 A1 | 12/2004 | Case et al. |
| 2005/0033406 A1 | 2/2005 | Barnhart et al. |
| 2005/0049692 A1 | 3/2005 | Numamoto et al. |
| 2005/0079274 A1 | 4/2005 | Palasis et al. |
| 2005/0085848 A1 | 4/2005 | Johnson et al. |
| 2005/0180854 A1 | 8/2005 | Grabau et al. |
| 2006/0106449 A1 | 5/2006 | Ben |
| 2006/0265051 A1 | 11/2006 | Caro et al. |
| 2007/0100415 A1 | 5/2007 | Licata et al. |
| 2007/0100435 A1 | 5/2007 | Case et al. |
| 2007/0142729 A1 | 6/2007 | Pfeiffer et al. |
| 2007/0162103 A1 | 7/2007 | Case et al. |
| 2007/0208291 A1 | 9/2007 | Patel |
| 2007/0260327 A1 | 11/2007 | Case et al. |
| 2008/0009668 A1 | 1/2008 | Cohn |
| 2008/0103591 A1 | 5/2008 | Siess |
| 2008/0132747 A1 | 6/2008 | Shifflette |
| 2008/0132748 A1 | 6/2008 | Shifflette |
| 2008/0140189 A1 | 6/2008 | Nguyen et al. |
| 2008/0154236 A1 | 6/2008 | Elkins et al. |
| 2008/0183280 A1 | 7/2008 | Agnew et al. |
| 2008/0306327 A1 | 12/2008 | Shifflette |
| 2009/0024195 A1 | 1/2009 | Rezai et al. |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2009/0264991 A1 | 10/2009 | Paul et al. |
| 2009/0287299 A1 | 11/2009 | Tabor et al. |
| 2009/0318857 A1 | 12/2009 | Goodson et al. |
| 2010/0130810 A1 | 5/2010 | Mohl |
| 2010/0268017 A1 | 10/2010 | Siess |
| 2011/0004046 A1 | 1/2011 | Campbell et al. |
| 2011/0034874 A1 | 2/2011 | Reitan et al. |
| 2011/0106244 A1 | 5/2011 | Ferrari et al. |
| 2011/0152999 A1 | 6/2011 | Hastings et al. |
| 2011/0190874 A1 | 8/2011 | Celermajer et al. |
| 2011/0213408 A1 | 9/2011 | Gross et al. |

(56) References Cited

U.S. PATENT DOCUMENTS

| | | |
|---|---|---|
| 2011/0230949 A1 | 9/2011 | Haverkost et al. |
| 2011/0257462 A1 | 10/2011 | Rodefeld et al. |
| 2011/0264075 A1 | 10/2011 | Leung et al. |
| 2011/0282128 A1 | 11/2011 | Reitan et al. |
| 2011/0301662 A1 | 12/2011 | Bar-yoseph et al. |
| 2012/0022579 A1 | 1/2012 | Fulton |
| 2012/0059460 A1 | 3/2012 | Reitan |
| 2012/0089047 A1 | 4/2012 | Ryba et al. |
| 2012/0116382 A1 | 5/2012 | Ku et al. |
| 2012/0130469 A1 | 5/2012 | Cragg et al. |
| 2012/0143141 A1 | 6/2012 | Verkaik et al. |
| 2012/0178986 A1 | 7/2012 | Campbell et al. |
| 2012/0224970 A1 | 9/2012 | Schumacher et al. |
| 2012/0234411 A1 | 9/2012 | Scheckel |
| 2012/0237357 A1 | 9/2012 | Schumacher et al. |
| 2012/0245680 A1* | 9/2012 | Masuzawa .......... A61M 1/1086 623/3.11 |
| 2012/0303112 A1 | 11/2012 | Armstrong et al. |
| 2012/0316586 A1 | 12/2012 | Demarais et al. |
| 2012/0328460 A1 | 12/2012 | Horvath et al. |
| 2013/0053623 A1* | 2/2013 | Evans ................ A61M 1/101 600/16 |
| 2013/0053732 A1 | 2/2013 | Heuser |
| 2013/0060077 A1 | 3/2013 | Liebing |
| 2013/0085319 A1 | 4/2013 | Evans et al. |
| 2013/0177409 A1 | 7/2013 | Schumacher et al. |
| 2013/0177432 A1 | 7/2013 | Toellner et al. |
| 2014/0018840 A1 | 1/2014 | Morgan et al. |
| 2014/0025041 A1 | 1/2014 | Fukuoka et al. |
| 2014/0128659 A1 | 5/2014 | Heuring et al. |
| 2014/0255176 A1 | 9/2014 | Bredenbreuker et al. |
| 2014/0275720 A1 | 9/2014 | Ferrari |
| 2014/0275722 A1 | 9/2014 | Zimmermann et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0258262 A1 | 9/2015 | Pfeffer et al. |
| 2015/0343136 A1 | 12/2015 | Nitzan et al. |
| 2015/0343179 A1 | 12/2015 | Schumacher et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |
| 2016/0106896 A1 | 4/2016 | Pfeffer et al. |
| 2016/0129170 A1 | 5/2016 | Siess |
| 2016/0136341 A1 | 5/2016 | Pfeffer et al. |
| 2016/0136342 A1 | 5/2016 | Pfeffer et al. |
| 2016/0144089 A1 | 5/2016 | Woo et al. |
| 2016/0256620 A1 | 9/2016 | Scheckel et al. |
| 2016/0279310 A1 | 9/2016 | Scheckel et al. |
| 2017/0014562 A1 | 1/2017 | Liebing |
| 2017/0028115 A1 | 2/2017 | Muller |
| 2017/0035954 A1 | 2/2017 | Muller et al. |
| 2017/0087286 A1 | 3/2017 | Spanier et al. |
| 2017/0087288 A1 | 3/2017 | Groß-hardt et al. |
| 2017/0100527 A1 | 4/2017 | Schwammenthal et al. |
| 2017/0173237 A1 | 6/2017 | Pfeifer et al. |
| 2017/0215918 A1 | 8/2017 | Tao et al. |
| 2017/0232168 A1 | 8/2017 | Reichenbach et al. |
| 2017/0333067 A1 | 11/2017 | Wilson |
| 2017/0333607 A1 | 11/2017 | Zarins |
| 2017/0340791 A1 | 11/2017 | Aboul-hosn et al. |
| 2017/0348470 A1 | 12/2017 | D'ambrosio et al. |
| 2018/0050142 A1 | 2/2018 | Siess et al. |
| 2018/0055979 A1 | 3/2018 | Corbett et al. |
| 2018/0064861 A1 | 3/2018 | Dur et al. |
| 2018/0080326 A1 | 3/2018 | Schumacher et al. |
| 2018/0100507 A1 | 4/2018 | Wu et al. |
| 2018/0104453 A1 | 4/2018 | Tao et al. |
| 2018/0149164 A1 | 5/2018 | Siess |
| 2018/0149165 A1 | 5/2018 | Siess et al. |
| 2018/0169312 A1 | 6/2018 | Barry |
| 2018/0169313 A1 | 6/2018 | Schwammenthal et al. |
| 2018/0207334 A1 | 7/2018 | Siess |
| 2018/0228952 A1 | 8/2018 | Pfeffer et al. |
| 2018/0228953 A1 | 8/2018 | Siess et al. |
| 2018/0264182 A1 | 9/2018 | Spanier et al. |
| 2018/0264183 A1 | 9/2018 | Jahangir |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0303992 A1 | 10/2018 | Taskin |
| 2018/0353667 A1 | 12/2018 | Moyer et al. |
| 2019/0015570 A1 | 1/2019 | Muller |
| 2019/0030228 A1 | 1/2019 | Keenan et al. |
| 2019/0046702 A1 | 2/2019 | Siess et al. |
| 2019/0060539 A1 | 2/2019 | Siess et al. |
| 2019/0070345 A1 | 3/2019 | Mcbride et al. |
| 2019/0076167 A1 | 3/2019 | Fantuzzi et al. |
| 2019/0083690 A1 | 3/2019 | Siess et al. |
| 2019/0101130 A1 | 4/2019 | Bredenbreuker et al. |
| 2019/0117865 A1 | 4/2019 | Walters et al. |
| 2019/0134287 A1 | 5/2019 | Demou |
| 2019/0143018 A1 | 5/2019 | Salahieh et al. |
| 2019/0143019 A1 | 5/2019 | Mehaffey et al. |
| 2019/0170153 A1 | 6/2019 | Scheckel |
| 2019/0175803 A1 | 6/2019 | Pfeffer et al. |
| 2019/0175806 A1 | 6/2019 | Tuval et al. |
| 2019/0209755 A1 | 7/2019 | Nix et al. |
| 2019/0209758 A1 | 7/2019 | Tuval et al. |
| 2019/0216994 A1 | 7/2019 | Pfeffer et al. |
| 2019/0224391 A1 | 7/2019 | Liebing |
| 2019/0224392 A1 | 7/2019 | Pfeffer et al. |
| 2019/0224393 A1 | 7/2019 | Pfeffer et al. |
| 2019/0239998 A1 | 8/2019 | Tuval et al. |
| 2019/0262518 A1 | 8/2019 | Molteni et al. |
| 2019/0269840 A1 | 9/2019 | Tuval et al. |
| 2019/0282741 A1 | 9/2019 | Franano et al. |
| 2019/0290817 A1 | 9/2019 | Guo et al. |
| 2019/0321527 A1 | 10/2019 | King et al. |
| 2019/0321530 A1 | 10/2019 | Cambronne et al. |
| 2019/0321531 A1 | 10/2019 | Cambronne et al. |
| 2019/0328948 A1 | 10/2019 | Salahieh et al. |
| 2019/0336664 A1 | 11/2019 | Liebing |
| 2019/0344001 A1 | 11/2019 | Salahieh et al. |
| 2019/0351118 A1 | 11/2019 | Graichen et al. |
| 2020/0038567 A1 | 2/2020 | Siess et al. |

FOREIGN PATENT DOCUMENTS

| | | |
|---|---|---|
| EP | 2040639 B1 | 2/2014 |
| EP | 2662099 B1 | 9/2014 |
| EP | 2427230 B1 | 12/2014 |
| EP | 2396050 B1 | 1/2015 |
| EP | 3115070 A1 | 1/2017 |
| EP | 3205360 B1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| GB | 2451161 A | 1/2009 |
| JP | 2012505038 A | 3/2012 |
| WO | 9001972 A1 | 3/1990 |
| WO | 90/13321 | 11/1990 |
| WO | 1994/01148 A1 | 1/1994 |
| WO | 99/34847 | 7/1999 |
| WO | 2001/083016 A2 | 5/2000 |
| WO | 2000043053 A1 | 7/2000 |
| WO | 0062838 A2 | 10/2000 |
| WO | 2002/070039 A2 | 3/2001 |
| WO | 2002/038085 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007081818 A2 | 7/2007 |
| WO | 2008005990 A2 | 1/2008 |
| WO | 2008055301 A1 | 5/2008 |
| WO | 2008104858 A2 | 9/2008 |
| WO | 2009010963 A2 | 1/2009 |
| WO | 2009046096 A1 | 4/2009 |
| WO | 2009129481 A1 | 10/2009 |

(56) References Cited

FOREIGN PATENT DOCUMENTS

| WO | 2010042546 | | 4/2010 |
|---|---|---|---|
| WO | 2010063494 | A1 | 6/2010 |
| WO | 2010127871 | A1 | 11/2010 |
| WO | 2011035926 | A1 | 3/2011 |
| WO | 2011076441 | A1 | 6/2011 |
| WO | 2012007141 | A1 | 1/2012 |
| WO | 2013032849 | A1 | 3/2013 |
| WO | 2013070186 | A1 | 5/2013 |
| WO | 2013093001 | A2 | 6/2013 |
| WO | 2013148697 | A1 | 10/2013 |
| WO | 2013183060 | A2 | 12/2013 |
| WO | 2014141284 | A2 | 9/2014 |
| WO | 2015063277 | A2 | 5/2015 |
| WO | 2015160943 | A1 | 10/2015 |
| WO | 2015177793 | A2 | 11/2015 |
| WO | 2016001218 | A1 | 1/2016 |
| WO | 2016005803 | A2 | 1/2016 |
| WO | 2016185473 | A1 | 11/2016 |
| WO | 2016207293 | A1 | 12/2016 |
| WO | 2017060254 | A1 | 4/2017 |
| WO | 2017137604 | A1 | 8/2017 |
| WO | 2017147291 | A1 | 8/2017 |
| WO | 2018061002 | A1 | 4/2018 |
| WO | 2018067410 | A1 | 4/2018 |
| WO | 2018078615 | A1 | 5/2018 |
| WO | 2018096531 | A1 | 5/2018 |
| WO | 2018226991 | A1 | 12/2018 |
| WO | 2018234454 | A1 | 12/2018 |
| WO | 2019094963 | A1 | 5/2019 |
| WO | 2019138350 | A2 | 7/2019 |
| WO | 2019152875 | A1 | 8/2019 |
| WO | 2020152611 | A2 | 7/2020 |

OTHER PUBLICATIONS

International Search Report and Written Opinion from International Application No. PT/IB2019/050186 dated Jul. 18, 2019.
Rodefeld, "Cavopulmonary assist for the univentricular Fontan circulation: von Karman viscous impeller pump", The Journal of Thoracic and Cardiovascular Surgery, vol. 140, No. 3, 2010, pp. 529-536.
Sianos, et al., "The Recover® LP 2.5 catheter-mounted left ventricular assist device", EuroIntervention, EuroPCROnline.com, 2006, pp. 116-119.
Throckmorton, et al., "Mechanical Cavopulmonary Assist for the Univentricular Fontan Circulation Using a Novel Folding Propeller Blood Pump", ASAIO Journal, 2007, pp. 734-741.
US 9,427,207, 7/2004, ABIOMED EUROPE GMBH (withdrawn)
US 9,399,088, 4/2013, ABIOMED EUROPE GMBH (withdrawn)
International Search Report and Written Opinion from International Application No. PCT/IL2017/051158 dated Jan. 17, 2018.
U.S. Appl. No. 14/567,439, filed Dec. 11, 2014.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,482, filed Feb. 18, 2019.
U.S. Appl. No. 16/279,352, filed Feb. 19, 2019.
U.S. Appl. No. 16/280,566, filed Feb. 20, 2019.
U.S. Appl. No. 16/281,264, filed Feb. 21, 2019.
U.S. Appl. No. 61/656,244, filed Jun. 6, 2012.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,718, filed May 2, 2018.
U.S. Appl. No. 62/681,868, filed Jun. 7, 2018.
U.S. Appl. No. 62/727,605, filed Sep. 6, 2018.
"Tanslation of decision of Board 4 (Nullity Board) of the German Federal Patent Court re German patent 10336902", pronounced Nov. 15, 2016, and appendices to decision, 62 pages.
Agarwal, et al., "Newer-generation ventricular assist devices.", Best Practice & Research Clinical Anaesthesiology, 26.2, 2012, pp. 117-130.
Alba, et al., "The future is here: ventricular assist devices for the failing heart", Expert review of cardiovascular therapy, 7.9, 2009, pp. 1067-1077.
Burnett, et al., "Renal Interstitial Pressure and Sodium Excretion During Renal Vein Constriction", American Physiological Society, 1980, pp. F279-F282.
Cassidy, et al., "The Conductance Volume Catheter Technique for Measurement of Left Ventricular Volume in Young Piglets", Pediatric Research, Val. 31, No. 1, 1992, pp. 85-90.
Coxworth, , "Artificial Vein Valve Could Replace Drugs for Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion and the Association With Renal Impairment in Patients With Cardiac Dysfunction", European Journal of Heart Failure, vol. 9, 2007, pp. 872-878.
Damman, et al., "Increased Central Venous Pressure is Associated With Impaired Renal Function and Mortality in a Broad Spectrum of Patients With Cardiovascular Disease", Journal of American College of Cardiology, vol. 53, 2009, pp. 582-588.
Doty, et al., "The Effect of Increased Renal Venous Pressure on Renal Function", The Journal of Trauma,, vol. 47(6), Dec. 1999, pp. 1000-1003.
Felker, et al., "Anemia as a Risk Factor and Therapeutic Target in Heart Failure", Journal of the American College of Cardiology, vol. 44, 2004, pp. 959-966.
Firth, et al., "Raised Venous Pressure: A Direct Cause of Sodium Retention in Oedema?", The Lancet, May 7, 1988, pp. 1033-1036.
Forman, et al., "Incidence, Predictors at Admission, and Impact of Worsening Renal Function Among Patients Hospitalized With Heart Failure", Journal of American College of Cardiology, vol. 43, 2004, pp. 61-67.
Fraser, et al., "The use of computational fluid dynamics in the development of ventricular assist devices", Medical engineering & physics, 33.3, 2011, pp. 263-280.
Frazier, et al., "First Human Use of the Hemopump, a CatheterMounted Ventricular Assist Device", Ann Thorac Surg, 49, 1990, pp. 299-304.
Gomes, et al., "Heterologous Valve Implantation in the Infra-Renal Vena Cava for Treatment of the Iliac Venous Valve Regurgitation Disease: Experimental Study", Rev Bras Cir Cardiovasc, vol. 17(4), 2002, pp. 367-369.
Haddy, et al., "Effect of Elevation of Intraluminal Pressure on Renal Vascular Resistance", Circulation Research Journal of the American Heart Association, vol. 4, 1956, pp. 659-663.
Heywood, et al., "High Prevalence of Renal Dysfunction and Its Impact on Outcome in 118,465 Patients Hospitalized With Acute Decompensated Heart Failure: A Report From the ADHERE Database", Journal of Cardiac Failure, vol. 13, 2007, pp. 422-430.
Hillege, et al., "Renal Function as a Predictor of Outcome in a Broad Spectrum of Patients With Heart Failure", Circulation Journal of the American Heart Association, vol. 113, 2006, pp. 671-678.
Hillege, et al., "Renal Function, Neurohormonal Activation, and Survival in Patients With Chronic Heart Failure", Circulation Journal of the American Heart Association, vol. 102, 2000, pp. 203-210.
Hsu, et al., "Review of recent patents on foldable ventricular assist devices", Recent Patents on Biomedical Engineering, 5.3, 2012, pp. 208-222.
Ikari, , "The Physics of Guiding Catheter; The IKARI Guiding Catheter in TRI", available at httu:i /www.docstoc.com/docs/148136553/The-[KARI-catheter---anovel-guide-for-TRI--, uploaded on Mar. 8, 2013.

(56) References Cited

OTHER PUBLICATIONS

Kafagy, et al., "Design of axial blood pumps for patients with dysfunctional fontan physiology: computational studies and performance testing", Artificial organs, 39.1, 2015, pp. 34-42.
Kang, et al., "Fluid dynamics aspects of miniaturized axial-flow blood pump", Bio-medical materials and engineering, 24.1, 2014, pp. 723-729.
Koochaki, et al., "A new design and computational fluid dynamics study of an implantable axial blood pump", Australasian Physical & Engineering Sciences in Medicine, 36.4, 2013, pp. 417-422.
Lauten, et al., "Heterotopic Transcatheter Tricuspid Valve Implantation: First-In-Man Application of a Novel Approach to Tricuspid Regurgitation", European Heart Journal, (1-7 as printed), Feb. 15, 2011, pp. 1207-1213.
McAlister, et al., "Renal Insufficiency and Heart Failure: Prognostic and Therapeutic Implications From a Prospective Cohort Study", Circulation Journal of the American Heart Association, 109, 2004, pp. 1004-1009.
Meyns, et al., "The Heart-Hemopump Interaction: A Study of Hemopump Flow as a Function of Cardiac Activity", Artificial Organs, Vot. 20, No. 6, 1996, pp. 641-649.
Mullens, et al., "Elevated Intra-Abdominal Pressure in Acute Decompensated Heart Failure. A Potential Contributor to Worsening Renal Function", Journal of the American College of Cardiology, vol. 51, 2008, pp. 300-306.
Mullens, et al., "Importance of Venous Congestion for Worsening of Renal Function in Advanced Decompensated Heart Failure", Journal of American College of Cardiology, vol. 53, 2009, pp. 589-596.
Mullens, et al., "Prompt Reduction in Intra-Abdominal Pressure Following Large-Volume Mechanical Fluid Removal Improves Renal Insufficiency in Refractory Decompensated Heart Failure", Journal of Cardiac Failure, vol. 14, 2008, pp. 508-514.
Notarius, et al., "Central Venous Pressure During Exercise: Role of Muscle Pump", Canadian Journal of Physiology and Pharmacology, vol. 74(6), 1996, pp. 647-651.
Park, et al., "Nutcracker Syndrome: Intravascular Stenting Approach", Nephrol Dial Transplant, vol. 15, 2000, pp. 99-101.
Reul, et al., "Blood pumps for circulatory support", Perfusion-Sevenoaks, 15.4, 2000, pp. 295-312.
Reul, et al., "Rotary blood pumps in circulatory assist", Perfusion, 10(3), May 1995, pp. 153-158.
Schmitz-Rode, et al., "An Expandable Percutaneous Catheter Pump for Left Ventricular Support", Journal of the American College of Cardiology, vol. 45, 2005, pp. 1856-1861.
Schmitz-Rode, et al., "Axial flow catheter pump for circulatory support", Biomed Tech (Berl), 47 Suppl 1 Pt 1, 2002, pp. 142-143.
Semple, et al., "Effect of Increased Renal Venous Pressure on Circulatory "Autoregulation" of Isolated Dog Kidneys", Circulation Research Journal of the American Heart Association, vol. 7, 1959, pp. 643-648.
Siess, et al., "Concept, realization, and first in vitro testing of an intraarterial microaxial blood pump", Artificial Organs, vol. 15, No. 7, 1995, pp. 644-652.
Siess, et al., "Hemodynamic system analysis of intraarterial microaxial pumps in vitro and in vivo", Artificial Organs, vol. 20, No. 6, Jun. 1996, pp. 650-661.
Siess, , "PhD Chapter 3—English translation", (citation info here: https://www.shaker.eu/en/content/catalogue/index.asp?lang=en&ID=8&ISBN=978-3-8265-6150-4&search=yes ).
Song, et al., "Axial flow blood pumps", ASAIO journal, 49, 2003, pp. 355-364.
Tang, et al., "Anemia in Chronic Heart Failure: Prevalence, Etiology, Clinical Correlates, and Treatment Options", Circulation Journal of the American Heart Association, vol. 113, 2006, pp. 2454-2461.
Throckmorton, et al., "Design of a protective cage for an intra vascular axial flow blood pump to mechanically assist the failing Fontan", Artificial organs, 33.8, 2009, pp. 611-621.
Thunberg, et al., "Ventricular assist devices today and tomorrow", Journal of cardiothoracic and vascular anesthesia, 24.4, 2010, pp. 656-680.
Timms, , "A review of clinical ventricular assist devices", Medical engineering & physics, 33.9, 2011, pp. 1041-1047.
Triep, et al., "Computational Fluid Dynamics and Digital Particle Image Velocimetry Study of the Flow Through an Optimized Micro-axial Blood Pump", Artificial Organs, vol. 30, No. 5, May 2006, pp. 384-391.
Uthoff, et al., "Central venous pressure at emergency room presentation predicts cardiac rehospitalization in patients with decompensated heart failure", European Journal of Heart Failure, 12, 2010, pp. 469-476.
Van Mieghem, et al., "Design and Principle of Operation of the HeartMate PHPTM (Percutaneous Heart Pump)", EuroIntervention, Jaa-035 2016, doi: 10.4244/ EIJ-D-15-00467, 2016.
Vercaemst, et al., "Impella: A Miniaturized Cardiac Support System in an Era of Minimal Invasive Cardiac Surgery", Presented at the 39th International Conference of the American Society of Extra-Corporeal Technology, Miami, Florida, Mar. 22-25, 2001.
Wampler, , "The first co-axial flow pump for human use: the Hemopump", Flameng W. (eds) Temporary Cardiac Assist with an Axial Pump System, 1991.
Wencker, , "Acute Cardio-Renal Syndrome: Progression From Congestive Heart Failure to Congestive Kidney Failure", Current Heart Failure Reports, vol. 4, 2007, pp. 134-138.
Winton, , "The Control of Glomerular Pressure by Vascular Changes Within the Mammalian Kidney, Demonstrated by the Actions of Adrenaline", Journal of Physiology, vol. 73, Nov. 1931, pp. 151-162.
Winton, , "The Influence of Venous Pressure on the Isolated Mammalian Kidney", Journal of Physiology, vol. 72(1), Jun. 6, 1931, pp. 49-61.
Wood, , "The Mechanism of the Increased Venous Pressure With Exercise in Congestive Heart Failure", Journal of Clinical Investigation, vol. 41(11), 1962, pp. 2020-2024.
Wu, et al., "Design and simulation of axial flow maglev blood pump", International Journal of Information Engineering and Electronic Business, 3.2, 2011, p. 42.
Yancy, et al., "Clinical Presentation, Management, and In-Hospital Outcomes of Patients Admitted With Acute Decompensated Heart Failure With Preserved Systolic Function. A Report From the Acute Decompensated Heart Failure National Registry (ADHERE) Database", Journal of the American College of Cardiology, vol. 47(1), 2006, pp. 76-84.
U.S. Appl. No. 62/796,138, filed Jan. 24, 2019.
U.S. Appl. No. 62/851,716, filed May 23, 2019.
U.S. Appl. No. 62/870,821, filed Jul. 5, 2019.
U.S. Appl. No. 62/896,026, filed Sep. 5, 2019.
Issue Notification for U.S. Appl. No. 16/281,264 mailed Dec. 16, 2020.
Non-Final Office Action for U.S. Appl. No. 16/276,965 dated Nov. 30, 2020.
Non-Final Office Action for U.S. Appl. No. 16/280,566 dated Dec. 21, 2020.
Notice of Allowance for U.S. Appl. No. 16/278,482 dated Dec. 2, 2020.
U.S. Appl. No. 16/952,327, filed Nov. 19, 2020.
U.S. Appl. No. 16/952,389, filed Nov. 19, 2020.
U.S. Appl. No. 16/952,444, filed Nov. 19, 2020.
International Search Report and Written Opinion from International Application No. PCT/IB2020/050515 dated Sep. 9, 2020.
Non-Final Office Action for U.S. Appl. No. 16/275,559 dated Sep. 4, 2020.
Non-Final Office Action for U.S. Appl. No. 16/279,352 dated Nov. 10, 2020.
Notice of Allowance for U.S. Appl. No. 16/281,264 dated Nov. 12, 2020.
U.S. Appl. No. 17/069,064, filed Oct. 13, 2020.
U.S. Appl. No. 17/069,321, filed Oct. 13, 2020.
U.S. Appl. No. 17/069,570, filed Oct. 13, 2020.
U.S. Appl. No. 17/070,323, filed Oct. 14, 2020.
U.S. Appl. No. 17/070,670, filed Oct. 14, 2020.

(56) References Cited

OTHER PUBLICATIONS

U.S. Appl. No. 17/077,769, filed Oct. 22, 2020.
U.S. Appl. No. 17/078,439, filed Oct. 23, 2020.
U.S. Appl. No. 17/078,472, filed Oct. 23, 2020.
Extended European Search Report for European Application No. 20159714.3 dated Jul. 3, 2020.
Extended European Search Report for European Application No. 20159716.8 dated Jul. 3, 2020.
Extended European Search Report for European Application No. 20159718.4 dated Jul. 9, 2020.
Invitation to Pay Additional Fees for International Application No. PCT/IB2020/050515 dated Mar. 31, 2020.
Non-Final Office Action for U.S. Appl. No. 16/276,965 dated Jun. 19, 2020.
Non-Final Office Action for U.S. Appl. No. 16/278,482 dated Jun. 23, 2020.
Non-Final Office Action for U.S. Appl. No. 16/281,264 dated Jun. 29, 2020.
Restriction Requirement for U.S. Appl. No. 16/275,559 dated Jun. 2, 2020.
Restriction Requirement for U.S. Appl. No. 16/279,352 dated Aug. 11, 2020.
Restriction Requirement for U.S. Appl. No. 16/280,566 dated Aug. 11, 2020.
U.S. Appl. No. 16/750,354, filed Jan. 23, 2020.
Bai, et al., "A Split-Array, C-2C Switched-Capacitor Power Amplifier in 65 nm CMOS", IEEE Radio Frequency Integrated Circuits Symposium, 2017, pp. 336-339.
Final Office Action for U.S. Appl. No. 16/275,559 dated Jan. 4, 2021.
Issue Notification for U.S. Appl. No. 16/278,482 dated Jan. 13, 2021.
Supplemental Notice of Allowability for U.S. Appl. No. 16/278,482 dated Dec. 24, 2020.

* cited by examiner

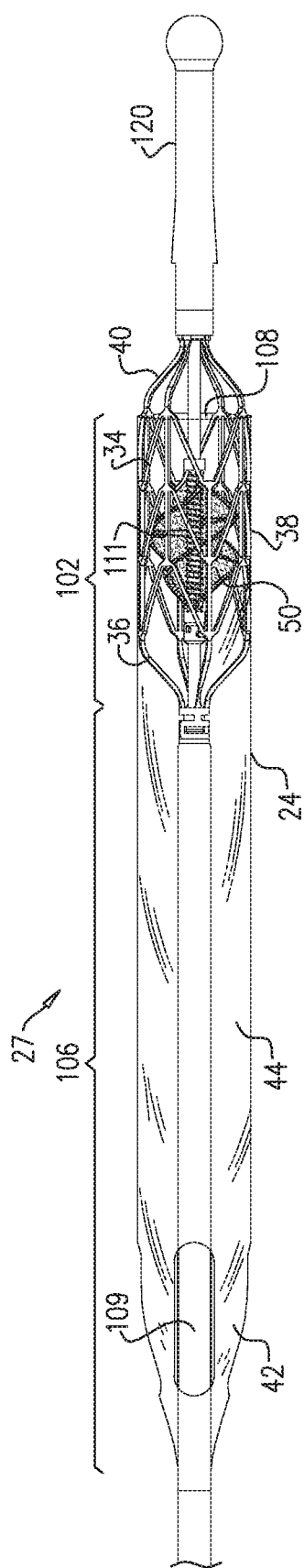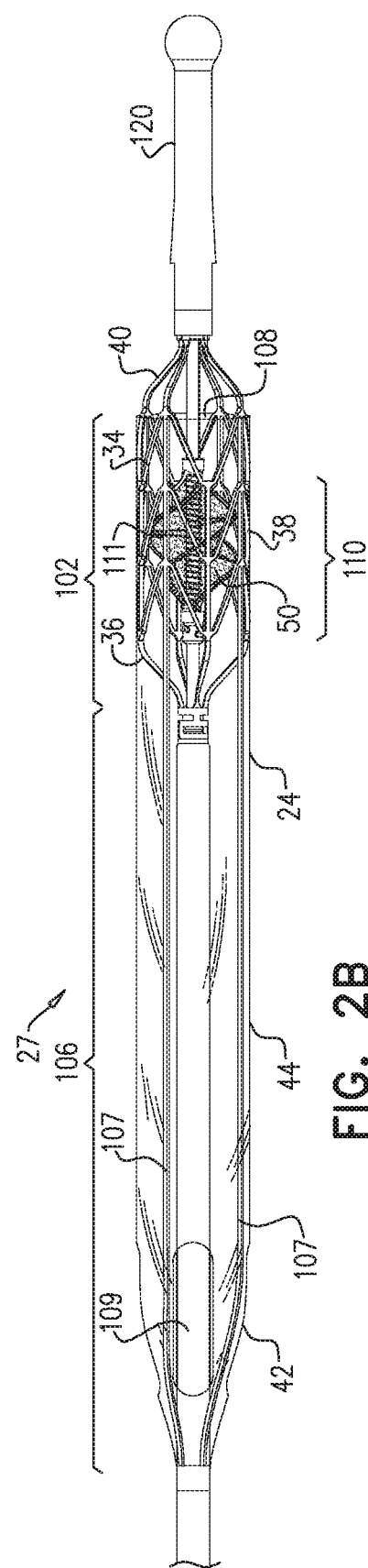

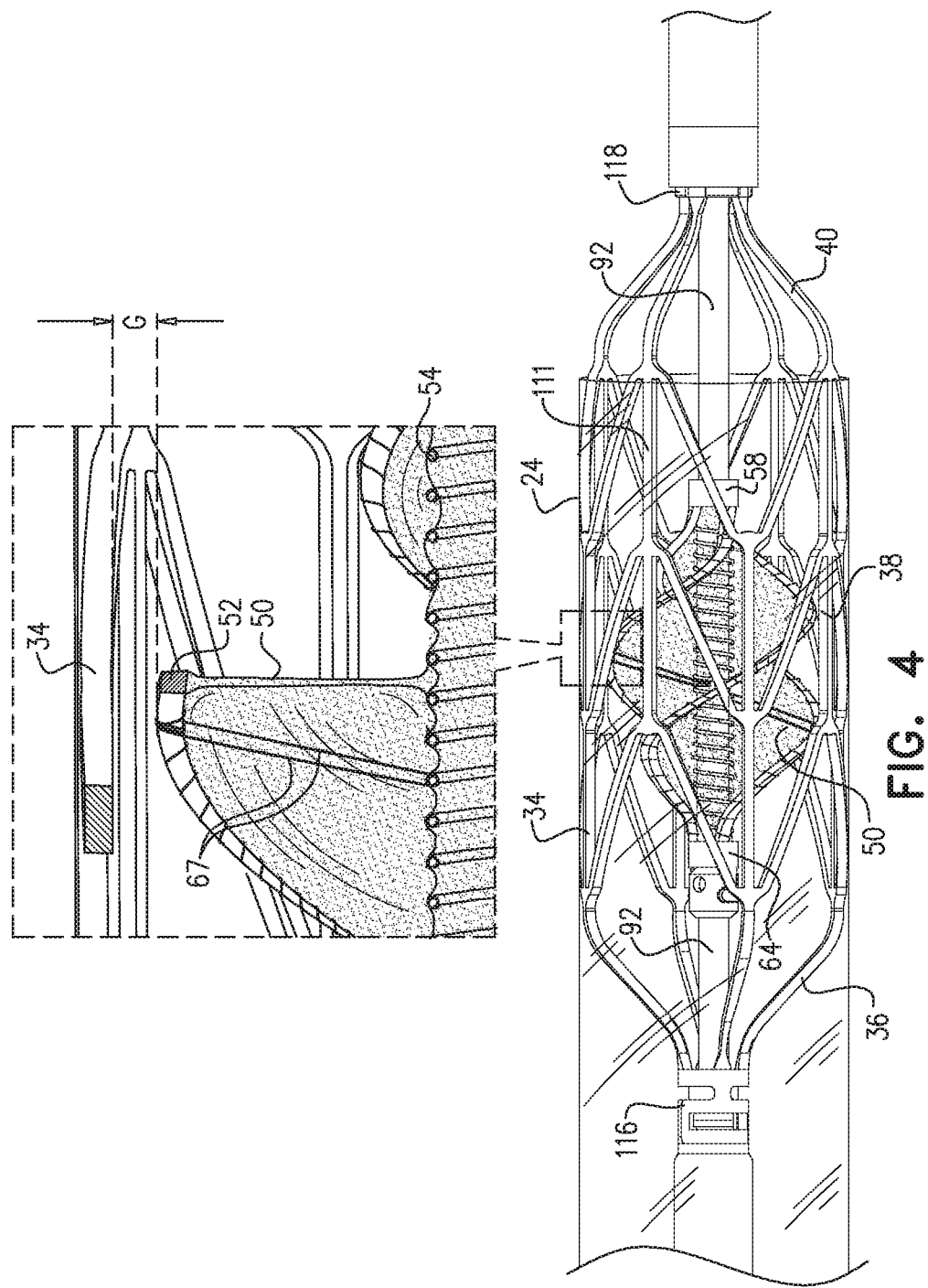

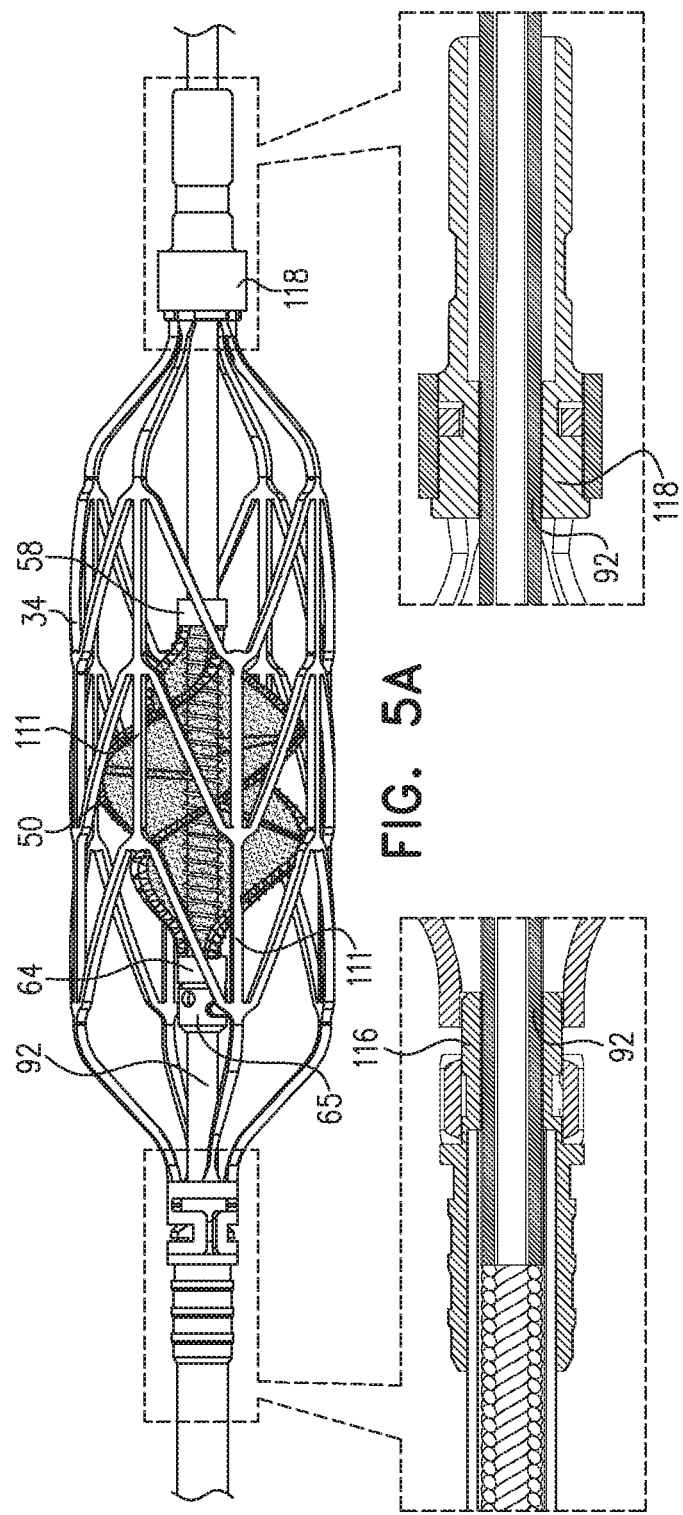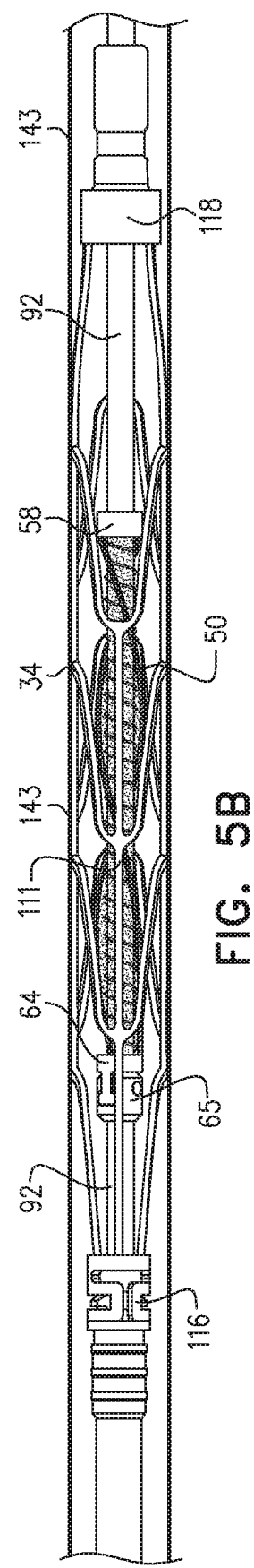
FIG. 5A
FIG. 5B

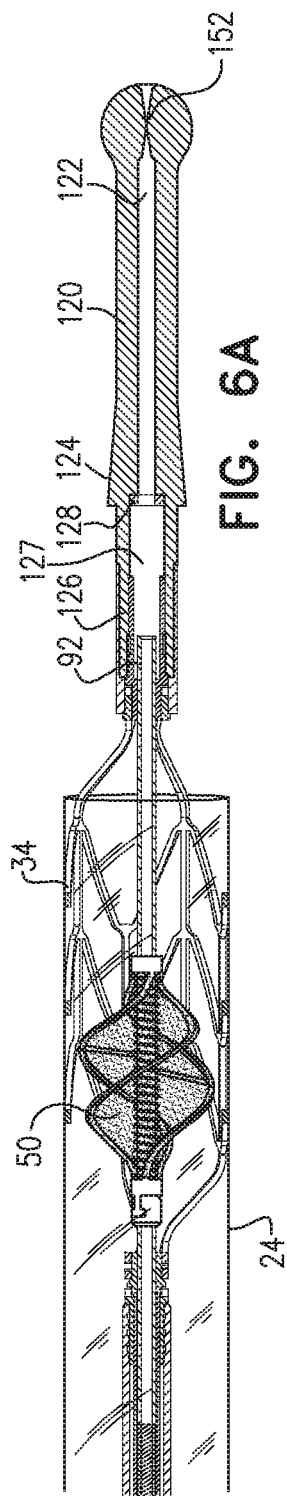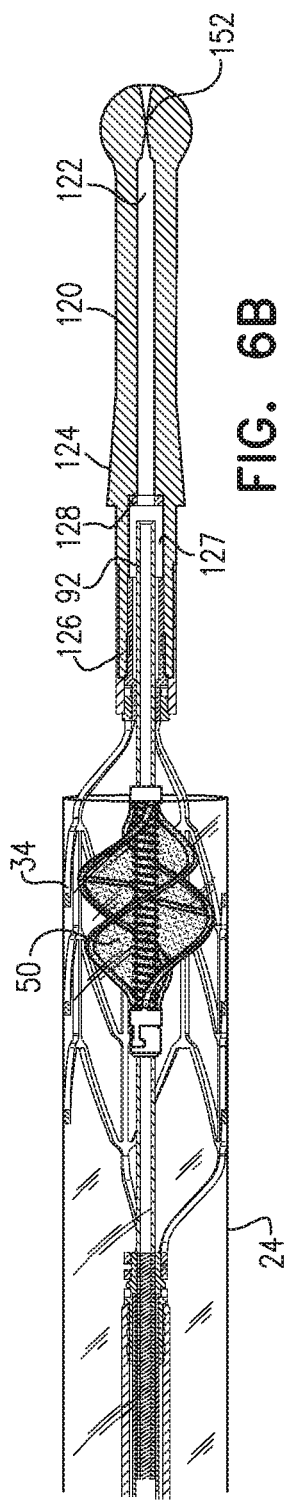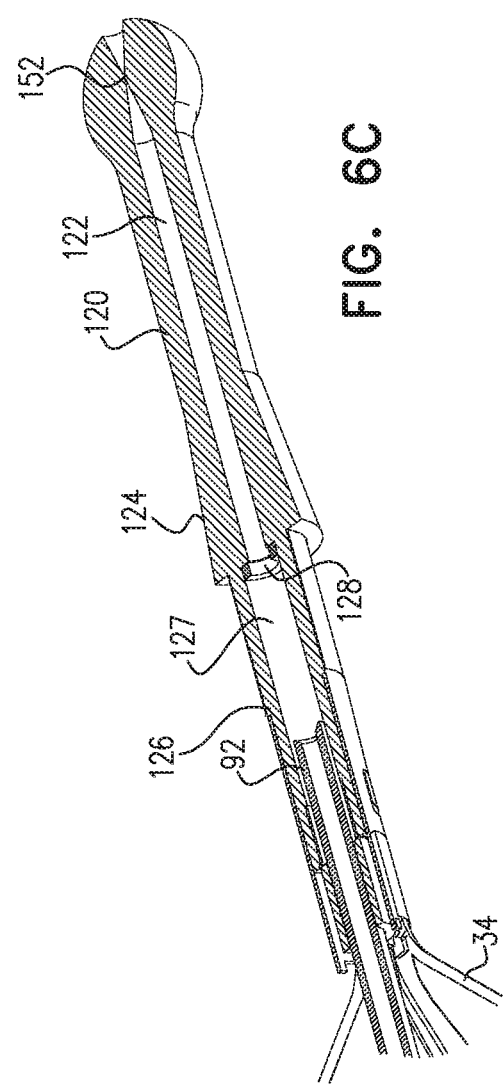

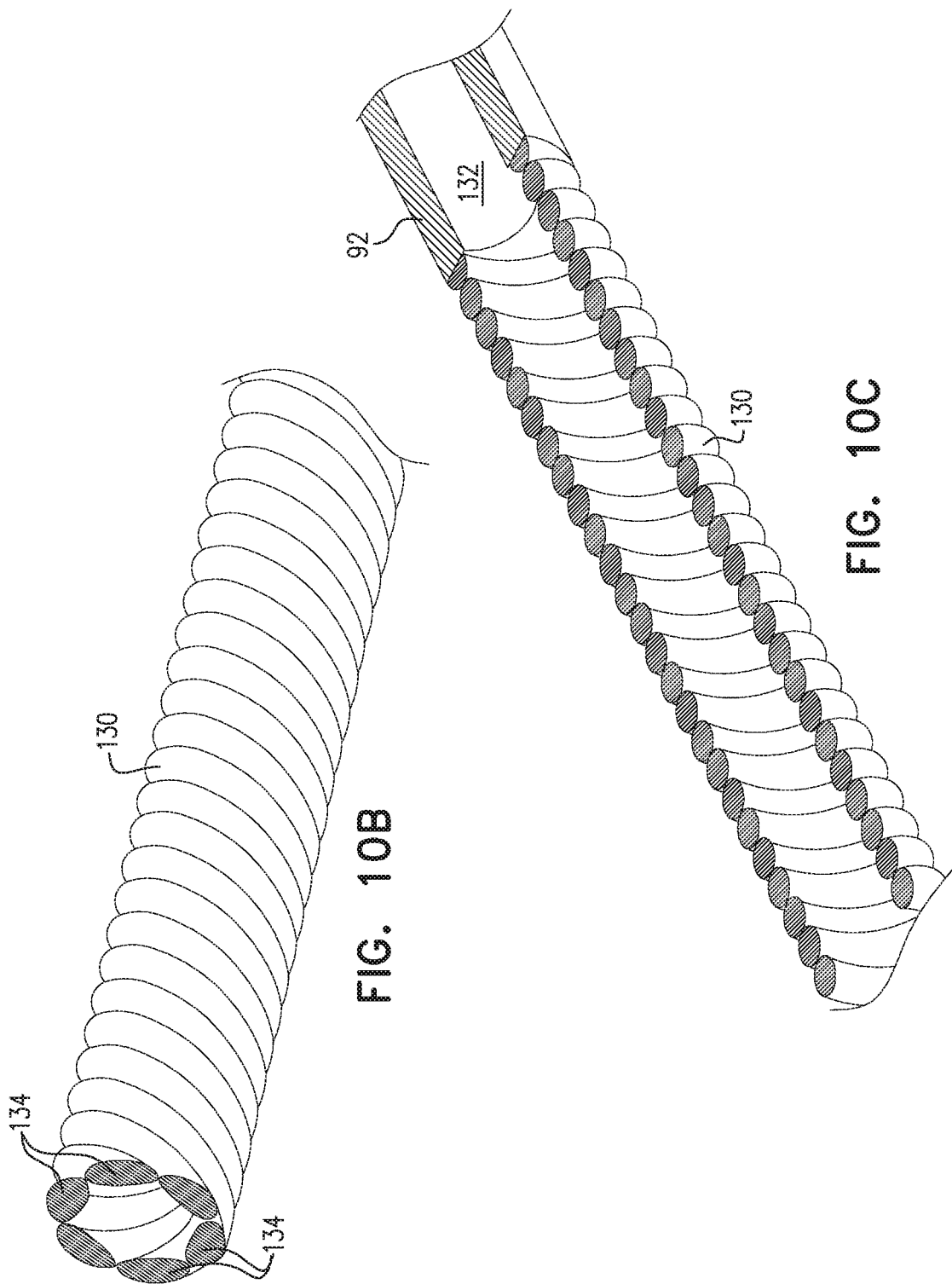

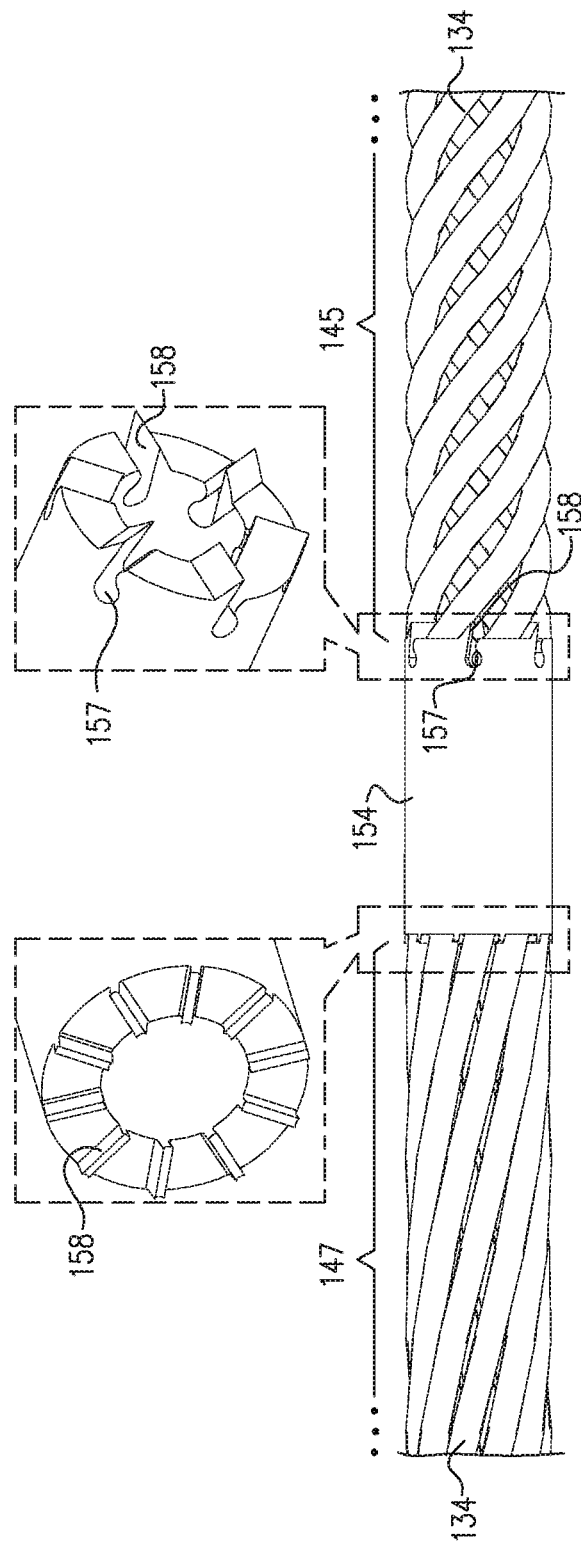
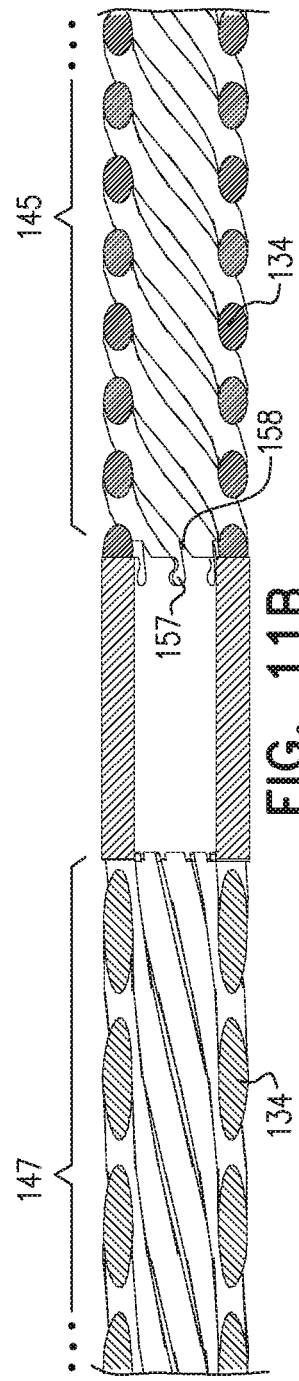
FIG. 11A
FIG. 11B

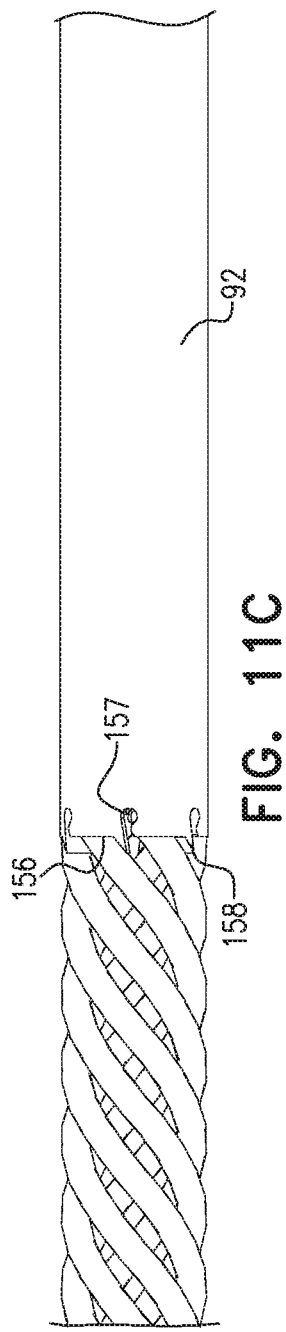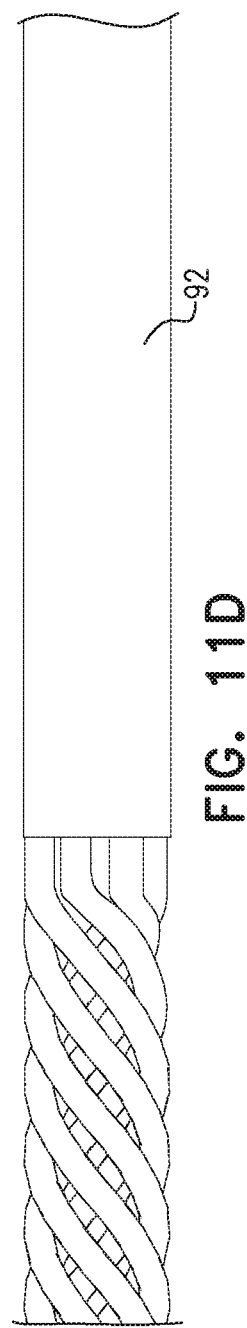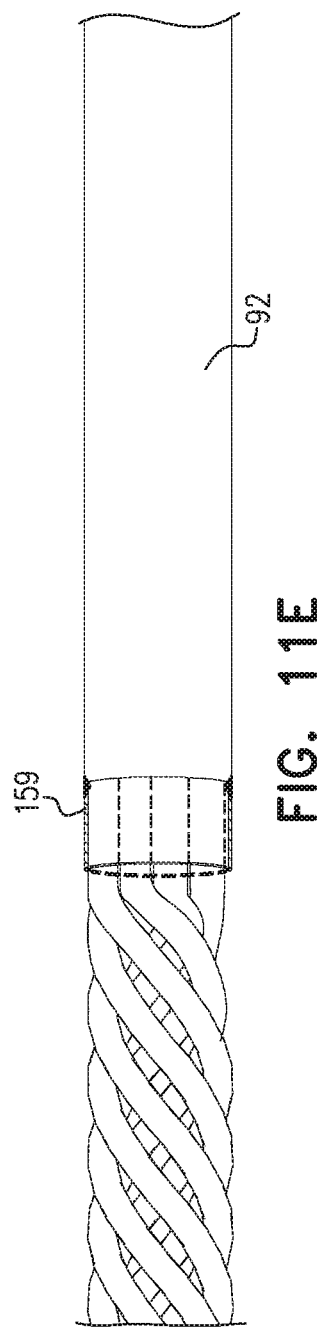

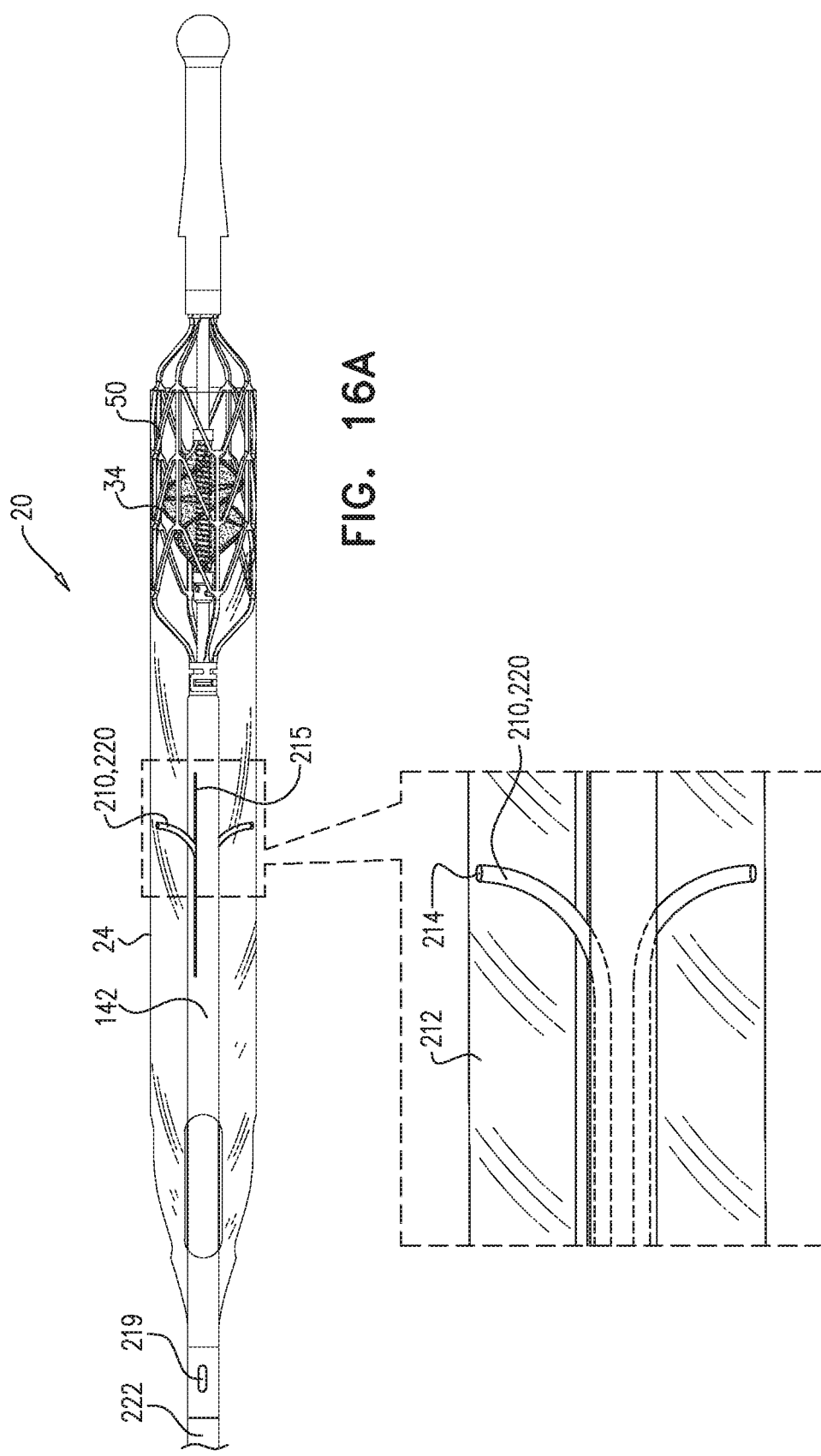

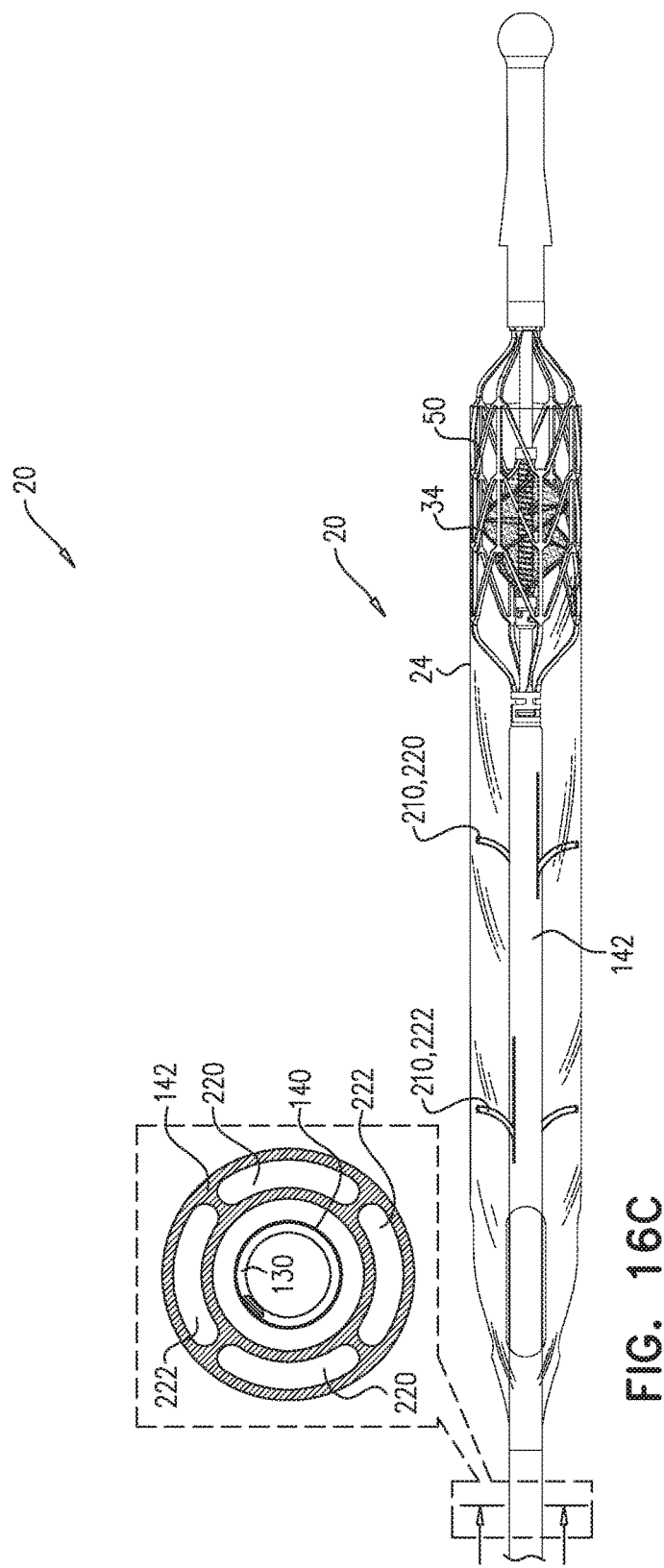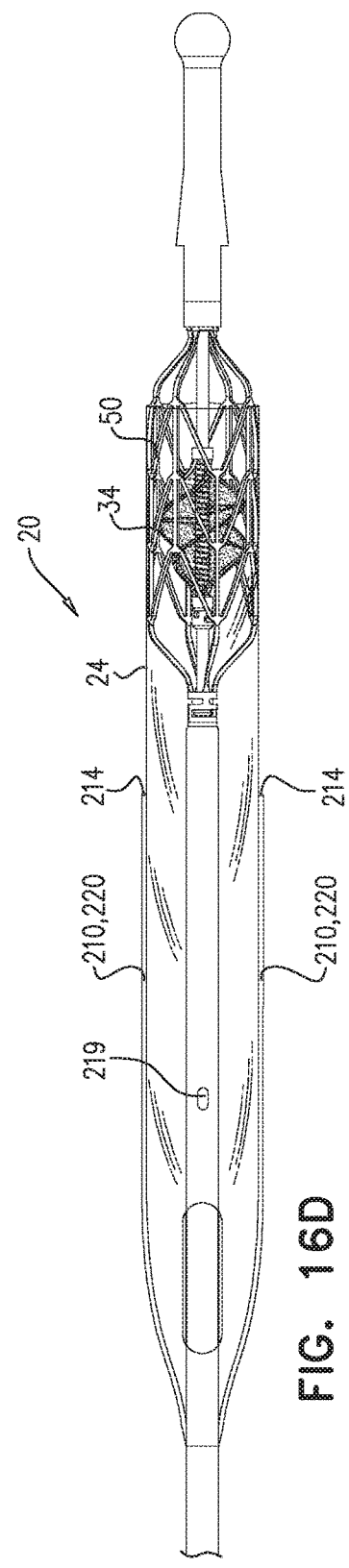

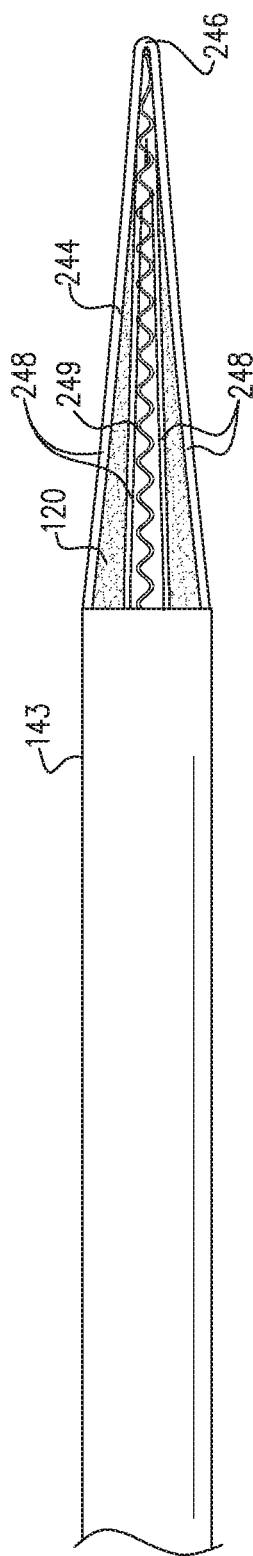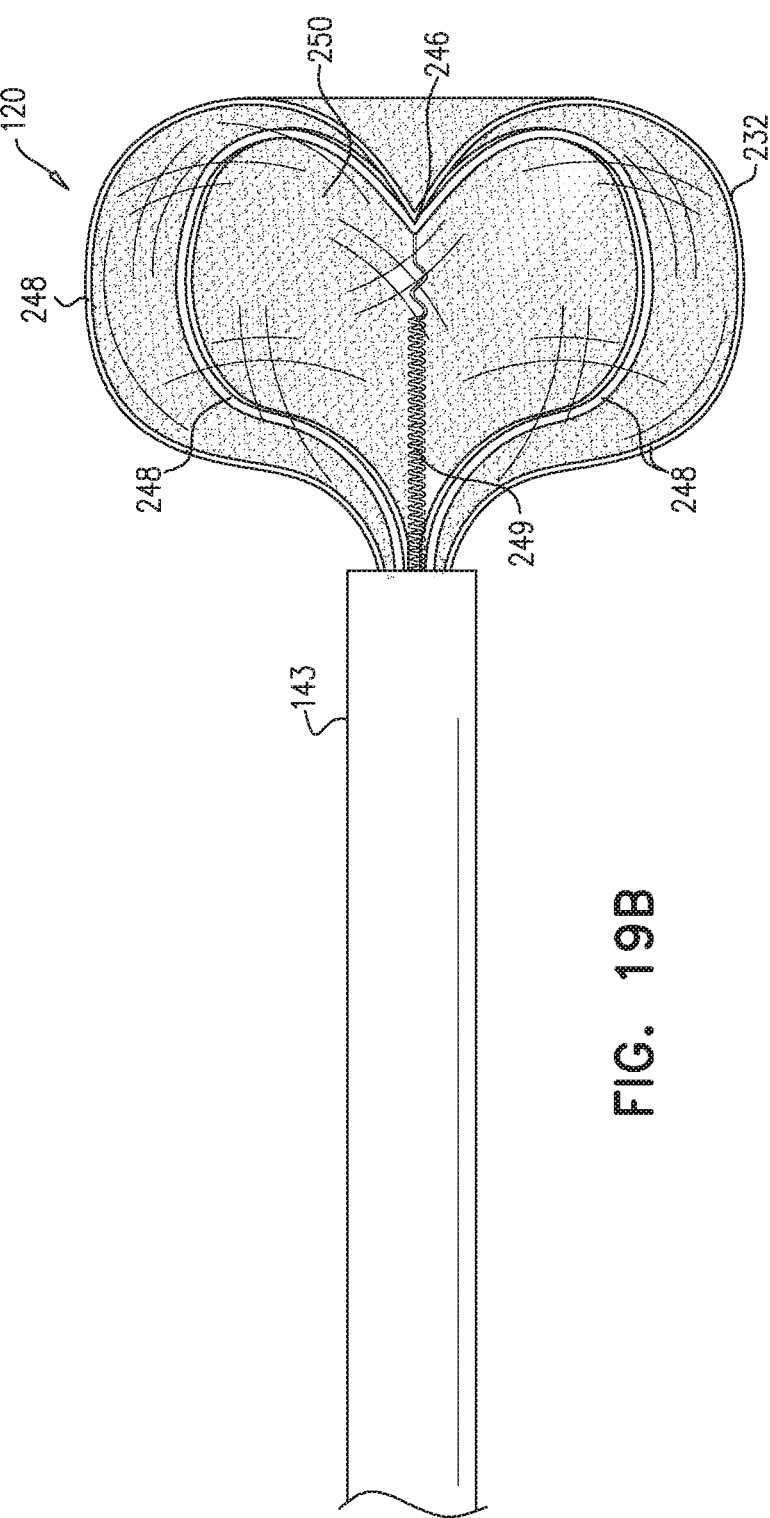

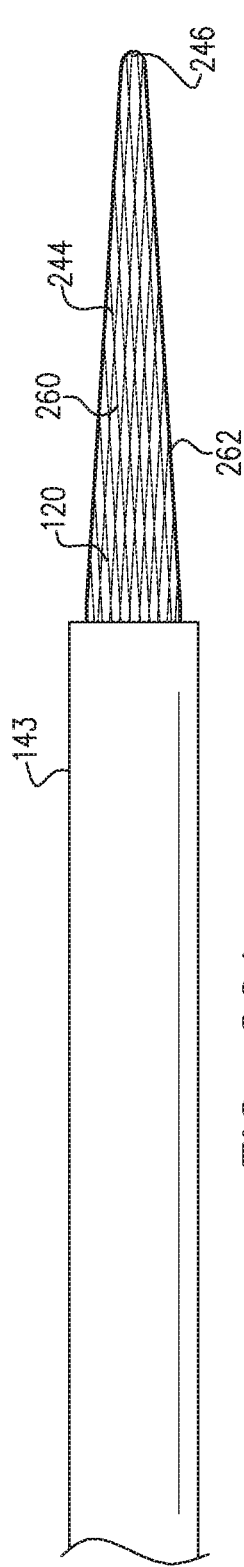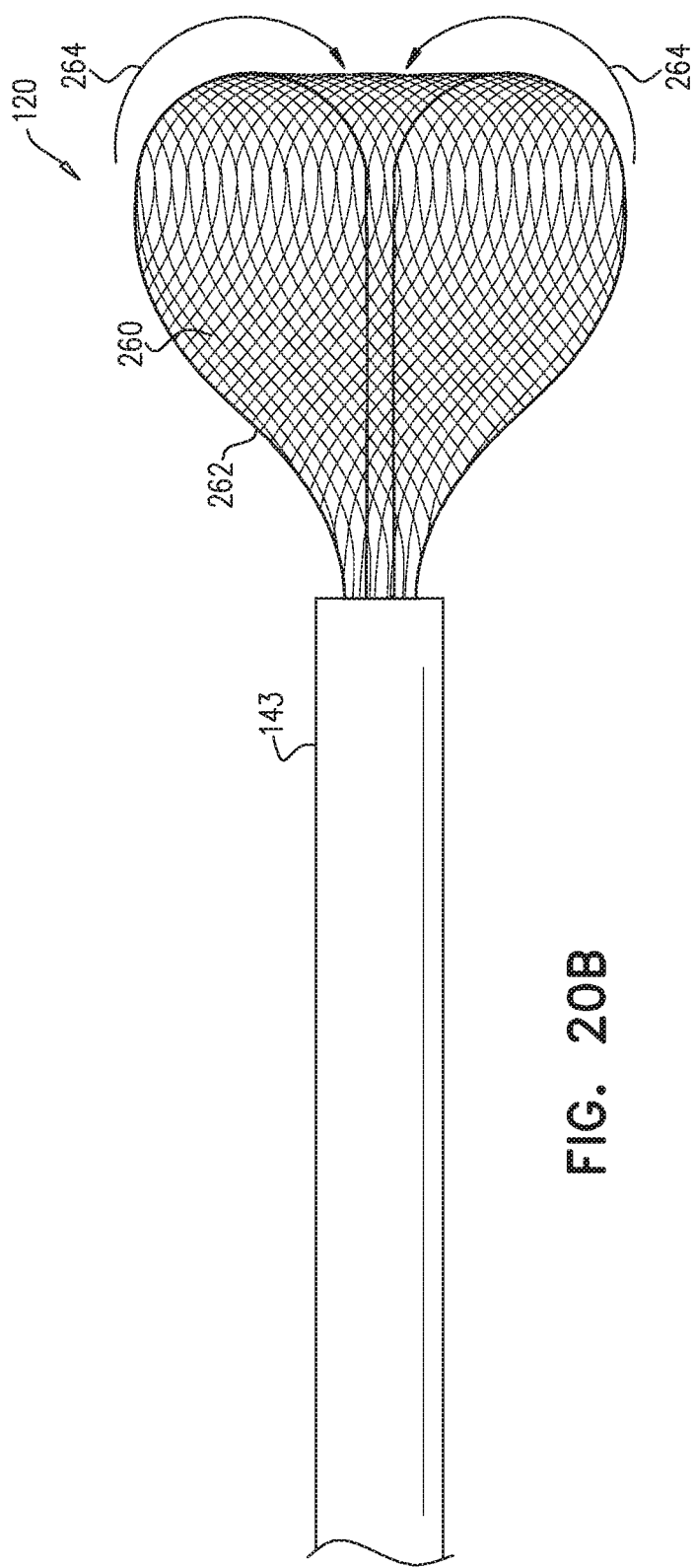

VENTRICULAR ASSIST DEVICE

CROSS-REFERENCES TO RELATED APPLICATIONS

The present application is a continuation of International Application No. PCT/IB2019/050186 to Tuval (published as WO 19/138350), filed Jan. 10, 2019, entitled "Ventricular assist device," which claims priority from:

U.S. Provisional Patent Application 62/615,538 to Sohn, entitled "Ventricular assist device," filed Jan. 10, 2018;

U.S. Provisional Patent Application 62/665,718 to Sohn, entitled "Ventricular assist device," filed May 2, 2018;

U.S. Provisional Patent Application 62/681,868 to Tuval, entitled "Ventricular assist device," filed Jun. 7, 2018; and U.S. Provisional Patent Application 62/727,605 to Tuval, entitled "Ventricular assist device," filed Sep. 6, 2018.

FIELD OF EMBODIMENTS OF THE INVENTION

Some applications of the present invention generally relate to medical apparatus. Specifically, some applications of the present invention relate to a ventricular assist device and methods of use thereof.

BACKGROUND

Ventricular assist devices are mechanical circulatory support devices designed to assist and unload cardiac chambers in order to maintain or augment cardiac output. They are used in patients suffering from a failing heart and in patients at risk for deterioration of cardiac function during percutaneous coronary interventions. Most commonly a left-ventricular assist device is applied to a defective heart in order to assist left-ventricular functioning. In some cases, a right-ventricular assist device is used in order to assist right-ventricular functioning. Such assist devices are either designed to be permanently implanted or mounted on a catheter for temporary placement.

Summary of Embodiments

In accordance with some applications of the present invention, a ventricular assist device includes an impeller disposed upon an axial shaft, with a frame disposed around the impeller. The ventricular assist device typically includes a tube, which traverses the subject's aortic valve, such that a proximal end of the tube is disposed in the subject's aorta and a distal end of the tube is disposed within the subject's left ventricle. The impeller, the axial shaft and the frame are disposed within a distal portion of the tube inside the subject's left ventricle. Typically, the impeller is configured to pump blood from the left ventricle into the aorta by rotating. The tube typically defines one or more blood inlet openings at the distal end of the tube, via which blood flows into the tube from the left ventricle, during operation of the impeller. For some applications, the proximal portion of the tube defines one or more blood outlet openings, via which blood flows from the tube into the ascending aorta, during operation of the impeller.

For some applications, the impeller includes proximal and distal bushings, and the frame includes proximal and distal bearings. The axial shaft typically passes through the proximal and distal bearings of the frame and the proximal and distal bushings of the impeller. For some applications, (a) the proximal bushing of the impeller is coupled to the axial shaft, such that the proximal bushing is held in an axially-fixed position with respect to the axial shaft, and (b) the distal bushing of the impeller is not coupled to the axial shaft, such that the distal bushing is not held in an axially-fixed position with respect to the axial shaft. Typically, the impeller defines a radially-constrained configuration in which the impeller is introduced into the subject's body and a non-radially-constrained configuration in which the impeller is configured to pump blood within the subject's body. For some applications, the impeller changes from its radially-constrained configuration to its non-radially-constrained configuration by the distal bushing sliding over the axial shaft.

Typically, the axial shaft is not held in an axially-fixed position with respect to the proximal and distal bearings. Further typically, the ventricular assist device (and/or a blood pump portion thereof) does not include any thrust bearing configured to be disposed within the subject's body. For some applications, the ventricular assist device includes one or more thrust bearings that are disposed outside the subject's body, and opposition to thrust generated by the rotation of the impeller is provided solely by the one or more thrust bearings disposed outside the subject's body.

For some applications, a motor drives the impeller to pump blood from the left ventricle to the aorta, by rotating the impeller, and the impeller is configured to undergo axial motion with respect to the frame, in response to the pressure difference between the left ventricle and the aorta changing. For some applications, a computer processor measures an indication of the axial motion of the impeller. For some applications, the computer processor derives the subject's cardiac cycle, the pressure difference between the left ventricle and the aorta, and/or left-ventricular pressure of the subject, based upon the measured indication of the axial motion of the impeller. For some applications, the computer processor changes a rate of rotation of the impeller, at least partially based upon the sensor signal. For example, the computer processor may determine left-ventricular pressure of the subject, at least partially based upon the sensor signal, and may change a rate of rotation of the impeller, at least partially based upon the determined left-ventricular pressure. For some applications, the computer processor reduces the rate of rotation of the impeller, in response to determining that the subject's left-ventricular pressure has decreased. For some applications, the impeller is coupled to a magnet such that axial motion of the impeller causes the magnet to undergo axial motion, and the computer processor measures the indication of the axial motion of the impeller by measuring magnetic flux generated by the magnet.

Typically, a drive cable extends from outside the subject's body to the axial shaft, and is configured to impart rotational motion from the motor to the impeller by rotating, such that the impeller pumps blood from the left ventricle to the aorta by rotating a given direction. For some applications, at least a portion of the drive cable includes a plurality of wires disposed in a coiled configuration that is such that, in response to the drive cable rotating in the given direction of rotation, the plurality of wires disposed in the coiled configuration at least partially unwind, such that the portion of the drive cable shortens axially. For some applications, an outer tube is disposed around the drive cable, and frictional forces between the outer tube and the drive cable are such as to typically generate debris. Alternatively or additionally, a fluid (e.g., a purging fluid) is disposed between the outer tube and the drive cable. For some such applications, at least a portion of the drive cable is configured such that the plurality of wires disposed in the coiled configuration are configured to pump the debris and/or the fluid toward the proximal end of the drive cable.

For some applications, the drive cable includes a first portion configured to be disposed at least partially within an aortic arch of the subject, and a second portion configured to be disposed at least partially within a descending aorta of the subject, and the flexibility of the first portion is greater than the flexibility of the second portion. For example, the first portion of the drive cable may include a first number of wires disposed in a coiled configuration, and the second portion of the drive cable may include a second number of wires disposed in a coiled configuration, and the first number is lower than the second number. For example, the first portion of the drive cable may include between 4 and 8 wires disposed in a coiled configuration, and the second portion of the drive cable may include between 8 and 12 wires disposed in a coiled configuration.

For some applications, the impeller includes at least one helical elongate element (and typically, three helical elongate elements), and a spring that is disposed inside of the helical elongate element, and along an axis around which the helical elongate element winds. Typically, a film of material (e.g., silicone) is supported between the helical elongate element and the spring. For some applications, at least one elongate element (e.g., a string or a wire) extends from the spring to the helical elongate element and is configured to maintain the helical elongate element within a given distance from the spring.

As described hereinabove, for some applications, a frame is disposed around the impeller. For some applications, the ventricular assist device includes a stator that includes a plurality of curved projections that are coupled to a proximal end of the frame. Typically, the curvature of the curved projections opposes the direction of rotation of the impeller. For some applications, the curvature of the curved projections is such that, from distal ends of the curved projections to proximal ends of the curved projections, the curved projections become progressively closer to being parallel with the longitudinal axis of the frame. Typically, the curved projections comprise a plurality of curved struts that are integral with the frame, and a flexible material (e.g., silicone) that extends from the curved struts. For some applications, the flexible material is shaped to define a lumen therethrough.

As described hereinabove, typically the impeller is disposed within a tube (which is sometimes referred to herein as a "blood-pump tube") that extends from the subject's left ventricle to the subject's aorta. For some applications, at least one blood-pressure-measurement tube, which defines an opening at its distal end, extends to at least an outer surface of the blood-pump tube, such that the opening at the distal end of the blood-pressure-measurement tube is in direct fluid communication with the subject's bloodstream outside the blood-pump tube. A pressure sensor measures pressure of blood within the blood-pressure-measurement tube. For some applications, the blood-pressure-measurement tube is configured to pass along an outer surface of the blood-pump tube from the proximal end of the blood-pump tube until the opening at the distal end of the blood-pressure-measurement tube. Typically, the blood-pressure-measurement tube is a left-ventricular blood-pressure measurement tube that is configured to extend to the outer surface of the blood-pump tube at a location along the blood-pump tube that is configured to be within the subject's left ventricle proximal to the impeller, and the pressure sensor is configured to measure left-ventricular pressure of the subject by measuring pressure of blood within the left-ventricular blood-pressure-measurement tube.

Typically, the blood-pump tube defines one or more blood inlet openings within the distal portion of the blood-pump tube, and one or more blood outlet openings within a proximal portion of the blood-pump tube. For some applications, the ventricular assist device includes a radially-expandable atraumatic distal tip portion configured to be disposed within the subject's left ventricle distally with respect to the one or more blood inlet openings. The distal tip portion is typically configured to be inserted into the left ventricle in a radially-constrained configuration, and to assume a non-radially-constrained configuration within the subject's left ventricle in which at least a radially-expandable portion of the distal tip portion is radially expanded relative to the radially-constrained configuration of the distal tip portion. Typically, in its non-radially-constrained configuration, the radially-expandable portion of the distal tip portion separates the one or more blood inlet openings from inner structures of the left ventricle, such as the interventricular septum, chordae tendineae, papillary muscles, and/or the apex of the left ventricle. Further typically, in its non-radially-constrained configuration, the radially-expandable portion of the distal tip portion separates the one or more blood inlet openings from the inner structures of the left ventricle in three dimensions. For some applications, in its non-radially-constrained configuration, the radially-expandable portion of the distal tip portion directs blood flow from the left ventricle into the one or more blood inlet openings.

For some applications, in the radially-constrained configuration of the distal tip portion, a distal region of the distal tip portion is configured to be least semi-rigid, and is shaped to radially converge along a longitudinal direction toward a distal end of the distal tip portion. Typically, the ventricular assist device is configured to be inserted into the subject's body via a puncture in the subject's body. For some applications, during the insertion of the ventricular assist device, the distal region of the distal tip portion is configured to act as a dilator by dilating the puncture.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

There is therefore provided, in accordance with some applications of the present invention, apparatus including:
a blood pump configured to be placed inside a body of subject, the blood pump including:
   an impeller including proximal and distal bushings;
   a frame configured to be disposed around the impeller, the frame including proximal and distal bearings;

an axial shaft configured to pass through the proximal and distal bearings of the frame and the proximal and distal bushings of the impeller, the proximal bushing of the impeller being coupled to the axial shaft, such that the proximal bushing is held in an axially-fixed position with respect to the axial shaft, and the distal bushing of the impeller not being coupled to the axial shaft, such that the distal bushing is not held in an axially-fixed position with respect to the axial shaft, and the impeller defining a radially-constrained configuration in which the impeller is introduced into the subject's body and a non-radially-constrained configuration in which the impeller is configured to pump blood within the subject's body, the impeller being configured to change from its radially-constrained configuration to its non-radially constrained configuration by the distal bushing sliding over the axial shaft.

In some applications, the impeller is configured to be placed inside a left ventricle of the subject, and to pump blood from the subject's left ventricle to an aorta of the subject. In some applications, the impeller is configured to be placed inside a right ventricle of the subject, and to pump blood from the subject's right ventricle to a pulmonary artery of the subject. In some applications, the impeller is configured to be placed inside a blood vessel of the subject. In some applications, the impeller is configured to be placed inside a cardiac chamber of the subject.

In some applications, the impeller includes:

at least one helical elongate element that extends from the proximal bushing to the distal bushing;

a spring that is disposed inside of the helical elongate element, and along an axis around which the helical elongate element winds;

a film of material supported between the helical elongate element and the spring; and at least one flexible elongate element extending from the spring to the helical elongate element and configured to maintain the helical elongate element within a given distance from the spring, the at least one flexible elongate element being selected from the group consisting of: a string and a wire.

In some applications, the apparatus further includes a delivery catheter, the delivery catheter is configured to maintain the impeller in its radially-constrained configuration during introduction of the impeller into the subject's body, upon the impeller being released from the delivery catheter, the impeller is configured to self-expand to thereby cause the distal bushing to slide over the axial shaft proximally, such that the impeller assumes its non-radially-constrained configuration, and in order to retract the impeller from the subject's body, the delivery catheter is configured to cause the impeller to assume its radially-constrained configuration by a distal end of the delivery catheter and the impeller being moved with respect to one another such that the distal end of the delivery catheter causes the distal bushing to slide over the axial shaft distally.

There is further provided, in accordance with some applications of the present invention, apparatus including:

a ventricular assist device including:

an impeller configured to be placed inside a left ventricle of a subject;

a frame configured to be disposed around the impeller; and a motor configured to drive the impeller to pump blood from the left ventricle to an aorta of the subject, by rotating the impeller, the impeller being configured to undergo axial back-and-forth motion with respect to the frame, in response to cyclical changes in a pressure difference between the left ventricle and the aorta.

In some applications:

the impeller includes proximal and distal bushings;

the frame includes proximal and distal bearings; and the ventricular assist device further includes an axial shaft configured to pass through the proximal and distal bearings defined by the frame and the proximal and distal bushings of the impeller, the axial shaft:

being coupled to at least one of the proximal and distal bushings of the impeller, such that the at least one bushing is held in an axially-fixed position with respect to the axial shaft, and not being held in an axially-fixed position with respect to the proximal and distal bearings.

In some applications, the ventricular assist device does not include any thrust bearing configured to be disposed within a body of the subject.

In some applications, the ventricular assist device further includes one or more thrust bearings configured to be disposed outside a body of the subject, and wherein opposition to thrust generated by the rotation of the impeller is provided solely by the one or more thrust bearings disposed outside the subject's body.

In some applications, the motor is configured to drive the impeller to pump blood from the subject's left ventricle to the subject's aorta, by rotating the impeller in a given direction of rotation; and the ventricular assist device further includes:

an axial shaft, the impeller being disposed on the axial shaft; and a drive cable configured to extend from outside a body of the subject to the axial shaft, the drive cable being configured to impart rotational motion from the motor to the impeller by rotating, at least a portion of the drive cable including a plurality of wires disposed in a coiled configuration that is such that, in response to the drive cable rotating in the given direction of rotation, the plurality of wires disposed in the coiled configuration at least partially unwind, such that the portion of the drive cable shortens axially.

In some applications, the apparatus further includes:

a sensor configured to detect an indication of axial motion of the impeller, and to generate a sensor signal in response thereto; and a computer processor configured to receive the sensor signal and to generate an output in response thereto.

In some applications, the computer processor is configured to generate an output indicating a cardiac cycle of the subject, in response to receiving the sensor signal. In some applications, the computer processor is configured to determine left-ventricular pressure of the subject, at least partially based upon the sensor signal. In some applications, the computer processor is configured to change a rate of rotation of the impeller, at least partially based upon the sensor signal.

In some applications, the computer processor is configured:

to determine left-ventricular pressure of the subject, at least partially based upon the sensor signal, and to change a rate of rotation of the impeller, at least partially based upon the determined left-ventricular pressure.

In some applications, the computer processor is configured to reduce the rate of rotation of the impeller, in response to determining that the subject's left-ventricular pressure has decreased.

In some applications, the apparatus further includes:
a magnet, the impeller being coupled to the magnet such that axial motion of the impeller causes the magnet to undergo axial motion;
a sensor configured to detect magnetic flux generated by the magnet, and to generate a sensor signal in response thereto; and
a computer processor configured to receive the sensor signal and to generate an output in response thereto.

In some applications, the computer processor is configured to generate an output indicating a cardiac cycle of the subject, in response to receiving the sensor signal. In some applications, the computer processor is configured to determine left-ventricular pressure of the subject, at least partially based upon the sensor signal. In some applications, the computer processor is configured to change a rate of rotation of the impeller, at least partially based upon the sensor signal.

In some applications, the computer processor is configured:
to determine left-ventricular pressure of the subject, at least partially based upon the sensor signal, and
to change a rate of rotation of the impeller, at least partially based upon the determined left-ventricular pressure.

In some applications, the computer processor is configured to reduce the rate of rotation of the impeller, in response to determining that the subject's left-ventricular pressure has decreased.

In some applications:
the impeller includes proximal and distal bushings;
the frame includes proximal and distal bearings;
the ventricular assist device further includes an axial shaft configured to pass through the proximal and distal bearings of the frame and the proximal and distal bushings of the impeller;
the impeller is coupled to the axial shaft such that the impeller causes the axial shaft to undergo axial back-and-forth motion with respect to the proximal and distal bearings of the frame.

In some applications, the axial shaft is configured to clean interfaces between the axial shaft and the proximal and distal bearings of the frame, by undergoing the axial back-and-forth motion with respect to the proximal and distal bearings of the frame. In some applications, the axial shaft is configured to reduce a build-up of heat at interfaces between the axial shaft and the proximal and distal bearings of the frame, by undergoing the axial back-and-forth motion with respect to the proximal and distal bearings of the frame, relative to if the axial shaft did not undergo the axial back-and-forth motion with respect to the proximal and distal bearings of the frame.

There is further provided, in accordance with some applications of the present invention, apparatus including:
a blood pump including:
an impeller including proximal and distal bushings, and configured to pump blood through the subject's body;
a frame configured to be disposed around the impeller, the frame including proximal and distal bearings;
an axial shaft configured to pass through the proximal and distal bearings of the frame and the proximal and distal bushings of the impeller, the axial shaft:
being coupled to at least one of the proximal and distal bushings of the impeller, such that the at least one bushing is held in an axially-fixed position with respect to the axial shaft, and
not being held in an axially-fixed position with respect to the proximal and distal bearings.

In some applications, the blood pump does not include any thrust bearing configured to be disposed within the subject's body. In some applications, wherein the blood pump further includes one or more thrust bearings configured to be disposed outside the subject's body, and wherein opposition to thrust generated by the rotation of the impeller is provided solely by the one or more thrust bearings disposed outside the subject's body.

In some applications, the apparatus further includes:
a sensor configured to detect an indication of axial motion of the impeller, and to generate a sensor signal in response thereto; and
a computer processor configured to receive the sensor signal and to generate an output in response thereto.

In some applications, the computer processor is configured to generate an output indicating a cardiac cycle of the subject, in response to receiving the sensor signal. In some applications, the computer processor is configured to determine left-ventricular pressure of the subject, at least partially based upon the sensor signal. In some applications, the computer processor is configured to change a rate of rotation of the impeller, at least partially based upon the sensor signal.

In some applications, the computer processor is configured:
to determine left-ventricular pressure of the subject, at least partially based upon the sensor signal, and
to change a rate of rotation of the impeller, at least partially based upon the determined left-ventricular pressure.

In some applications, the computer processor is configured to reduce the rate of rotation of the impeller, in response to determining that the subject's left-ventricular pressure has decreased.

In some applications, the apparatus further includes:
a magnet, the impeller being coupled to the magnet such that axial motion of the impeller causes the magnet to undergo axial motion;
a sensor configured to detect magnetic flux generated by the magnet, and to generate a sensor signal in response thereto; and
a computer processor configured to receive the sensor signal and to generate an output in response thereto.

In some applications, the computer processor is configured to generate an output indicating a cardiac cycle of the subject, in response to receiving the sensor signal. In some applications, the computer processor is configured to determine left-ventricular pressure of the subject, at least partially based upon the sensor signal. In some applications, the computer processor is configured to change a rate of rotation of the impeller, at least partially based upon the sensor signal.

In some applications, the computer processor is configured:
to determine left-ventricular pressure of the subject, at least partially based upon the sensor signal, and to change a rate of rotation of the impeller, at least partially based upon the determined left-ventricular pressure.

In some applications, the computer processor is configured to reduce the rate of rotation of the impeller, in response to determining that the subject's left-ventricular pressure has decreased.

In some applications, the impeller is configured to pump blood from a first location within the subject's body to a second location within the subject's body, and the impeller is configured to undergo axial back-and-forth motion with respect to the frame, in response to cyclical changes in a pressure difference between the first location and the second location. In some applications, the impeller is configured to pump blood from a left ventricle of the subject to an aorta of the subject, and the impeller is configured to undergo axial back-and-forth motion with respect to the frame, in response to cyclical changes in a pressure difference between the left ventricle and the aorta. In some applications, the impeller is configured to pump blood from a right ventricle of the subject to a pulmonary artery of the subject, and the impeller is configured to undergo axial back-and-forth motion with respect to the frame, in response to cyclical changes in a pressure difference between the right ventricle and the pulmonary artery. In some applications, the impeller is configured to pump blood from a right atrium of the subject to a right ventricle of the subject, and the impeller is configured to undergo axial back-and-forth motion with respect to the frame, in response to cyclical changes in a pressure difference between the right atrium and the right ventricle. In some applications, the impeller is configured to pump blood from a vena cava of the subject to a right ventricle of the subject, and the impeller is configured to undergo axial back-and-forth motion with respect to the frame, in response to cyclical changes in a pressure difference between the vena cava and the right ventricle. In some applications, the impeller is configured to pump blood from a right atrium of the subject to a pulmonary artery of the subject, and the impeller is configured to undergo axial back-and-forth motion with respect to the frame, in response to cyclical changes in a pressure difference between the right atrium and the pulmonary artery. In some applications, the impeller is configured to pump blood from a vena cava of the subject to a pulmonary artery of the subject, and the impeller is configured to undergo axial back-and-forth motion with respect to the frame, in response to cyclical changes in a pressure difference between the vena cava and the pulmonary artery.

In some applications, the apparatus further includes:
a motor configured to drive the impeller to pump blood through the subject's body, by rotating the impeller in a given direction of rotation; and
a drive cable configured to extend from outside a body of the subject to the axial shaft, the drive cable being configured to impart rotational motion from the motor to the impeller by rotating, at least a portion of the drive cable including a plurality of wires disposed in a coiled configuration that is such that, in response to the drive cable rotating in the given direction of rotation, the plurality of wires disposed in the coiled configuration at least partially unwind, such that the portion of the drive cable shortens axially.

In some applications, the impeller is coupled to the axial shaft such that the impeller causes the axial shaft to undergo axial back-and-forth motion with respect to the proximal and distal bearings of the frame. In some applications, the axial shaft is configured to clean interfaces between the axial shaft and the proximal and distal bearings of the frame, by undergoing the axial back-and-forth motion with respect to the proximal and distal bearings of the frame. In some applications, the axial shaft is configured to reduce a build-up of heat at interfaces between the axial shaft and the proximal and distal bearings of the frame, by undergoing the axial back-and-forth motion with respect to the proximal and distal bearings of the frame, relative to if the axial shaft did not undergo the axial back-and-forth motion with respect to the proximal and distal bearings of the frame.

There is further provided, in accordance with some applications of the present invention, apparatus including:
a blood pump including:
an impeller configured to be placed inside a body of a subject, and configured to pump blood through the subject's body;
a frame configured to be disposed around the impeller, the blood pump not including any thrust bearing configured to be disposed within the subject's body.

In some applications, the blood pump further includes one or more thrust bearings configured to be disposed outside the subject's body, and opposition to thrust generated by the rotation of the impeller is provided solely by the one or more thrust bearings disposed outside the subject's body.

In some applications, the apparatus further includes:
a sensor configured to detect an indication of axial motion of the impeller, and to generate a sensor signal in response thereto; and
a computer processor configured to receive the sensor signal and to generate an output in response thereto.

In some applications, the computer processor is configured to generate an output indicating a cardiac cycle of the subject, in response to receiving the sensor signal. In some applications, the computer processor is configured to determine left-ventricular pressure of the subject, at least partially based upon the sensor signal. In some applications, the computer processor is configured to change a rate of rotation of the impeller, at least partially based upon the sensor signal.

In some applications, the computer processor is configured:
to determine left-ventricular pressure of the subject, at least partially based upon the sensor signal, and
to change a rate of rotation of the impeller, at least partially based upon the determined left-ventricular pressure.

In some applications, the computer processor is configured to reduce the rate of rotation of the impeller, in response to determining that the subject's left-ventricular pressure has decreased.

In some applications, the apparatus further includes:
a magnet, the impeller being coupled to the magnet such that axial motion of the impeller causes the magnet to undergo axial motion;
a sensor configured to detect magnetic flux generated by the magnet, and to generate a sensor signal in response thereto; and
a computer processor configured to receive the sensor signal and to generate an output in response thereto.

In some applications, the computer processor is configured to generate an output indicating a cardiac cycle of the subject, in response to receiving the sensor signal. In some applications, the computer processor is configured to determine left-ventricular pressure of the subject, at least partially based upon the sensor signal. In some applications, the computer processor is configured to change a rate of rotation of the impeller, at least partially based upon the sensor signal.

In some applications, the computer processor is configured:
to determine left-ventricular pressure of the subject, at least partially based upon the sensor signal, and
to change a rate of rotation of the impeller, at least partially based upon the determined left-ventricular pressure.

In some applications, the computer processor is configured to reduce the rate of rotation of the impeller, in response to determining that the subject's left-ventricular pressure has decreased.

In some applications, the impeller is configured to pump blood from a first location within the subject's body to a second location within the subject's body, and the impeller is configured to undergo axial back-and-forth motion with respect to the frame, in response to cyclical changes in a pressure difference between the first location and the second location. In some applications, the impeller is configured to pump blood from a left ventricle of the subject to an aorta of the subject, and the impeller is configured to undergo axial back-and-forth motion with respect to the frame, in response to cyclical changes in a pressure difference between the left ventricle and the aorta. In some applications, the impeller is configured to pump blood from a right ventricle of the subject to a pulmonary artery of the subject, and the impeller is configured to undergo axial back-and-forth motion with respect to the frame, in response to cyclical changes in a pressure difference between the right ventricle and the pulmonary artery. In some applications, the impeller is configured to pump blood from a right atrium of the subject to a right ventricle of the subject, and the impeller is configured to undergo axial back-and-forth motion with respect to the frame, in response to cyclical changes in a pressure difference between the right atrium and the right ventricle. In some applications, the impeller is configured to pump blood from a vena cava of the subject to a right ventricle of the subject, and the impeller is configured to undergo axial back-and-forth motion with respect to the frame, in response to cyclical changes in a pressure difference between the vena cava and the right ventricle. In some applications, the impeller is configured to pump blood from a right atrium of the subject to a pulmonary artery of the subject, and the impeller is configured to undergo axial back-and-forth motion with respect to the frame, in response to cyclical changes in a pressure difference between the right atrium and the pulmonary artery. In some applications, the impeller is configured to pump blood from a vena cava of the subject to a pulmonary artery of the subject, and the impeller is configured to undergo axial back-and-forth motion with respect to the frame, in response to cyclical changes in a pressure difference between the vena cava and the pulmonary artery.

In some applications, the apparatus further includes:
a motor configured to drive the impeller to pump blood through the subject's body, by rotating the impeller in a given direction of rotation;
an axial shaft, the impeller being coupled to the axial shaft; and
a drive cable configured to extend from outside a body of the subject to the axial shaft, the drive cable being configured to impart rotational motion from the motor to the impeller by rotating, at least a portion of the drive cable including a plurality of wires disposed in a coiled configuration that is such that, in response to the drive cable rotating in the given direction of rotation, the plurality of wires disposed in the coiled configuration at least partially unwind, such that the portion of the drive cable shortens axially.

In some applications:
the impeller includes proximal and distal bushings;
the frame includes proximal and distal bearings;
the apparatus further includes an axial shaft that:
passes through the proximal and distal bearings defined by the frame and the proximal and distal bushings of the impeller,
is coupled to at least one of the proximal and distal bushings of the impeller, such that the at least one bushing is held in an axially-fixed position with respect to the axial shaft,
is not held in an axially-fixed position with respect to the proximal and distal bearings,
such that the impeller causes the axial shaft to undergo axial back-and-forth motion with respect to the proximal and distal bearings of the frame.

In some applications, the axial shaft is configured to clean interfaces between the axial shaft and the proximal and distal bearings of the frame, by undergoing the axial back-and-forth motion with respect to the proximal and distal bearings of the frame. In some applications, the axial shaft is configured to reduce a build-up of heat at interfaces between the axial shaft and the proximal and distal bearings of the frame, by undergoing the axial back-and-forth motion with respect to the proximal and distal bearings of the frame, relative to if the axial shaft did not undergo the axial back-and-forth motion with respect to the proximal and distal bearings of the frame.

There is further provided, in accordance with some applications of the present invention, the following inventive concepts:

Inventive concept 1. Apparatus comprising:
an impeller comprising:
at least one helical elongate element;
a spring that is disposed inside of the helical elongate element, and along an axis around which the helical elongate element winds;
a film of material supported between the helical elongate element and the spring; and
at least one flexible elongate element extending from the spring to the helical elongate element and configured to maintain the helical elongate element within a given distance from the spring, the at least one flexible elongate element being selected from the group consisting of: a string and a wire.

Inventive concept 2. The apparatus according to inventive concept 1, wherein the impeller is configured such that in a non-radially-constrained configuration of the impeller, an outer diameter of the impeller at a location at which the outer diameter is at its maximum is less than 8 mm.

Inventive concept 3. The apparatus according to inventive concept 1, wherein the at least one helical elongate element comprises a plurality of helical elongate elements, and wherein the at least one flexible elongate element extends from the spring to each of the helical elongate elements.

Inventive concept 4. The apparatus according to any one of inventive concepts 1-3, wherein the impeller is configured to pump blood through a body of a subject.

Inventive concept 5. The apparatus according to inventive concept 4, wherein the impeller is configured to be placed in a blood vessel of the subject.

Inventive concept 6. The apparatus according to inventive concept 4, wherein the impeller is configured to be placed in a cardiac chamber of the subject.

Inventive concept 7. The apparatus according to inventive concept 4, wherein the impeller is configured to pump blood from a left ventricle of a subject to an aorta of the subject.

Inventive concept 8. The apparatus according to inventive concept 4, wherein the impeller is configured to pump blood from a right ventricle of a subject to a pulmonary artery of the subject.

Inventive concept 9. A method comprising:
 placing into a body of a subject an impeller that includes:
  at least one helical elongate element;
  a spring that is disposed inside of the helical elongate element, and along an axis around which the helical elongate element winds;
  a film of material supported between the helical elongate element and the spring; and
  at least one flexible elongate element extending from the spring to the helical elongate element selected from the group consisting of: a string and a wire; and
 pumping blood through the subject's body by rotating the impeller, the flexible elongate element maintaining the helical elongate element within a given distance from the spring, during the rotation of the impeller.

Inventive concept 10. Apparatus comprising:
 a blood pump comprising:
  an impeller configured to be placed inside a cardiac chamber of a subject;
  a frame configured to be disposed around the impeller; and
  a motor configured to drive the impeller to pump blood from the cardiac chamber to a blood vessel of the subject, by rotating the impeller,
  the impeller being configured to undergo axial motion with respect to the frame, in response to cyclical changes in a pressure difference between the cardiac chamber and the blood vessel.

Inventive concept 11. A method comprising:
 placing an impeller of a blood pump inside a cardiac chamber of a subject, with a frame disposed around the impeller; and
 driving the impeller to pump blood from the cardiac chamber to a blood vessel of the subject, by rotating the impeller,
 placement of the impeller inside the cardiac chamber being such that the impeller is allowed to undergo axial motion with respect to the frame, in response to cyclical changes in a pressure difference between the cardiac chamber and the blood vessel.

Inventive concept 12. Apparatus comprising:
 a blood pump comprising:
  an impeller configured to be placed inside a first blood vessel of a subject;
  a frame configured to be disposed around the impeller; and
  a motor configured to drive the impeller to pump blood from the first blood vessel to a second blood vessel of the subject, by rotating the impeller,
  the impeller being configured to undergo axial motion with respect to the frame, in response to cyclical changes in a pressure difference between the first blood vessel and the second blood vessel.

Inventive concept 13. A method comprising:
 placing an impeller of a blood pump inside a first blood vessel of a subject, with a frame disposed around the impeller; and
 driving the impeller to pump blood from the first blood vessel to a second blood vessel of the subject, by rotating the impeller,
 placement of the impeller inside the first blood vessel being such that the impeller is allowed to undergo axial motion with respect to the frame, in response to cyclical changes in a pressure difference between the cardiac chamber and the blood vessel.

Inventive concept 14. Apparatus comprising:
 a blood pump comprising:
  an impeller configured to be placed inside a body of a subject, and configured to rotate such as to pump blood through the subject's body;
  a frame configured to be disposed around the impeller; and
  one or more thrust bearings configured to be disposed outside the subject's body, wherein opposition to thrust generated by the rotation of the impeller is provided solely by the one or more thrust bearings disposed outside the subject's body.

Inventive concept 15. A method comprising:
 placing an impeller of a blood pump inside a body of a subject, with a frame disposed around the impeller; and
 driving the impeller to pump blood through the subject's body, by rotating the impeller, opposition to thrust generated by the rotation of the impeller being provided solely by one or more thrust bearings disposed outside the subject's body.

Inventive concept 16. Apparatus comprising:
 a blood-pump tube;
 a blood pump configured to be disposed within the blood-pump tube, and to pump blood through the blood-pump tube;
 at least one blood-pressure-measurement tube that defines an opening at a distal end thereof, and that is configured to extend to at least an outer surface of the blood-pump tube, such that the opening at the distal end of the blood-pressure-measurement tube is in direct fluid communication with a bloodstream of the subject outside the blood-pump tube; and
 at least one pressure sensor configured to measure pressure of the bloodstream of the subject outside the blood-pump tube by measuring pressure of blood within the blood-pressure-measurement tube.

Inventive concept 17. The apparatus according to inventive concept 16, wherein the blood pump comprises an impeller that is configured to pump blood through the blood-pump tube, by rotating.

Inventive concept 18. The apparatus according to inventive concept 16, wherein the blood-pressure-measurement tube is configured to pass along an outer surface of the blood-pump tube from the proximal end of the blood-pump tube until the opening at the distal end of the blood-pressure-measurement tube.

Inventive concept 19. The apparatus according to inventive concept 16, further comprising at least one computer processor that is configured to receive an indication of the blood pressure measured within the blood-pressure-measurement tube and to control the pumping of blood by the blood pump in response to the blood pressure measured within the blood-pump tube.

Inventive concept 20. The apparatus according to any one of inventive concepts 16-19, wherein the at least one blood-pressure measurement tube comprises at least one left-ventricular blood-pressure measurement tube that is configured to extend to the outer surface of the blood-pump tube at a location along the tube that is configured to be within the subject's left ventricle proximal to the blood pump, and wherein the pressure sensor is configured to measure left-ventricular pressure of the subject by measuring pressure of blood within the left-ventricular blood-pressure-measurement tube.

Inventive concept 21. The apparatus according to inventive concept 20, wherein the at least one blood-pressure measurement tube comprises two or more left-ventricular blood-pressure measurement tubes that are configured to extend to the outer surface of the blood-pump tube at locations along the blood-pump tube that are configured to be within the subject's left ventricle proximal to the blood pump, and wherein the at least one pressure sensor is configured to measure left-ventricular pressure of the subject by measuring pressure of blood within at least one of the left-ventricular blood-pressure-measurement tubes.

Inventive concept 22. The apparatus according to inventive concept 21,
wherein the at least one pressure sensor is configured to measure pressure of blood within each of the two or more left-ventricular blood-pressure-measurement tubes,
the apparatus further comprising at least one computer processor that is configured:
to receive an indication of the blood pressure measured within each of the two or more left-ventricular blood-pressure-measurement tubes,
in response thereto, to determine that the opening of one of the two or more left-ventricular blood-pressure-measurement tubes is occluded, and
in response thereto, to determine left-ventricular pressure of the subject, based upon the blood pressure measured within a different one of the two or more left-ventricular blood-pressure-measurement tubes.

Inventive concept 23. The apparatus according to inventive concept 20, wherein the at least one blood-pressure measurement tube further comprises at least one aortic blood-pressure measurement tube that is configured to extend to the outer surface of the blood-pump tube at a location along the blood-pump tube that is configured to be within the subject's aorta, and wherein the pressure sensor is configured to measure aortic pressure of the subject by measuring pressure of blood within the aortic blood-pressure-measurement tube.

Inventive concept 24. The apparatus according to inventive concept 23, wherein the at least one aortic blood-pressure measurement tube comprises two or more aortic blood-pressure measurement tubes that are configured to extend to the outer surface of the blood-pump tube at locations along the blood-pump tube that are configured to be within the subject's aorta, and wherein the at least one pressure sensor is configured to measure aortic pressure of the subject by measuring pressure of blood within at least one of the aortic blood-pressure-measurement tubes.

Inventive concept 25. The apparatus according to any one of inventive concepts 16-19, wherein the at least one blood-pressure measurement tube comprises at least one aortic blood-pressure measurement tube that is configured to extend to the outer surface of the blood-pump tube at a location along the blood-pump tube that is configured to be within the subject's aorta, and wherein the pressure sensor is configured to measure aortic pressure of the subject by measuring pressure of blood within the aortic blood-pressure-measurement tube.

Inventive concept 26. The apparatus according to inventive concept 25, wherein the at least one aortic blood-pressure measurement tube comprises two or more aortic blood-pressure measurement tubes that are configured to extend to the outer surface of the blood-pump tube at locations along the blood-pump tube that are configured to be within the subject's aorta, and wherein the at least one pressure sensor is configured to measure aortic pressure of the subject by measuring pressure of blood within at least one of the aortic blood-pressure-measurement tubes.

Inventive concept 27. The apparatus according to inventive concept 26,
wherein the at least one pressure sensor is configured to measure pressure of blood within each of the two or more aortic blood-pressure-measurement tubes,
the apparatus further comprising at least one computer processor that is configured:
to receive an indication of the blood pressure measured within each of the two or more aortic blood-pressure-measurement tubes,
in response thereto, to determine that the opening of one of the two or more aortic blood-pressure-measurement tubes is occluded, and
in response thereto, to determine aortic pressure of the subject, based upon the blood pressure measured within a different one of the two or more aortic blood-pressure-measurement tubes.

Inventive concept 28. The apparatus according to any one of inventive concepts 16-19, wherein the blood-pressure-measurement tube is configured to extend from outside a body of the subject to the opening at the distal end, and wherein the at least one pressure sensor is configured to be disposed outside the subject's body.

Inventive concept 29. The apparatus according to inventive concept 28, wherein the blood pump comprises an impeller disposed upon an axial shaft, the impeller being configured to pump blood from the left ventricle to the aorta by rotating, wherein the apparatus further comprises:
a motor disposed outside the subject's body, and configured to drive the impeller to rotate;
a drive cable extending from outside the subject's body to the axial shaft, and configured to impart rotational motion from the motor to the impeller, by rotating; and
an outer tube configured to extend from outside the subject's body to within the blood-pump tube,
wherein the drive cable and the blood-pressure-measurement tube are configured to be disposed within the outer tube.

Inventive concept 30. The apparatus according to inventive concept 29,
wherein the at least one blood-pressure measurement tube comprises at least one left-ventricular blood-pressure measurement tube that is configured to extend to the outer surface of the blood-pump tube at a location along the blood-pump tube that is configured to be within the subject's left ventricle proximal to the blood pump, and wherein the at least one pressure sensor is configured to measure left-ventricular pressure of the subject by measuring pressure of blood within the left-ventricular blood-pressure-measurement tube;
the apparatus further comprising an aortic blood-pressure-measurement tube that defines an opening at a distal end thereof, and that is configured to extend from outside the subject's body to an outer surface of the outer tube within an aorta of the subject, such that the opening at the distal end of the blood-pressure-measurement tube is in direct fluid communication with an aortic bloodstream of the subject;
wherein the at least one pressure sensor is further configured to measure aortic pressure of the subject by measuring pressure of blood within the aortic blood-pressure-measurement tube.

Inventive concept 31. The apparatus according to inventive concept 29, wherein the at least one blood-pressure measurement tube comprises at least one left-ventricular blood-pressure measurement tube that is configured to extend to the outer surface of the blood-pump tube at a location along the blood-pump tube that is configured to be within the subject's left ventricle proximal to the blood pump, and wherein the at least one pressure sensor is configured to measure left-ventricular pressure of the subject by measuring pressure of blood within the left-ventricular blood-pressure-measurement tube;

the apparatus further comprising an aortic blood-pressure-measurement tube that defines an opening at a distal end thereof, and that is configured to extend from outside the subject's body to a portion of an outer surface of the outer tube that is disposed within the blood-pump tube, such that the opening at the distal end of the blood-pressure-measurement tube is in direct fluid communication with an aortic bloodstream of the subject;

wherein the at least one pressure sensor is further configured to measure aortic pressure of the subject by measuring pressure of blood within the aortic blood-pressure-measurement tube.

Inventive concept 32. The apparatus according to inventive concept 29, wherein the outer tube defines a groove in a portion of an outer surface of the outer tube that is configured to be disposed within the blood-pump tube, and wherein, during insertion of the ventricular assist device into the subject's body, a portion of the blood-pressure-measurement tube that is configured to extend from within the blood-pump tube to the outer surface of the blood-pump tube is configured to be disposed within the groove, such that the portion of the blood-pressure-measurement tube does not protrude from the outer surface of the outer tube.

Inventive concept 33. The apparatus according to inventive concept 28, wherein a diameter of the blood-pressure-measurement tube at least within a distal portion of the blood-pressure-measurement tube is less than 0.5 mm.

Inventive concept 34. The apparatus according to inventive concept 33, wherein the diameter of the blood-pressure-measurement tube at least within the distal portion of the blood-pressure-measurement tube is more than 0.2 mm.

Inventive concept 35. A method comprising:
placing into a body of a subject:
a blood-pump tube,
a blood pump disposed within the blood-pump tube, and
at least one blood-pressure-measurement tube that defines an opening at a distal end thereof, and that extends to at least an outer surface of the blood-pump tube, such that the opening at the distal end of the blood-pressure-measurement tube is in direct fluid communication with a bloodstream of the subject outside the blood-pump tube;
pumping blood through the blood-pump tube, using the blood pump; and
measuring pressure of the bloodstream of the subject outside the blood-pump tube by measuring pressure of blood within the blood-pressure-measurement tube.

Inventive concept 36. Apparatus comprising:
a blood pump comprising:
a tube;
an impeller configured to be disposed within the tube and configured to rotate, such as to pump blood through the tube;
a frame disposed around the impeller; and
a stator configured to reduce rotational flow components from blood flow generated by rotation of the impeller, the stator comprising:
a plurality of struts that are integral with the frame and that are curved; and
a flexible material coupled to the curved struts such as to form a plurality of curved projections.

Inventive concept 37. The apparatus according to inventive concept 36, wherein the curvature of the curved projections opposes the direction of rotation of the impeller.

Inventive concept 38. The apparatus according to inventive concept 36, wherein the curvature of the curved projections is such that, from distal ends of the curved projections to proximal ends of the curved projections, the curved projections become progressively closer to being parallel with a longitudinal axis of the frame.

Inventive concept 39. The apparatus according to inventive concept 36, wherein the flexible material is shaped to define a lumen therethrough.

Inventive concept 40. A method comprising:
placing a blood pump into a subject's body, the blood pump including:
a tube,
an impeller configured to be disposed within the tube,
a frame disposed around the impeller, and
a stator that includes a plurality of struts that are integral with the frame and that are curved, and a flexible material coupled to the curved struts such as to form a plurality of curved projections; and
pumping blood through the tube using the impeller, the stator reducing rotational flow components from blood flow generated by rotation of the impeller.

Inventive concept 41. Apparatus comprising:
a ventricular assist device comprising:
an axial shaft;
an impeller disposed on the axial shaft and configured to be placed in a left ventricle of a subject;
a motor configured to be disposed outside a body of the subject, and configured to drive the impeller to pump blood from the left ventricle to an aorta of the subject by rotating the impeller;
a drive cable configured to extend from outside the subject's body to the axial shaft, the drive cable being configured to impart rotational motion from the motor to the impeller by rotating, the drive cable comprising a first portion configured to be disposed at least partially within an aortic arch of the subject, and a second portion configured to be disposed at least partially within a descending aorta of the subject,
the first portion of the drive cable comprising a first number of wires disposed in a coiled configuration, and the second portion of the drive cable comprising a second number of wires disposed in a coiled configuration, the first number being lower than the second number.

Inventive concept 42. The apparatus according to inventive concept 41, wherein a length of the first portion of the drive cable is between 20 cm and 40 cm.

Inventive concept 43. The apparatus according to inventive concept 41, wherein a length of the second portion of the drive cable is between 60 cm and 100 cm.

Inventive concept 44. The apparatus according to inventive concept 41, wherein the first portion of the drive cable comprises between 4 and 8 wires disposed in the coiled configuration, and the second portion of the drive cable comprises between 8 and 12 wires disposed in the coiled configuration.

Inventive concept 45. Apparatus comprising:
  a blood pump comprising:
    an axial shaft;
    an impeller disposed on the axial shaft;
    a motor configured to be disposed outside a body of the subject, and configured to drive the impeller to pump blood through the subject's body by rotating the impeller;
    a drive cable configured to extend from outside the subject's body to the axial shaft, the drive cable being configured to impart rotational motion from the motor to the impeller by rotating, the drive cable comprising a first portion configured to be disposed at least partially within a curved portion of vasculature of the subject, and a second portion configured to be disposed at least partially within a straight portion of vasculature of the subject,
    the first portion of the drive cable comprising a first number of wires disposed in a coiled configuration, and the second portion of the drive cable comprising a second number of wires disposed in a coiled configuration, the first number being lower than the second number.

Inventive concept 46. Apparatus comprising:
  a blood pump comprising:
    an axial shaft;
    an impeller disposed on the axial shaft;
    a motor configured to be disposed outside a body of the subject, and configured to drive the impeller to pump blood from a distal end of the impeller to a proximal end of the impeller, by rotating the impeller in a given direction of rotation;
    a drive cable configured to extend from outside the subject's body to the axial shaft, the drive cable being configured to impart rotational motion from the motor to the impeller by rotating,
      at least a portion of the drive cable comprising a plurality of wires disposed in a coiled configuration that is such that, in response to the drive cable rotating in the given direction of rotation, the plurality of wires disposed in the coiled configuration at least partially unwind, such that the portion of the drive cable shortens axially.

Inventive concept 47. The apparatus according to inventive concept 46, wherein the impeller is configured to pump blood from a first location to a second location, and wherein the impeller is configured to undergo axial back-and-forth motion, in response to cyclical changes in a pressure difference between the first location and the second location.

Inventive concept 48. A method comprising:
  placing a blood pump into a body of a subject, the blood pump including:
    an axial shaft,
    an impeller disposed on the axial shaft, and
    a drive cable extending from outside the subject's body to the axial shaft; and
  driving the impeller to pump blood from a distal end of the impeller to a proximal end of the impeller by imparting rotational motion the impeller via the drive cable, at least a portion of the drive cable comprising a plurality of wires disposed in a coiled configuration that is such that, in response to the drive cable rotating in the given direction of rotation, the plurality of wires disposed in the coiled configuration at least partially unwind, such that the portion of the drive cable shortens axially.

Inventive concept 49. Apparatus comprising:
  a blood pump comprising:
    an axial shaft;
    an impeller disposed on the axial shaft;
    a motor configured to be disposed outside a body of the subject, and configured to drive the impeller to pump blood in a proximal direction by rotating the impeller in a given direction of rotation;
    a drive cable configured to extend a proximal end of the drive cable disposed outside the subject's body to a distal end of the drive cable, which is coupled to the axial shaft, the drive cable being configured to impart rotational motion from the motor to the impeller by rotating;
    an outer tube disposed around the drive cable; and
    fluid disposed between the outer tube and the drive cable,
    at least a portion of the drive cable comprising a plurality of wires disposed in a coiled configuration that is such that in response to the drive cable rotating in the given direction of rotation, the plurality of wires are configured to pump the fluid toward the proximal end of the drive cable.

Inventive concept 50. A method comprising:
  placing a blood pump into a body of a subject, the blood pump including:
    an axial shaft,
    an impeller disposed on the axial shaft,
    a drive cable extending from outside the subject's body to the axial shaft,
    an outer tube disposed around the drive cable, and
    a fluid disposed between the drive cable and the outer tube; and
  driving the impeller to pump blood from a distal end of the impeller to a proximal end of the impeller by imparting rotational motion the impeller via the drive cable, at least a portion of the drive cable comprising a plurality of wires disposed in a coiled configuration that is such that, in response to the drive cable rotating in the given direction of rotation, the plurality of wires are configured to pump the fluid toward the proximal end of the drive cable.

Inventive concept 51. Apparatus comprising:
  a blood pump comprising:
    an impeller;
    a motor configured to drive the impeller to pump blood by rotating the impeller, the impeller being configured to undergo axial motion, in response to changes in a pressure difference against which the impeller is pumping the blood;
    a magnet, the impeller being coupled to the magnet such that axial motion of the impeller causes the magnet to undergo axial motion;
    a sensor configured to detect magnetic flux generated by the magnet, and to generate a sensor signal in response thereto; and
    a computer processor configured to receive the sensor signal and to generate an output in response thereto.

Inventive concept 52. The apparatus according to inventive concept 51, wherein the computer processor is configured to generate an output indicating a cardiac cycle of the subject, in response to receiving the sensor signal.

Inventive concept 53. The apparatus according to inventive concept 51, wherein the computer processor is configured to determine left-ventricular pressure of the subject, at least partially based upon the sensor signal.

Inventive concept 54. The apparatus according to any one of inventive concepts 51-53, wherein the computer processor is configured to change a rate of rotation of the impeller, at least partially based upon the sensor signal.

Inventive concept 55. The apparatus according to inventive concept 54, wherein the computer processor is configured:
  to determine left-ventricular pressure of the subject, at least partially based upon the sensor signal, and
  to change a rate of rotation of the impeller, at least partially based upon the determined left-ventricular pressure.

Inventive concept 56. The apparatus according to inventive concept 55, wherein the computer processor is configured to reduce the rate of rotation of the impeller, in response to determining that the subject's left-ventricular pressure has decreased.

Inventive concept 57. Apparatus comprising:
  a blood pump comprising:
    an impeller;
    a motor configured to drive the impeller to pump blood by rotating the impeller, the impeller being configured to undergo axial motion, in response to changes in a pressure difference against which the impeller is pumping the blood;
    a sensor configured to detect an indication of the axial motion of the impeller, and to generate a sensor signal in response thereto; and
    a computer processor configured to receive the sensor signal and to generate an output in response thereto.

Inventive concept 58. A method comprising:
  placing a blood pump inside a body of a subject, the blood pump including an impeller;
  driving the impeller to pump blood by rotating the impeller, the impeller being configured to undergo axial motion, in response to changes in a pressure difference against which the impeller is pumping the blood;
  detecting an indication of the axial motion of the impeller, and generating a sensor signal in response thereto; and
  receiving the sensor signal, and generating an output in response thereto.

Inventive concept 59. Apparatus comprising:
  a blood pump comprising:
    an impeller;
    a frame,
      the impeller and the frame being configured to be inserted into a body of a subject, such that, within the subject's body, the frame is disposed around the impeller; and
    a computer processor configured to drive a motor unit to, simultaneously, (a) drive the impeller to pump blood through the subject's body, by driving the impeller to rotate, and (b) drive the impeller to move axially within the frame in a back-and-forth motion.

Inventive concept 60. A method comprising:
  placing, into a body of a subject, a blood pump that includes an impeller and a frame, such that the frame is disposed around the impeller; and
  simultaneously:
    driving the impeller to pump blood through the subject's body, by driving the impeller to rotate; and
    driving the impeller to move axially within the frame in a back-and-forth motion.

Inventive concept 61. Apparatus comprising:
  a blood pump comprising:
    an axial shaft;
    an impeller disposed on the axial shaft and configured to be placed in a left ventricle of a subject;
    a motor configured to be disposed outside a body of the subject, and configured to drive the impeller to rotate;
    a drive cable configured to extend from outside of the subject's body to the axial shaft, via an aortic arch of the subject, the drive cable being configured to impart rotational motion from the motor to the impeller, by rotating;
    a tube, within which the drive cable is configured to be disposed during rotation of the drive cable, the tube being configured to remain stationary during rotation of the drive cable; and
    a plurality of ball bearings configured to be disposed between the drive cable and the tube, such as to reduce friction between the drive cable and the tube during movement of the drive cable with respect to the tube.

Inventive concept 62. The apparatus according to inventive concept 61, wherein the ball bearings are configured to be disposed between the drive cable and the tube, at least at portions of the drive cable and the tube that are configured to be disposed within the subject's aortic arch, during the rotation of the impeller.

Inventive concept 63. Apparatus comprising:
  a blood pump comprising:
    an axial shaft;
    an impeller disposed on the axial shaft and configured to be placed inside a body of a subject;
    a motor configured to be disposed outside the subject's body;
    a drive cable configured to extend from outside the subject's body to the axial shaft;
    exactly two driving magnets disposed in a driving magnet housing, which is coupled to the motor; and
    a driven magnet coupled to the drive cable and disposed between the driving magnets such there is axial overlap between the driving magnets and the driven magnets, the driven magnet defining a single North pole and a single South pole that are divided along an axial length of the driven magnet, the motor being configured to impart rotational motion to the impeller by rotating the drive cable by rotating the driven magnet, by rotating the driving magnet housing.

Inventive concept 64. A method comprising:
  placing, into a subject's body, a blood pump that includes:
    an axial shaft,
    an impeller disposed on the axial shaft, and
    a drive cable extending from outside the subject's body to the axial shaft; and driving the impeller to rotate by:
      using a motor to rotate exactly two driving magnets disposed in a driving magnet housing, which is coupled to the motor,
      the driving magnets being configured to thereby drive a driven magnet to rotate, the driven magnet being coupled to the drive cable and disposed between the driving magnets such there is axial overlap between the driving magnets and the driven magnets, the driven magnet defining a single North pole and a single South pole that are divided along an axial length of the driven magnet.

Inventive concept 65. Apparatus comprising:
  a blood pump comprising:
    an axial shaft;
    an impeller disposed on the axial shaft and configured to be placed inside a body of a subject;
    a motor configured to be disposed outside the subject's body;
    a drive cable configured to extend from outside the subject's body to the axial shaft;
    exactly two driven magnets disposed in a driven magnet housing, which is coupled to the drive cable; and
    a drive magnet coupled to the motor and disposed between the driven magnets such there is axial overlap between the driven magnets and the driving magnet, the driving magnet defining a single North pole and a single South pole that are divided along an axial length of the driving magnet, the motor being configured to impart rotational motion to the impeller by rotating the drive cable, by rotating the driven magnets, by rotating the driving magnet.

Inventive concept 66. A method comprising:
placing, into a subject's body, a blood pump that includes:
an axial shaft,
an impeller disposed on the axial shaft, and
a drive cable extending from outside the subject's body to the axial shaft; and driving the impeller to rotate by:
using a motor to rotate a drive magnet coupled to the motor, the drive magnet defining a single North pole and a single South pole that are divided along an axial length of the driving magnet,
the driving magnet being configured to thereby drive driven magnets to rotate, the driven magnets comprising exactly two driven magnets disposed in a driven magnet housing, the driven magnet housing being coupled to the drive cable and being disposed around the drive magnet.

Inventive concept 67. Apparatus comprising:
a blood pump comprising:
an axial shaft;
an impeller disposed on the axial shaft and configured to be placed inside a body of a subject;
a motor configured to be disposed outside the subject's body, and configured to drive the impeller to pump blood by rotating the impeller in a given direction of rotation;
a drive cable configured to extend from outside the subject's body to the axial shaft, the drive cable being configured to impart rotational motion from the motor to the impeller by rotating, and the drive cable comprising a plurality of wires that are disposed in a coiled configuration and that are coupled to the axial shaft,
the axial shaft defining grooves at an interface between the drive cable and the axial shaft, the grooves being configured such that stress generated by the wires at the interface is spread over radii of the grooves.

Inventive concept 68. Apparatus comprising:
a blood pump comprising:
an axial shaft;
an impeller disposed on the axial shaft and configured to be placed inside a body of a subject;
a motor configured to be disposed outside the subject's body, and configured to drive the impeller to pump blood by rotating the impeller in a given direction of rotation;
a drive cable configured to extend from outside the subject's body to the axial shaft, the drive cable being configured to impart rotational motion from the motor to the impeller by rotating, and the drive cable comprising a plurality of wires that are disposed in a coiled configuration and that are coupled to the axial shaft,
the coiled wires being shaped such that as the coiled wires approach an interface between the drive cable and the axial shaft, a pitch of the wires is increased, such that stress at locations at which the wires of the drive cable are coupled to the axial shaft is reduced, relative to if the pitch of the wires were not increased.

Inventive concept 69. Apparatus comprising:
a blood pump comprising:
an axial shaft;
an impeller disposed on the axial shaft and configured to be placed inside a body of a subject;
a motor configured to be disposed outside the subject's body, and configured to drive the impeller to pump blood by rotating the impeller in a given direction of rotation;
a drive cable configured to extend from outside the subject's body to the axial shaft, the drive cable being configured to impart rotational motion from the motor to the impeller by rotating,
the drive cable comprising first and second portions, the first portion of the drive cable comprising a first number of wires disposed in a coiled configuration, and the second portion of the drive cable comprising a second number of wires disposed in a coiled configuration, the first number being lower than the second number; and
an interface component, the first and second portions of the drive cable being coupled to each other via the interface component,
the interface component defining grooves at an interface between at least one of the drive cable portions and the interface component, the grooves being configured such that stress generated by the wires at the interface is spread over radii of the grooves.

Inventive concept 70. Apparatus comprising:
a blood pump comprising:
an axial shaft;
an impeller disposed on the axial shaft and configured to be placed inside a body of a subject;
a motor configured to be disposed outside the subject's body, and configured to drive the impeller to pump blood by rotating the impeller in a given direction of rotation;
a drive cable configured to extend from outside the subject's body to the axial shaft, the drive cable being configured to impart rotational motion from the motor to the impeller by rotating,
the drive cable comprising first and second portions, the first portion of the drive cable comprising a first number of wires disposed in a coiled configuration, and the second portion of the drive cable comprising a second number of wires disposed in a coiled configuration, the first number being lower than the second number; and
an interface component, the first and second portions of the drive cable being coupled to each other via the interface component,
the coiled wires of at least one of the portions of the drive cable being shaped such that, as the coiled wires approach the interface component, a pitch of the wires is increased, such that stress at locations at which the wires are coupled to the interface component is reduced relative to if the pitch of the wires were not increased.

Inventive concept 71. Apparatus comprising:
a ventricular assist device comprising:
a tube configured to traverse an aortic valve of a subject, such that a proximal portion of the tube is disposed within an aorta of the subject and a distal portion of the tube is disposed within a left ventricle of the subject, the tube defining one or more blood inlet openings within the distal portion of the tube, and one or more blood outlet openings within the proximal portion of the tube;
a blood pump configured to be disposed within the tube, and to pump blood from the left ventricle into the tube through the one or more blood inlet openings, and out of the tube into the aorta through the one or more blood outlet openings; and a radially-expandable atraumatic distal tip portion configured to be disposed within the subject's left ventricle distally with respect to the one or more blood inlet openings, the distal tip portion being configured to be inserted into the left ventricle in a radially-constrained configuration, and to assume a non-radially-constrained configuration within the subject's left ventricle in which at least a radially-expandable portion of the distal tip portion is radially expanded relative to the radially-constrained configuration of the distal tip portion.

Inventive concept 72. The apparatus according to inventive concept 71, wherein the distal tip portion comprises a braided shape-memory alloy that is at least partially covered with a blood impermeable material.

Inventive concept 73. The apparatus according to inventive concept 71, wherein the distal tip portion is configured such that, in the non-radially-constrained configuration of the distal tip portion, the radially-expandable portion of the distal tip portion separates the one or more blood inlet openings from an interventricular septum within the left ventricle.

Inventive concept 74. The apparatus according to inventive concept 71, wherein the distal tip portion is configured such that, in the non-radially-constrained configuration of the distal tip portion, the radially-expandable portion of the distal tip portion separates the one or more blood inlet openings from chordae tendineae within the left ventricle.

Inventive concept 75. The apparatus according to inventive concept 71, wherein the distal tip portion is configured such that, in the non-radially-constrained configuration of the distal tip portion, the radially-expandable portion of the distal tip portion separates the one or more blood inlet openings from papillary muscles within the left ventricle.

Inventive concept 76. The apparatus according to inventive concept 71, wherein the distal tip portion is configured such that, in the non-radially-constrained configuration of the distal tip portion, the radially-expandable portion of the distal tip portion separates the one or more blood inlet openings from an apex of the left ventricle.

Inventive concept 77. The apparatus according to inventive concept 71, wherein the distal tip portion is configured such that, in the non-radially-constrained configuration of the distal tip portion, the radially-expandable portion of the distal tip portion separates the one or more blood inlet openings from inner structures of the left ventricle in three dimensions.

Inventive concept 78. The apparatus according to inventive concept 71, wherein the distal tip portion is configured such that, in the non-radially-constrained configuration of the distal tip portion, the radially-expandable portion of the distal tip portion directs blood flow from the left ventricle into the one or more blood inlet openings.

Inventive concept 79. The apparatus according to any one of inventive concepts 71-78, wherein:
in the radially-constrained configuration of the distal tip portion, a distal region of the distal tip portion is configured to be least semi-rigid, and is shaped to radially converge along a longitudinal direction toward a distal end of the distal tip portion;
the ventricular assist device is configured to be inserted into the subject's body via a puncture, in the subject's body, and
during the insertion of the ventricular assist device the distal region of the distal tip portion is configured to act as a dilator by dilating the puncture.

Inventive concept 80. The apparatus according to any one of inventive concepts 71-78, wherein the distal tip portion is configured such that in the non-radially-constrained configuration of the distal tip portion, a distal end of the distal tip portion is enveloped within the radially-expandable portion of the distal tip portion.

Inventive concept 81. The apparatus according to inventive concept 80, wherein the distal tip portion is configured to prevent the distal end of the distal tip portion becoming entangled with chordae tendineae of the left ventricle by the distal end of the distal tip portion being enveloped within the radially expanded portion of the distal tip.

Inventive concept 82. The apparatus according to inventive concept 80, wherein the distal tip portion is configured to prevent the distal end of the distal tip portion causing trauma to an internal structure of the left ventricle by the distal end of the distal tip portion being enveloped within the radially-expandable portion of the distal tip portion.

Inventive concept 83. The apparatus according to inventive concept 80, wherein the distal end of the distal tip portion is configured to be enveloped within the radially-expandable portion of the distal tip portion, by the distal end of the distal tip portion inverting.

Inventive concept 84. The apparatus according to inventive concept 80, wherein the distal end of the distal tip portion is configured to be enveloped within the radially-expandable portion of the distal tip portion, by the distal end of the distal tip portion being retracted proximally, such that the distal end is disposed within the radially-expandable portion of the distal tip portion.

Inventive concept 85. Apparatus comprising:
a ventricular assist device configured to be inserted into a subject's body via a puncture, the ventricular assist device comprising:
a tube configured to traverse an aortic valve of a subject, such that a proximal portion of the tube is disposed within an aorta of the subject and a distal portion of the tube is disposed within a left ventricle of the subject, the tube defining one or more blood inlet openings within the distal portion of the tube, and one or more blood outlet openings within the proximal portion of the tube;
a blood pump configured to be disposed within the tube, and to pump blood from the left ventricle into the tube through the one or more blood inlet openings, and out of the tube into the aorta through the one or more blood outlet openings; and
a distal tip portion configured:
to have a radially-constrained configuration in which a distal region of the distal tip portion is at least partially rigid, and is shaped to radially converge along a longitudinal direction toward a distal end of the distal tip portion, the distal region being configured to act as a dilator by dilating the puncture, during insertion of the ventricular assist device into the subject's body, and
to have a non-radially-constrained configuration that the distal tip region is configured to assume within the subject's left ventricle in which the radially-expandable portion of the distal tip portion is configured to be atraumatic and to separate the one or more blood inlet openings from internal structures of the subject's left ventricle.

Inventive concept 86. A method comprising:
   operating a blood pump, the blood pump including:
      an axial shaft,
      an impeller disposed on the axial shaft and disposed in a left ventricle of a subject;
      a motor disposed outside a body of the subject, and configured to drive the impeller to rotate,
      a drive cable extending from outside the subject's body to the axial shaft via an aortic arch of the subject, and configured to impart rotational motion from the motor to the impeller, by rotating, and
      a tube, within which the drive cable is disposed, the tube being configured to remain stationary during rotation of the drive cable; and
   while operating the blood pump, pumping fluid into a space between the drive cable and the tube, such that the fluid fills the space between the drive cable and the tube, but without releasing the fluid into a bloodstream of the subject.

Inventive concept 87. A method comprising:
   operating a blood pump, the blood pump including:
      an axial shaft,
      an impeller disposed on the axial shaft and disposed in a left ventricle of a subject,
      a motor disposed outside a body of the subject, and configured to drive the impeller to rotate,
      a drive cable extending from outside the subject's body to the axial shaft via an aortic arch of the subject, and configured to impart rotational motion from the motor to the impeller, by rotating, and
      a tube, within which the drive cable is disposed, the tube being configured to remain stationary during rotation of the drive cable;
   prior to operating the blood pump, pumping fluid into a space between the drive cable and the tube, such that the fluid fills the space between the drive cable and the tube, but without releasing the fluid into a bloodstream of the subject; and
   leaving the fluid within the space between the drive cable and the tube, during the operation of the blood pump.

Inventive concept 88. Apparatus comprising:
   a left-ventricular assist device configured to assist left-ventricular functioning of a subject, the left ventricular assist device comprising:
      a tube configured to traverse an aortic valve of the subject, such that a proximal portion of the tube is at least partially disposed within an ascending aorta of the subject and a distal portion of the tube is disposed at least partially a left ventricle of the subject;
      a frame disposed within the distal portion of the tube, the frame being configured to hold a distal portion of the tube in an open state,
      the frame not being disposed within the proximal portion of the tube, and the proximal portion of the tube thereby being configured to collapse inwardly in response to pressure outside of the proximal portion of the tube exceeding pressure inside the proximal portion of the tube;
      a pump disposed within the frame and configured to pump blood through the tube from the subject's left ventricle to the subject's aorta, such that, the proximal portion of the tube is maintained in an open state when blood pressure generated within the proximal portion of the tube by the blood pump exceeds aortic pressure of the subject outside the proximal portion of the tube; and
      a plurality of elongate commissure elements that are disposed within the proximal portion of the tube, such that, when the proximal portion of the tube collapses inwardly, respective portions of a circumference of the tube form cusps that contact each other.

Inventive concept 89. The apparatus according to inventive concept 88, further comprising a computer processor that is configured to control pumping of blood through the tube by the blood pump, such that blood pressure generated by the blood pump within the tube exceeds systolic aortic pressure of the subject, and is less than diastolic aortic pressure of the subject.

Inventive concept 90. The apparatus according to inventive concept 88, further comprising a pressure sensor configured to measure aortic blood pressure of the subject, and wherein the computer processor is configured to receive an indication of the measured aortic blood pressure, and to control pumping of blood through the tube by the blood pump responsively to the measured aortic blood pressure.

Inventive concept 91. The apparatus according to inventive concept 88, further comprising a pressure sensor configured to measure left-ventricular blood pressure of the subject, and wherein the computer processor is configured to receive an indication of the measured left-ventricular blood pressure, and to control pumping of blood through the tube by the blood pump responsively to the measured left-ventricular blood pressure.

Inventive concept 92. Apparatus, for use with a delivery device, the apparatus comprising:
   an impeller;
   a frame disposed around the impeller,
   the impeller and the frame being configured to be inserted into a blood vessel of a subject via the delivery device, while disposed in radially-constrained configurations thereof, and to assume non-radially-constrained configuration by being released from the delivery device; and
   a coupling element comprising a first portion disposed upon the impeller, and a second portion disposed on the frame and configured to engage with the first portion, the coupling element being configured to facilitate radial constriction of the impeller by holding an end of the impeller such that the impeller can be axially elongated, without radially constricting the frame.

Inventive concept 93. Apparatus comprising:
   a blood-pump tube;
   an impeller configured to be disposed within the blood-pump tube, and to pump blood from a first location to a second location by pumping blood through the blood-pump tube:
   a motor disposed outside the subject's body, and configured to drive the impeller to rotate;
   a drive cable extending from outside the subject's body to the axial shaft, and configured to impart rotational motion from the motor to the impeller, by rotating;
   an outer tube disposed around the drive cable configured to extend from outside the subject's body to within the blood-pump tube, the outer tube defining first and second openings on a portion of the outer tube disposed within the blood-pump tube; and
   a flow obstacle disposed over the first opening, such that the first opening is configured to function as a stagnation pressure tap, and the second opening is configured to function as a static pressure tap;
   at least one pressure sensor configured to measure pressure within the stagnation pressure tap and pressure within the static pressure tap; and
   a computer processor configured to determine flow through the blood-pump tube, at least partially based upon the pressure measured within the stagnation pressure tap and the pressure measured within the static pressure tap.

Inventive concept 94. A method comprising:
inserting a blood pump into a body of subject, the blood pump including:
an impeller that includes proximal and distal bushings,
a frame disposed around the impeller, the frame including proximal and distal bearings, and
an axial shaft that passes through the proximal and distal bearings of the frame and the proximal and distal bushings of the impeller, the proximal bushing of the impeller being coupled to the axial shaft, such that the proximal bushing is held in an axially-fixed position with respect to the axial shaft, and the distal bushing of the impeller not being coupled to the axial shaft, such that the distal bushing is not held in an axially-fixed position with respect to the axial shaft,
the impeller being maintained in a radially-constrained configuration by a delivery catheter while the impeller is inserted into the subject's body;
when the impeller is disposed within the subject's body, causing the impeller to change from its radially-constrained configuration to a non-radially-constrained configuration by allowing the distal bushing to slide over the axial shaft, by releasing the impeller from the catheter; and
pumping blood through the subject's body using the impeller, while the impeller is disposed in its non-radially-constrained configuration.

Inventive concept 95. A method comprising:
placing an impeller of a ventricular assist device inside a left ventricle of a subject, with a frame disposed around the impeller; and
driving the impeller to pump blood from the left ventricle to an aorta of the subject, by rotating the impeller,
placement of the impeller inside the left ventricle being such that the impeller is allowed to undergo axial motion with respect to the frame, in response to cyclical changes in a pressure difference between the left ventricle and the aorta.

Inventive concept 96. A method comprising:
placing a blood pump inside a body of a subject the blood pump including:
an impeller with a frame disposed around the impeller, the impeller including proximal and distal bushings, and the frame including proximal and distal bearings, and
an axial shaft that passes through the proximal and distal bearings of the frame and the proximal and distal bushings of the impeller, the axial shaft being coupled to at least one of the proximal and distal bushings of the impeller, such that the at least one bushing is held in an axially-fixed position with respect to the axial shaft, and not being held in an axially-fixed position with respect to the proximal and distal bearings; and
pumping blood through the subject's body, using the impeller.

Inventive concept 97. A method comprising:
placing an impeller of a blood pump inside a body of a subject, with a frame disposed around the impeller; and
driving the impeller to pump blood through the subject's body, without using any thrust bearing disposed within the subject's body to provide opposition to thrust generated by the rotation of the impeller.

The present invention will be more fully understood from the following detailed description of embodiments thereof, taken together with the drawings, in which:

BRIEF DESCRIPTION OF THE DRAWINGS

FIGS. 2A, 2B, and 2C are schematic illustrations of a pump portion of a ventricular assist device, in accordance with some applications of the present invention;

FIG. 4 is a schematic illustration of an impeller disposed inside a frame of a ventricular assist device, in accordance with some applications of the present invention;

FIGS. 5A and 5B are schematic illustrations of the impeller and the frame of the ventricular assist device, respectively in non-radially-constrained and radially-constrained states thereof, in accordance with some applications of the present invention;

FIGS. 6A and 6B are schematic illustrations of a ventricular assist device at respective stages of a motion cycle of the impeller of the ventricular assist device with respect to the frame of the ventricular assist device, in accordance with some applications of the present invention;

FIG. 6C is a schematic illustration of an axial-shaft-receiving tube and a distal tip portion of a ventricular assist device, in accordance with some applications of the present invention;

FIGS. 10A, 10B, and 10C are schematic illustrations of a drive cable of a ventricular assist device, in accordance with some applications of the present invention;

FIGS. 11A, and 11B are schematic illustrations of an interface component that forms an interface between respective portions of the drive cable of the ventricular assist device, in accordance with some applications of the present invention;

FIGS. 11C, 11D, and 11E are schematic illustrations of an interface between the drive cable and an axial shaft of the ventricular assist device, in accordance with some applications of the present invention;

FIGS. 16A, 16B, 16C and 16D are schematic illustrations of a ventricular assist device that includes one or more blood-pressure-measurement tubes, in accordance with some applications of the present invention;

FIGS. 19A and 19B are schematic illustrations of a ventricular assist device, a tip portion of the device, being a radially-expandable atraumatic distal tip portion, in accordance with some applications of the present invention;

FIGS. 20A and 20B are schematic illustrations of a ventricular assist device, a tip portion of the device, being a radially-expandable atraumatic distal tip portion, in accordance with some applications of the present invention;

DETAILED DESCRIPTION OF EMBODIMENTS

Figure 1A:
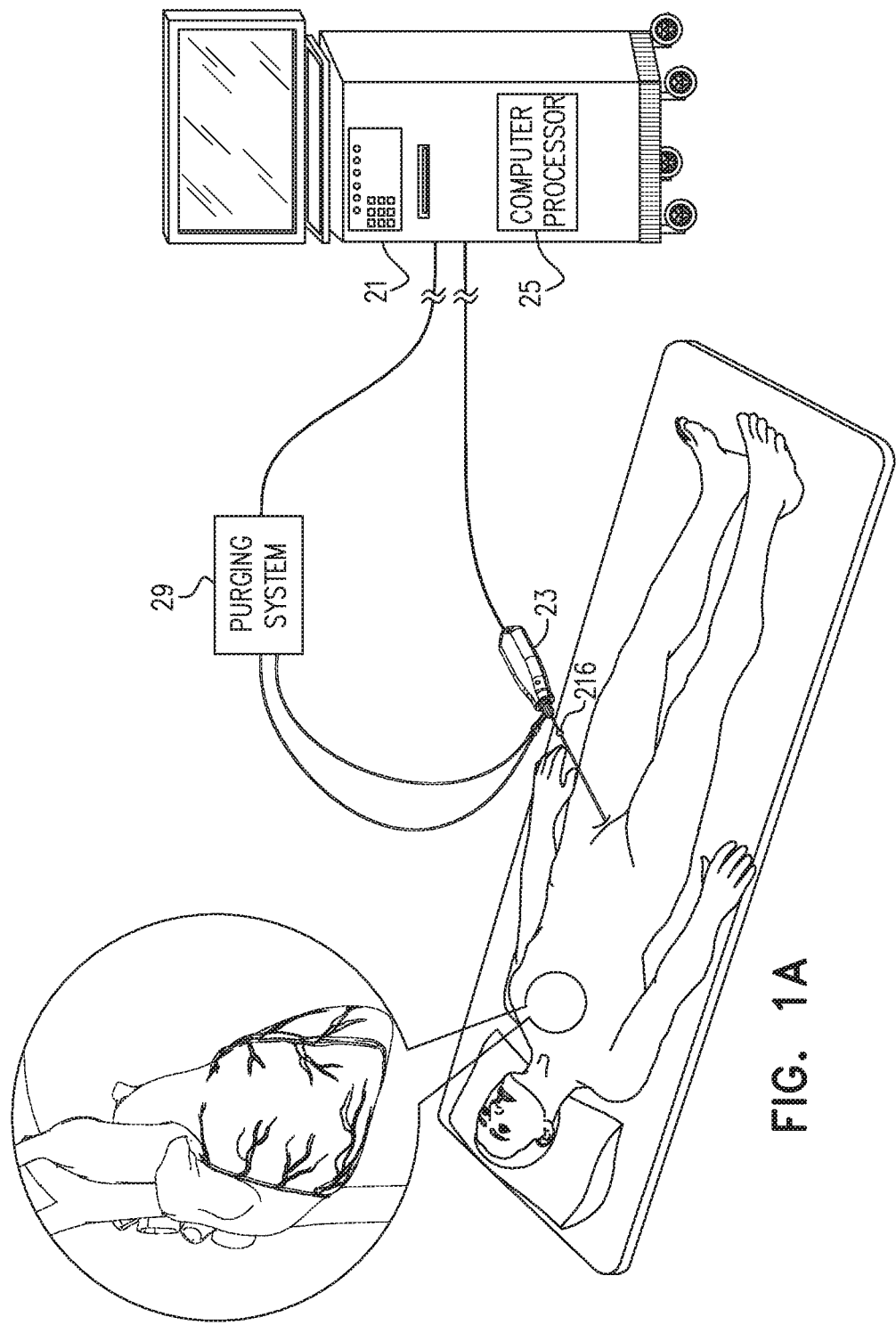
FIGS. 1A and 1B are schematic illustrations of a ventricular assist device, a distal end of which is disposed in a subject's left ventricle, in accordance with some applications of the present invention.
Figure 1B:
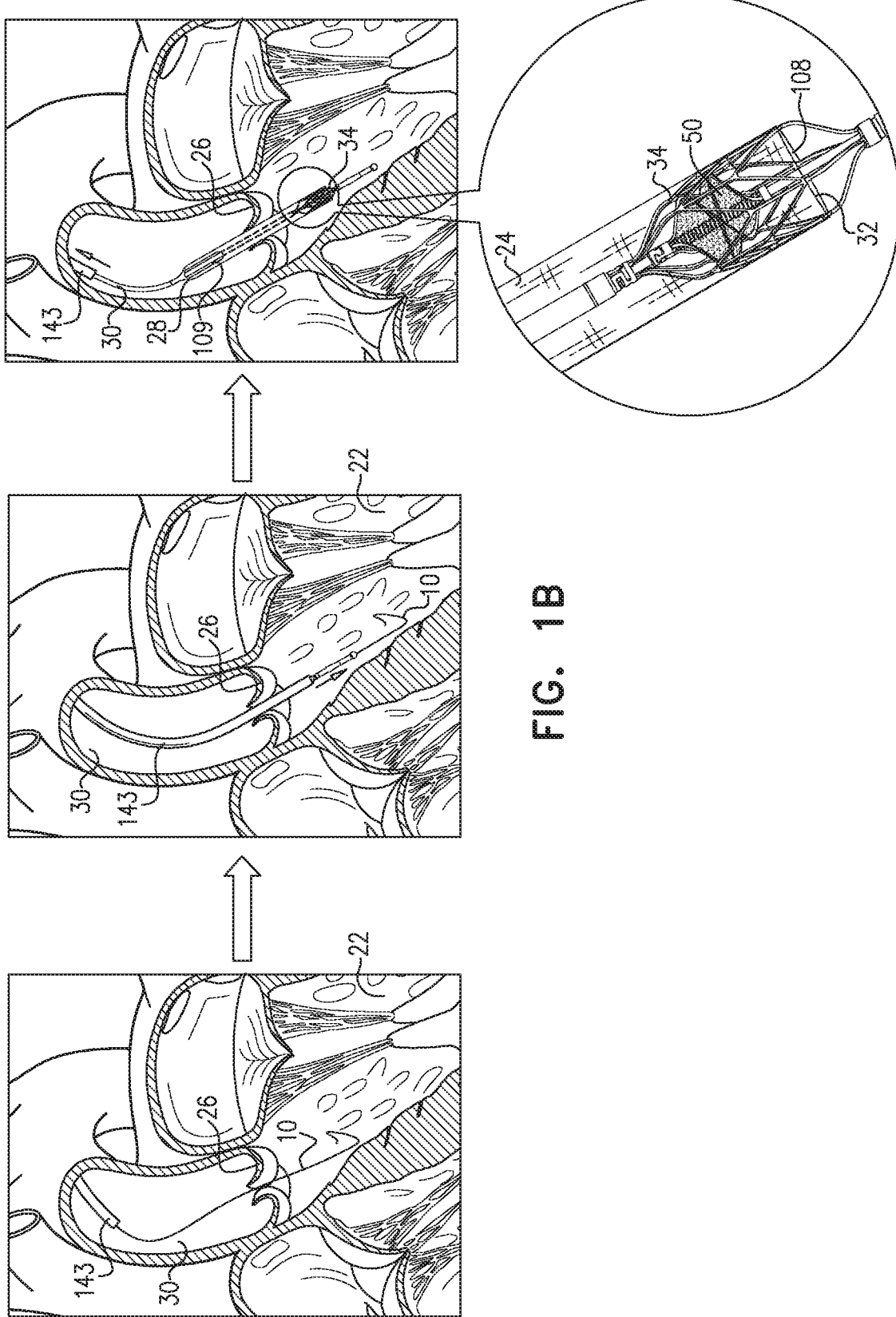

Reference is now made to FIGS. 1A and 1B, which are schematic illustrations of a ventricular assist device 20, a distal end of which is disposed in a subject's left ventricle 22, in accordance with some applications of the present invention. The ventricular assist device includes a tube 24, which traverses an aortic valve 26 of the subject, such that a proximal end 28 of the tube is disposed in an aorta 30 of the subject and a distal end 32 of the tube is disposed within left ventricle 22. Tube 24 (which is sometimes referred to herein as a "blood-pump tube") is typically an elongate tube, an axial length of the tube typically being substantially larger than its diameter. The scope of the present invention includes using the apparatus and methods described herein in anatomical locations other than the left ventricle and the aorta. Therefore, the ventricular assist device and/or portions thereof are sometimes referred to herein (in the specification and the claims) as a blood pump.

As shown in FIG. 1B, which shows steps in the deployment of the ventricular assist device in the left ventricle, typically the distal end of the ventricular assist device is guided to the left ventricle over a guidewire 10. During the insertion of the distal end of the device to the left ventricle, a delivery catheter 143 is disposed over the distal end of the device. Once the distal end of the device is disposed in the left ventricle, the delivery catheter is typically retracted to the aorta, and the guidewire is withdrawn from the subject's body. The retraction of the delivery catheter typically causes self-expandable components of the distal end of the device to assume non-radially-constrained configurations, as described in further detail hereinbelow. Typically, the ventricular assist device is inserted into the subject's body in order to provide an acute treatment to the subject. For some applications, in order to withdraw the left ventricular device from the subject's body at the end of the treatment, the delivery catheter is advanced over the distal end of the device, which causes the self-expandable components of the distal end of the device to assume radially-constrained configurations. Alternatively or additionally, the distal end of the device is retracted into the delivery catheter which causes the self-expandable components of the distal end of the device to assume radially-constrained configurations.

Figure 2C:
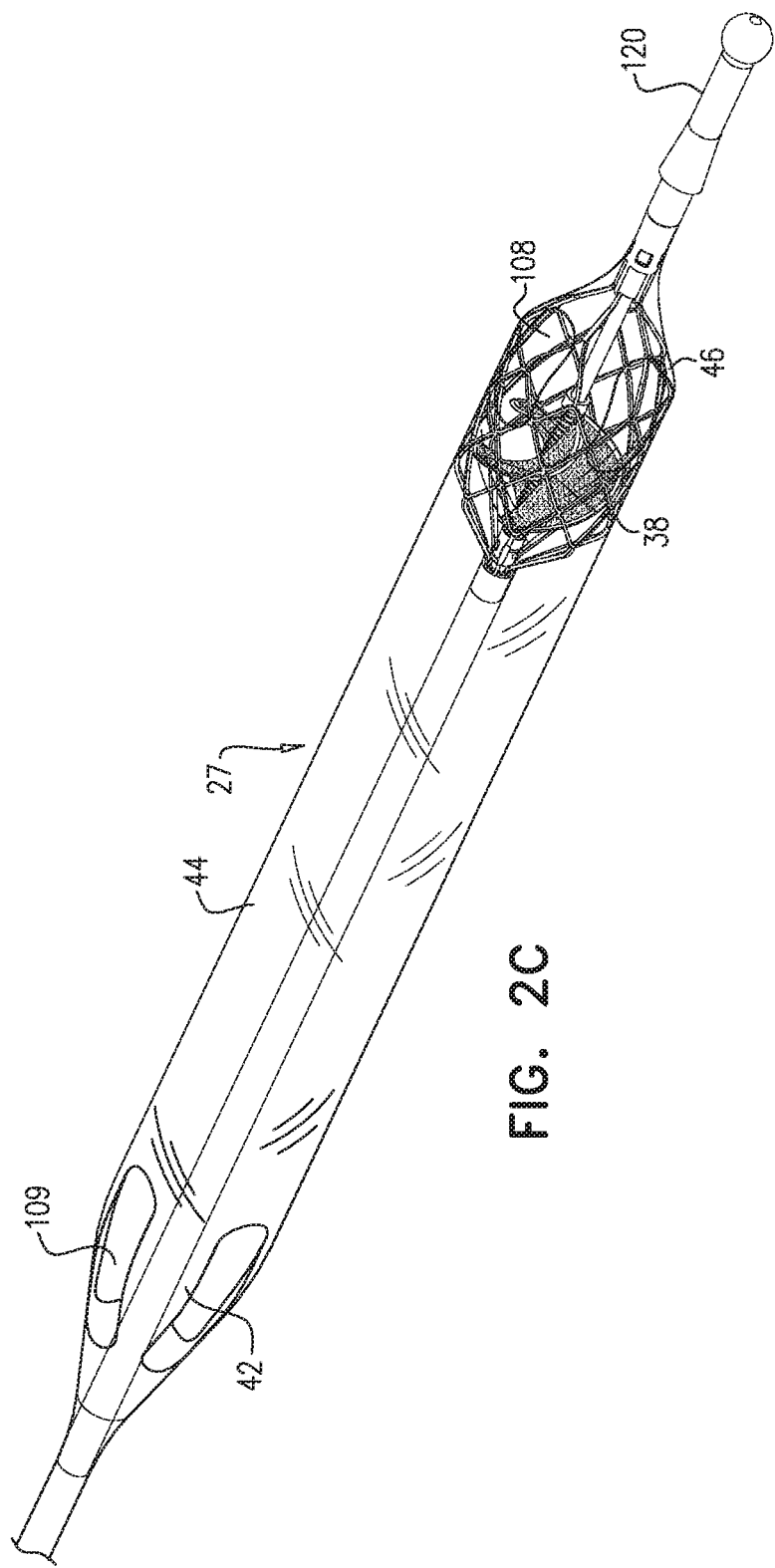

Reference is also made to FIGS. 2A, 2B, and 2C, which are schematic illustrations of a blood pump portion 27 of ventricular assist device 20, in accordance with some applications of the present invention. Typically, an impeller 50 is disposed within a distal portion 102 of tube 24 and is configured to pump blood from the left ventricle into the aorta by rotating. The tube typically defines one or more blood inlet openings 108 at the distal end of the tube, via which blood flows into the tube from the left ventricle, during operation of the impeller. For some applications, the proximal portion of the tube defines one or more blood outlet openings 109, via which blood flows from the tube into the ascending aorta, during operation of the impeller.

For some applications, a control console 21, which typically includes a computer processor 25 (shown in FIG. 1A), drives the impeller to rotate. For example, the computer processor may control a motor 74 (shown in FIG. 7), which is disposed within a motor unit 23 and which drives the impeller to rotate via a drive cable 130 (also shown in FIG. 7). For some applications, the computer processor is configured to detect a physiological parameter of the subject (such as left-ventricular pressure, cardiac afterload, etc.) and to control rotation of the impeller in response thereto, as described in further detail hereinbelow. Typically, the operations described herein that are performed by the computer processor, transform the physical state of a memory, which is a real physical article that is in communication with the computer processor, to have a different magnetic polarity, electrical charge, or the like, depending on the technology of the memory that is used. Computer processor 25 is typically a hardware device programmed with computer program instructions to produce a special-purpose computer. For example, when programmed to perform the techniques described herein, computer processor 25 typically acts as a special-purpose, ventricular-assist computer processor.

For some applications, a purging system 29 drives a fluid (e.g., a glucose solution) to pass through portions of ventricular assist device 20, for example, in order to cool portions of the device and/or in order to wash debris from portions of the device. Purging system 29 is described in further detail hereinbelow.

Typically, along distal portion 102 of tube 24, a frame 34 is disposed within the tube. The frame is typically made of a shape-memory alloy, such as nitinol. For some applications, the shape-memory alloy of the frame is shape set such that the frame (and thereby the tube) assumes a generally circular, elliptical, or polygonal cross-sectional shape in the absence of any forces being applied to the tube. By assuming its generally circular, elliptical, or polygonal cross-sectional shape, the frame is configured to hold the distal portion of the tube in an open state. Typically, during operation of the ventricular assist device, the distal portion of the tube is configured to be placed within the subject's body, such that the distal portion of the tube is disposed at least partially within the left ventricle.

For some applications (not shown), during operation of the ventricular assist device, the distal portion of the tube is disposed at least partially within the native aortic valve and the frame is configured to hold open the aortic valve, by assuming its generally circular, elliptical, or polygonal cross-sectional shape. For some applications, tube 24 is sized such as to prevent the shape-memory alloy of frame 34 from fully assuming the dimensions to which the shape-memory alloy was shape set. In this manner, the frame is "pre-tensioned," such that even if the aortic valve applies a radially compressive force to the tube and the frame, the frame does not become radially compressed, since the frame is already being maintained in a partial radially-constrained state by the tube. For some applications, the frame includes a plurality of rigid struts 111 that are disposed in parallel to each other, and in parallel to the longitudinal axis of the frame. The rigid struts are configured such that at least a portion 110 of the frame along which the struts are disposed maintains a substantially straight longitudinal axis, even when subjected to anatomical forces within the left ventricle and/or the aortic valve. Typically, rigid struts are configured such that even as frame 34 changes from a radially-constrained configuration (in which the frame is typically disposed during introduction of the frame into the subject's body) to a non-radially-constrained configuration (in which the frame is typically disposed during operation of the ventricular assist device), the lengths of the rigid struts do not change.

For some applications, along a proximal portion 106 of tube 24, the frame is not disposed within the tube, and the tube is therefore not supported in an open state by frame 34. Tube 24 is typically made of a blood-impermeable collapsible material. For example, tube 24 may include polyurethane, polyester, and/or silicone. Typically, the proximal portion of the tube is configured to be placed such that it is at least partially disposed within the subject's ascending aorta. For some applications, the proximal portion of the tube traverses the subject's aortic valve, passing from the subject's left ventricle into the subject's ascending aorta, as shown in FIG. 1B. As described hereinabove, the tube typically defines one or more blood inlet openings 108 at the distal end of the tube, via which blood flows into the tube from the left ventricle, during operation of the impeller. For some applications, the proximal portion of the tube defines one or more blood outlet openings 109, via which blood flows from the tube into the ascending aorta, during operation of the impeller. Typically, the tube defines a plurality of blood outlet openings 109, for example, between two and eight blood outlet openings (e.g., between two and four blood outlet openings). During operation of the impeller, the pressure of the blood flow through the tube typically maintains the proximal portion of the tube in an open state. For some applications, in the event that, for example, the impeller malfunctions, the proximal portion of the tube is configured to collapse inwardly, in response to pressure outside of the proximal portion of the tube exceeding pressure inside the proximal portion of the tube. In this manner, the proximal portion of the tube acts as a safety valve, preventing retrograde blood flow into the left ventricle from the aorta.

For some applications, computer processor 25 of control console 21 (shown in FIG. 1A) is configured to control pumping of the blood pump (e.g., by controlling rotation of the impeller) such that the blood pressure generated by the pump within tube 24 exceeds the subject's systolic aortic pressure during systole, but is less than the subject's diastolic aortic pressure during diastole. During systole, proximal portion 106 of tube 24 is held open since the blood pressure within the tube exceeds the aortic pressure exerted upon the tube from outside the tube. During diastole, the proximal portion of tube 24 closes, since the aortic pressure exerted upon the tube from outside the tube exceeds blood pressure within the tube. In this manner, the impeller pumps blood from the left ventricle to the aorta in a pulsatile manner (i.e., by only pumping blood from the left ventricle to the aorta during diastole). For some applications, the computer processor is configured to measure the subject's aortic pressure, left-ventricular pressure, and/or flow through tube 24 for example using techniques as described hereinbelow with reference to FIGS. 9, 16A-D, and/or 17. For some such applications, based upon the measured aortic pressure, left-ventricular pressure, and/or flow, the computer processor controls rotation of the impeller in the above-described manner. Alternatively, the computer processor controls rotation of the impeller, based upon the measured aortic pressure, left-ventricular pressure, and/or flow in a different manner from the above-described manner. For example, the computer processor may be configured to change the rate of rotation of the impeller based upon the measured aortic pressure, left-ventricular pressure, and/or flow, but in a manner that results in the impeller pumping blood from the left ventricle to the aorta in a non-pulsatile, continuous manner.

Typically, pumping of blood by the impeller increases aortic pressure and reduces left-ventricular pressure. Once flow through tube 24 reaches a critical value above which aortic pressure is higher than left-ventricular pressure even in ventricular systole (hereinafter "systole"), the aortic valve remains closed around the outside of tube 24 throughout the cardiac cycle and flow from the ventricle to the aorta occurs exclusively via the tube. Typically, above this point of uncoupling aortic from ventricular pressure, the left ventricle no longer performs net external work (defined as volume change times pressure change), as it is not moving any volume. In this mode, oxygen consumption by the left ventricle depends on cyclic pressure generation against a closed aortic valve, wall tension that results from the size of the left ventricle, wall thickness, as well as baseline metabolic demands (including calcium cycling). Below this critical point of impeller activity, the aortic valve is typically at least partially open in systole and left ventricular outflow will occur both between the outside of the tube and the aortic valve (by virtue of left ventricular contraction) as well as through the tube (by virtue of the impeller rotating and pumping). For a given number of impeller revolutions per minute, flow through the tube will typically be greater the larger the cross-sectional area of the sleeve. At the same time, the larger the cross-sectional area of the tube, the more space the tube occupies within the left ventricular outflow tract, the smaller the remaining outflow area, and consequently, the higher the outflow resistance the left ventricle has to overcome for pumping around the outside of the tube.

Hence, typically, a trade-off exists between the efficiency of the impeller in assisting the left ventricle (which favorably increases with tube diameter) and the residual resistance to outflow around the outside of the tube 24 (which unfavorably increases with tube diameter). The higher the flow through the tube provided by the impeller (for a given tube diameter), the less the effect of the reduced cross-sectional outflow area on effective outflow resistance may matter, as the remaining cross-sectional area may be appropriate for the residual small stroke volume that the ventricle has to eject, i.e., the reduced residual outflow tract area may not pose an undue resistance to outflow. Conversely, however, once a fixed tube diameter is selected, effective resistance to outflow increases as flow through the tube decreases, since a larger proportion of left ventricular stroke volume now needs to pass the residual outflow tract area around the tube. Therefore, for some applications, left ventricular outflow resistance is configured to automatically adjust in order to compensate for changes in the blood flow through the tube that is generated by the impeller. For example, the tube may be made of a compliant material, the compliance of which is such that a decrease in flow through the tube, and the subsequent drop in distending pressure, results in a decrease in sleeve diameter, thereby increasing the outflow area available for the left ventricle.

Typically, the material properties of the compliant material are defined such that (a) maximum tube expansion is reached just at, or close to, the point when the pump-flow-generated intraluminal pressure exceeds aortic pressure (irrespective of the point in the cardiac cycle) and hence remains above left-ventricular pressure throughout the cardiac cycle, and (b) full collapse of the tube is reached when flow through the tube that is generated by the impeller becomes zero.

Referring now to FIG. 2B, for some applications, a plurality of elongate commissure elements 107 extend along at least some of proximal portion 106 of tube 24. As described hereinabove, for some applications, computer processor 25 is configured to drive impeller 50 to pump blood from the left ventricle to the aorta in a pulsatile manner. For some applications, the commissure elements are configured to facilitate opening and closing of the proximal portion of the tube in a manner that is similar to the opening and closing of native valve leaflets, with respective portions of the circumference of the tube forming cusps that contact each other when the tube closes. For some applications, the ventricular assist device includes three elongate commissure elements, and the proximal portion of tube 24 is configured to close in a manner that is similar to that of a tri-leaflet valve. (FIG. 2B depicts such an embodiment, but one of the commissure elements is hidden from view.) For some applications (not shown), the ventricular assist device includes two elongate commissure elements, and the proximal portion of tube 24 is configured to close in a manner that is similar to that of a bi-leaflet valve. For some applications, the proximal portion of tube 24 is placed such as to traverse the subject's aortic valve, and the commissure elements are rotationally aligned with the commissures of the native valve. In this manner, the artificial cusps of the proximal portion of the tube are aligned with the native aortic valve leaflets.

Referring to FIGS. 2A-C, for some applications, frame 34 is shaped such that the frame defines a proximal conical portion 36, a central cylindrical portion 38, and a distal conical portion 40. Typically, the proximal conical portion is such that the narrow end of the cone is proximal with respect to the wide end of the cone. Further typically, the distal conical portion is such that the narrow end of the cone is distal with respect to the wide end of the cone. For some applications, tube 24 extends to the end of cylindrical portion 38, such that the distal end of the tube defines a single axially-facing blood inlet opening 108, as shown in FIGS. 2A and 2B. Alternatively, tube 24 extends to the end of distal conical portion 40, and the tube defines one or more lateral blood inlet openings, as shown in FIG. 2C. For such applications, the tube typically defines two to four lateral blood inlet openings.

Typically, tube 24 includes a conical proximal portion 42 and a cylindrical central portion 44. The proximal conical portion is typically such that the narrow end of the cone is proximal with respect to the wide end of the cone. As described hereinabove, for some applications, the tube extends to the end of distal conical portion 40 of frame 34. For such applications, the tube typically defines a distal conical portion 46, with the narrow end of the cone being distal with respect to the wide end of the cone, as shown in FIG. 2C. For some applications (not shown), the diameter of tube 24 changes along the length of the central portion of the tube, such that the central portion of the tube has a frusto-conical shape. For example, the central portion of the tube may widen from its proximal end to is distal end, or may narrow from its proximal end to its distal end. For some applications, at its proximal end, the central portion of the tube has a diameter of between 5 and 7 mm, and at its distal end, the central portion of the tube has a diameter of between 8 and 12 mm.

Figure 3A:
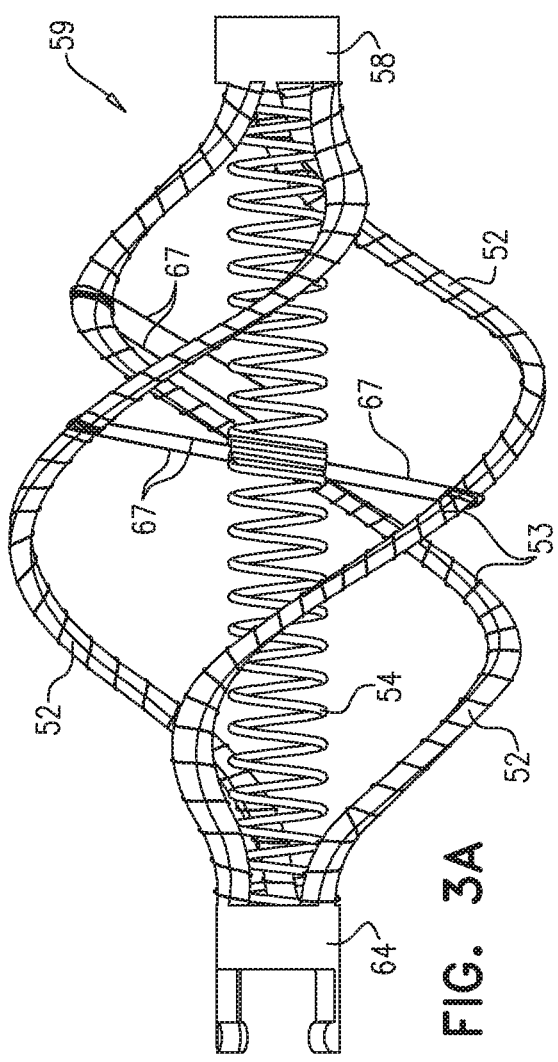
FIGS. 3A, 3B, and 3C are schematic illustrations of an impeller of a ventricular assist device, in accordance with some applications of the present invention.
Figure 3B:
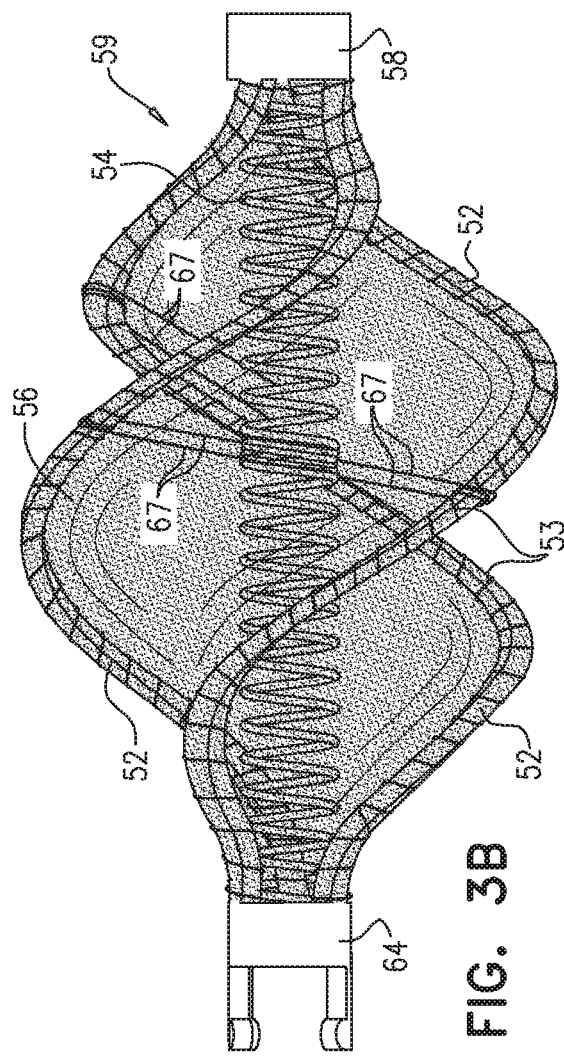
Figure 3C:
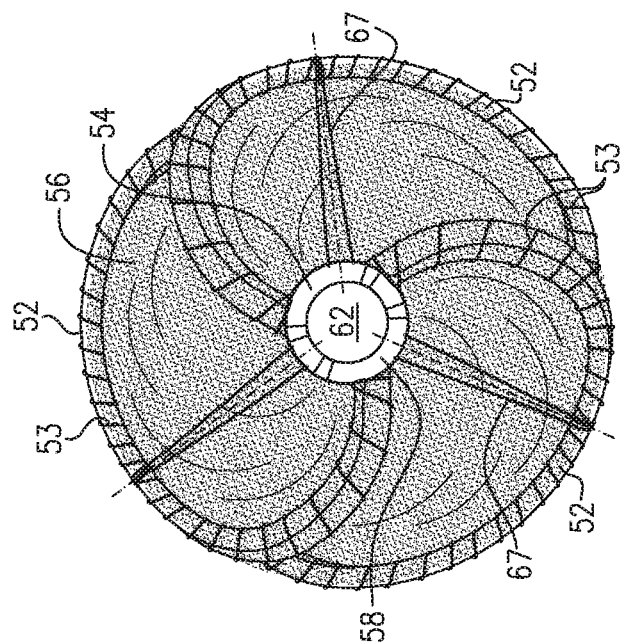

Reference is now made to FIGS. 3A-C, which are schematic illustrations of impeller 50, in accordance with some applications of the present invention. Typically, the impeller includes at least one outer helical elongate element 52, which winds around a central axial spring 54, such that the helix defined by the helical elongate element is coaxial with the central axial spring. Typically, the impeller includes two or more helical elongate elements (e.g., three helical elongate elements, as shown in FIGS. 3A-C). For some applications, the helical elongate elements and the central axial spring are made of a shape-memory material, e.g., a shape-memory alloy such as nitinol. Typically, each of the helical elongate elements and the central axial spring support a film 56 of a material (e.g., a polymer, such as polyurethane, and/or silicone) therebetween. For illustrative purposes, the impeller is shown in the absence of the material in FIG. 3A. FIGS. 3B and 3C show respective views of the impeller with the material supported between the helical elongate elements and the spring.

Each of the helical elongate elements, together with the film extending from the helical elongate element to the spring, defines a respective impeller blade, with the helical elongate elements defining the outer edges of the blades, and the axial spring defining the axis of the impeller. Typically, the film of material extends along and coats the spring. For some applications, sutures 53 (e.g., polyester sutures, shown in FIGS. 3B and 3C) are wound around the helical elongate elements, e.g., as described in US 2016/0022890 to Schwammenthal, which is incorporated herein by reference. Typically, the sutures are configured to facilitate bonding between the film of material (which is typically a polymer, such as polyurethane, or silicone) and the helical elongate element (which is typically a shape-memory alloy, such as nitinol). For some applications, sutures (e.g., polyester sutures, not shown) are wound around spring 54. Typically, the sutures are configured to facilitate bonding between the film of material (which is typically a polymer, such as polyurethane, or silicone) and the spring (which is typically a shape-memory alloy, such as nitinol).

Typically, proximal ends of spring 54 and helical elongate elements 52 extend from a proximal bushing (i.e., sleeve bearing) 64 of the impeller, such that the proximal ends of spring 54 and helical elongate elements 52 are disposed at a similar radial distance from the longitudinal axis of the impeller, as each other. Similarly, typically, distal ends of spring 54 and helical elongate elements 52 extend from a distal bushing 58 of the impeller, such that the distal ends of spring 54 and helical elongate elements 52 are disposed at a similar radial distance from the longitudinal axis of the impeller, as each other. Typically, spring 54, as well as proximal bushing 64 and distal bushing 58 of the impeller, define a lumen 62 therethrough.

Reference is now made to FIG. 4, which is a schematic illustration of impeller 50 disposed inside frame 34 of ventricular assist device 20, in accordance with some applications of the present invention. As shown, typically there is a gap G, between the outer edge of impeller 50 and the inner surface of frame 34, even at a location at which the span of the impeller is at its maximum. For some applications, it is desirable that the gap between the outer edge of the blade of the impeller and the inner surface of frame 34 be relatively small, in order for the impeller to efficiently pump blood from the subject's left ventricle into the subject's aorta. However, it is also desirable that a gap between the outer edge of the blade of the impeller and the inner surface of frame 34 be maintained, for example, in order to reduce the risk of hemolysis.

For some applications, the gap G between the outer edge of the impeller and the inner surface of frame 34, at the location at which the span of the impeller is at its maximum, is greater than 0.05 min (e.g., greater than 0.1 mm), and/or less than 1 mm (e.g., less than 0.4 mm), e.g., 0.05 mm-1 mm, or 0.1 mm-0.4 mm. For some applications, the outer diameter of the impeller at the location at which the outer diameter of the impeller is at its maximum is more than 6 mm (e.g., more than 6.5 mm), and/or less than 8 mm (e.g., less than 7 mm), e.g., 6-8 mm, or 6.5-7 mm. For some applications, the inner diameter of frame 34 is more than 6.5 mm (e.g. more than 7 mm), and/or less than 8.5 mm (e.g., less than 7.5 mm), e.g., 6.5-8.5 mm, or 7-7.5 mm.

Typically, an axial shaft 92 passes through the axis of impeller 50, via lumen 62 of the impeller. Typically, proximal bushing 64 of the impeller is coupled to the shaft such that the axial position of the proximal bushing with respect to the shaft is fixed, and distal bushing 58 of the impeller is slidable with respect to the shaft. The axial shaft itself is radially stabilized via a proximal radial bearing 116 and a distal radial bearing 118, defined by frame 34. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller.

Referring again to FIGS. 3A-C, for some applications, the impeller includes a plurality of elongate elements 67 extending radially from central axial spring 54 to outer helical elongate elements 52. The elongate elements are typically flexible but are substantially non-stretchable along the axis defined by the elongate elements. Further typically, each of the elongate elements is configured not to exert force upon the helical elongate element, unless force is acting upon the impeller that is causing the helical elongate element to move radially outward such that (in the absence of the elongate element) a separation between the helical elongate element and the central axial spring would be greater than a length of the elongate element. For example, the elongate elements may include strings (such as polyester, and/or another polymer or a natural material that contains fibers) and/or wires (such as nitinol wires, and/or wires made of a different alloy, or a metal).

For some applications, the elongate elements 67 maintain the helical elongate element (which defines the outer edge of the impeller blade) within a given distance with respect to the central axial spring. In this manner, the elongate elements are configured to prevent the outer edge of the impeller from being forced radially outward due to forces exerted upon the impeller during the rotation of the impeller. The elongate elements are thereby configured to maintain the gap between the outer edge of the blade of the impeller and the inner surface of frame 34, during rotation of the impeller. Typically, more than one (e.g., more than two) and/or fewer than eight (e.g., fewer than four) elongate elements 67 are use in the impeller, with each of the elongate elements typically being doubled (i.e., extending radially from central axial spring 54 to an outer helical elongate element 52, and then returning from the helical elongate element back to the central axial spring). For some applications, a plurality of elongate elements, each of which extends from the spring to a respective helical elongate element and back to the spring, are formed from a single piece of string or a single wire, as described in further detail hereinbelow.

For some applications, the impeller is manufactured in the following manner Proximal bushing 64, distal bushing 58, and helical elongate elements 52 are cut from a tube of shape-memory material, such as nitinol. The cutting of the tube, as well as the shape setting of the shape-memory material, is typically performed such that the helical elongate elements are defined by the shape-memory material, e.g., using generally similar techniques to those described in US 2016/0022890 to Schwammenthal. Typically, spring 54 is inserted into the cut and shape-set tube, such that the spring extends along the length of the tube from at least the proximal bushing to the distal bushing. For some applications, the spring is inserted into the cut and shape-set tube while the spring is in an axially compressed state, and the spring is configured to be held in position with respect to the tube, by exerting a radial force upon the proximal and distal bushings. Alternatively or additionally, portions of the spring are welded to the proximal and distal bushings. For some applications, the spring is cut from a tube of a shape-memory material, such as nitinol. For some such applications, the spring is configured such that, when the spring is disposed in a non-radially-constrained configuration (in which the spring is typically disposed during operation of the impeller), there are substantially no gaps between windings of the spring and adjacent windings thereto.

For some applications, at this stage, elongate elements 67, as described hereinabove, are placed such as to extend between the spring and one or more of the helical elongate elements, for example, in the following manner A mandrel (e.g., a polyether ether ketone (PEEK) and/or a polytetrafluoroethylene (PTFE) mandrel) is inserted through the lumen defined by the spring and the bushings. A string or a wire is then threaded such that it passes (a) from the mandrel to a first one of the helical elongate elements, (b) back from the first of the helical elongate elements to the mandrel, (c) around the mandrel, and to a second one of the helical elongate elements, (d) back from the second one of the helical elongate elements to the mandrel, etc. Once the string or the wire has been threaded from the mandrel to each of the helical elongate elements and back again, the ends of the string or the wire are coupled to each other, e.g., by tying them to each other. For some applications, sutures 53 (e.g., polyester sutures) are wound around the helical elongate elements, in order to facilitate bonding between the film of material (which is typically a polymer, such as polyurethane, or silicone) and the helical elongate elements (which is typically a shape-memory alloy, such as nitinol), in a subsequent stage of the manufacture of the impeller. For some applications, sutures (e.g., polyester sutures, not shown) are wound around spring 54. Typically, the sutures are configured to facilitate bonding between the film of material (which is typically a polymer, such as polyurethane, or silicone) and the spring (which is typically a shape-memory alloy, such as nitinol), in the subsequent stage of the manufacture of the impeller.

Typically, at this stage, a structure 59 has been assembled that is as shown in FIG. 3A. The structure includes the cut and shape-set tube that defines the proximal and distal bushing and helical elongate elements, the spring, and optionally the elongate elements, and the sutures. This structure is dipped into the material that defines film 56. For some applications, the assembled structure is dipped into the material with the mandrel disposed through the lumen defined by the spring and the bushings, although it is noted that the mandrel is not shown in FIG. 3A. Typically, the material from which the film is made is silicone (and/or a similar polymer), and the assembled structure is dipped into the material, while the material is in an uncured, liquid state. Subsequently, the material is cured such that it solidifies, e.g., by being left to dry. Once the material has dried, the mandrel is typically removed from the lumen defined by the bushings and the spring.

The result of the process described above is typically that there is a continuous film of material extending between each of the helical elongate elements to the spring, and also extending along the length of the spring, such as to define a tube, with the spring embedded within the tube. The portions of the film that extend from each of the helical elongate elements to the spring define the impeller blades. For applications, in which the impeller includes elongate elements 67, the elongate elements are typically embedded within these portions of film.

Typically, impeller 50 is inserted into the left ventricle transcatheterally, while impeller 50 is in a radially-constrained configuration. In the radially-constrained configuration, both helical elongate elements 52 and central axial spring 54 become axially elongated, and radially constrained. Typically film 56 of the material (e.g., silicone) changes shape to conform to the shape changes of the helical elongate elements and the axial support spring, both of which support the film of material. Typically, using a spring to support the inner edge of the film allows the film to change shape without the film becoming broken or collapsing, due to the spring providing a large surface area to which the inner edge of the film bonds. For some applications, using a spring to support the inner edge of the film reduces a diameter to which the impeller can be radially constrained, relative to if, for example, a rigid shaft were to be used to support the inner edge of the film, since the diameter of the spring itself can be reduced by axially elongating the spring.

As described hereinabove, for some applications, proximal bushing 64 of impeller 50 is coupled to axial shaft 92 such that the axial position of the proximal bushing with respect to the shaft is fixed, and distal bushing 58 of the impeller is slidable with respect to the shaft. For some applications, when the impeller is radially constrained for the purpose of inserting the impeller into the ventricle or for the purpose of withdrawing the impeller from the subject's body, the impeller axially elongates by the distal bushing sliding along the axial shaft distally.

Subsequent to being released inside the subject's body, the impeller assumes its non-radially-constrained configuration (in which the impeller is typically disposed during operation of the impeller), as shown in FIGS. 3A-C. Typically, the pitch of each of the helical elongate elements 52, when impeller 50 is in a non-radially-constrained configuration (e.g., inside the subject's ventricle), is greater than 1 mm (e.g., greater than 6 mm), and/or less than 20 mm (e.g., less than 10 mm). Typically, ceteris paribus, the greater the pitch of the helical elongate element (and therefore the impeller blade), the greater the blood flow that is generated by the impeller. Therefore, as described, the pitch of the helical elongate elements 52, when impeller 50 is in the non-radially-constrained configuration, is typically greater than 1 mm (e.g., greater than 6 mm). On the other hand, it is typically desirable that the impeller occludes backflow of blood into the subject's left ventricle. Ceteris paribus, it is typically the case that the smaller the pitch of the helical elongate element (and therefore the impeller blade), the greater the occlusion that is provided by the impeller. Therefore, as described, the pitch of the helical elongate elements 52, when impeller 50 is in the non-radially-constrained configuration, is typically less than 20 mm (e.g., less than 10 mm).

For some applications, the pitch of the helical elongate elements (and therefore the impeller blade) varies along the length of the helical elongate element, at least when the impeller is in a non-radially-constrained configuration. Typically, for such applications, the pitch increases from the distal end of the impeller (i.e., the end that is inserted further into the subject's body, and that is placed upstream with respect to the direction of antegrade blood flow) to the proximal end of the impeller (i.e., the end that is placed downstream with respect to the direction of antegrade blood flow), such that the pitch increases in the direction of the blood flow. Typically, the blood flow velocity increases along the impeller, along the direction of blood flow. Therefore, the pitch is increased along the direction of the blood flow, such as to further accelerate the blood.

It is noted that, for illustrative purposes, in some of the figures, impeller 50 is shown without including all of the features of the impeller as shown and described with respect to FIGS. 3A-C. For example, some of the figures show the impeller not including sutures 53 and/or elongate elements 67. The scope of the present application includes using an impeller with any of the features shown and described with respect to FIGS. 3A-C in combination with any of the apparatus and methods described herein.

Reference is now made to FIGS. 5A and 5B, which are schematic illustrations of impeller 50 and frame 34 of ventricular assist device 20, respectively in non-radially-constrained and radially-constrained states thereof, in accordance with some applications of the present invention. The impeller and the frame are typically disposed in the radially-constrained states during the transcatheteral insertion of the impeller and the frame into the subject's body, and are disposed in the non-radially-constrained states during operation of the impeller inside the subject's left ventricle. As described hereinabove, typically tube 24 extends from at least a distal portion of the frame and proximally therefrom. However, for illustrative purposes, the frame and the impeller are shown in the absence of tube 24 in FIGS. 5A-B. As indicated in FIG. 5B, the frame and the impeller are typically maintained in radially-constrained configurations by delivery catheter 143.

Figure 5C:
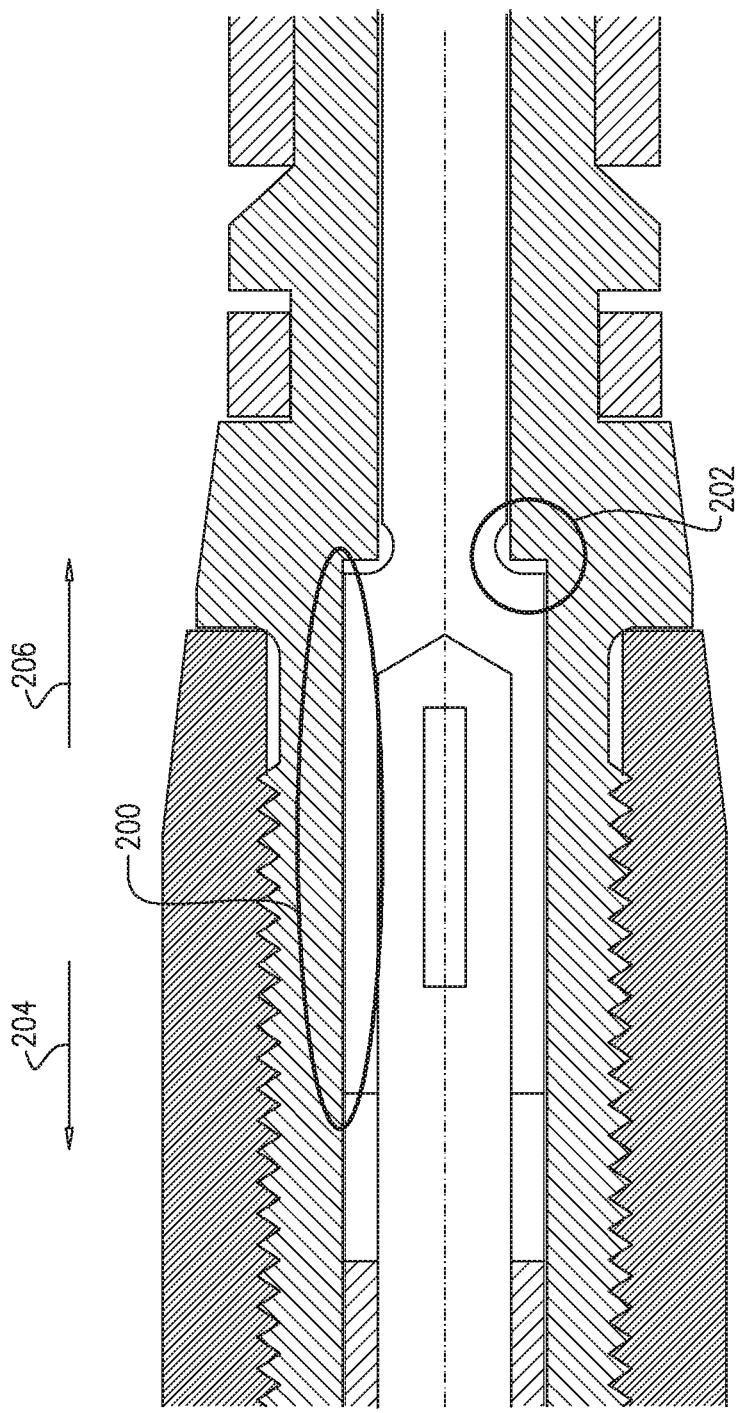
FIG. 5C is a schematic illustration of a typical bearing assembly that is used in prior art axial impeller-based blood pumps.

Reference is also made to FIG. 5C, which shows a typical bearing assembly that is used in prior art axial impeller-based blood pumps. FIG. 5C is shown for the purpose of acting as a point of reference for some of the applications of the invention described herein. As shown in FIG. 5C, a bearing assembly typically includes a radial bearing (indicated by ellipse 200) and a thrust bearing (indicated by circle 202). The radial bearing is configured to reduce radial motion of the impeller, by maintaining the axis of the impeller at a given radial position. In response to an impeller pumping blood in a first direction, forces acting upon the impeller typically push the impeller to move in the opposite direction to the first direction. The purpose of a thrust bearing is to oppose such motion of the impeller and to maintain the axial position of the impeller. In the example shown in FIG. 5C, in response to the impeller pumping blood in the direction of arrow 204, the impeller gets pushed in the direction of arrow 206, and the thrust bearing opposes this motion. Typically, due to the frictional forces that are exerted upon them, bearings undergo a substantial amount of heating and wear. Thrust bearings are typically exposed to substantial heating and wear, due to the fact that the frictional forces that are exerted upon them are typically spread over opposing surfaces having a smaller contact area between them, than is the case for radial bearings.

As described hereinabove, typically, axial shaft 92 passes through the axis of impeller 50, via lumen 62 of the impeller. Typically, proximal bushing 64 of the impeller is coupled to the shaft via a coupling element 65 such that the axial position of the proximal bushing with respect to the shaft is fixed, and distal bushing 58 of the impeller is slidable with respect to the shaft. The axial shaft itself is radially stabilized via a proximal radial bearing 116 and a distal radial bearing 118, defined by frame 34. In turn, the axial shaft, by passing through lumen 62 defined by the impeller, radially stabilizes the impeller with respect to the inner surface of frame 34, such that even a relatively small gap between the outer edge of the blade of the impeller and the inner surface of frame 34 (e.g., a gap that is as described above) is maintained, during rotation of the impeller, as described hereinabove. For some applications, axial shaft 92 is made of stainless steel, and proximal bearing 116 and/or distal bearing 118 are made of hardened steel. Typically, when crimping (i.e., radially constraining) the impeller and the frame for the purpose of inserting the impeller and the frame into the subject's body, distal bushing 58 of the impeller is configured to slide along the axial shaft in the distal direction, such that the impeller becomes axially elongated, as described hereinabove. More generally, the impeller changes from its radially-constrained configuration to its non-radially-constrained configuration, and vice versa, by the distal bushing sliding over the axial shaft.

Typically, the impeller itself is not directly disposed within any radial bearings or thrust bearings. Rather, bearings 116 and 118 act as radial bearings with respect to the axial shaft. For some applications, there is no thrust bearing in contact with any surface that could generate thrust forces during the rotation of the impeller, since the impeller is configured to move axially within frame 34, while the impeller is rotating, as described in further detail hereinbelow. Typically, pump portion 27 (and more generally ventricular assist device 20) does not include any thrust bearing that is configured to be disposed within the subject's body and that is configured to oppose thrust generated by the rotation of the impeller. For some applications, one or more thrust bearings are disposed outside the subject's body (e.g., within motor unit 23, shown in FIGS. 1A, 7, and 8A-B), and opposition to thrust generated by the rotation of the impeller is provided solely by the one or more thrust bearings disposed outside the subject's body. For some applications, a mechanical element and/or a magnetic element is configured to maintain the impeller within a given range of axial positions. For example, a magnet (e.g., magnet 82, described hereinbelow with reference to FIG. 7) that is disposed at the proximal end of the drive cable (e.g., outside the subject's body) may be configured to impart axial motion to the impeller, and to maintain the impeller within a given range of axial positions.

For some alternative applications of the present invention, a ventricular assist device includes an impeller that is not configured to move in an axial back-and-forth motion. For some such applications (not shown), a thrust bearing is used to maintain the axial position of the impeller, and the thrust bearing is disposed within a portion of the ventricular assist device that is proximal to the impeller, such that the thrust bearing does not come into contact with the subject's blood. For example, the thrust bearing may be disposed within an outer tube in which the drive shaft of the impeller is disposed. Alternatively or additionally, the thrust bearing may be disposed outside the subject's body. For some such applications, since the thrust bearing is disposed outside the subject's body, the thrust bearing's dimensions are not constrained by virtue of needing to be deployed within a small anatomical location. Therefore, in such cases, the contact area between the two opposing surfaces of the thrust bearing is typically greater than 20 square mm. For some applications (not shown), the thrust bearing is disposed distally to the impeller and in contact with the subject's blood, such that the thrust bearing is cooled by the subject's blood.

Reference is now made to FIGS. 6A and 6B, which are schematic illustrations of ventricular assist device 20 at respective stages of a motion cycle of impeller 50 of the ventricular assist device with respect to frame 34 of the ventricular assist device, in accordance with some applications of the present invention. For some applications, while the impeller is pumping blood through tube 24, by rotating, axial shaft 92 (to which the impeller is fixated) is driven to move the impeller axially back-and-forth within frame 34, by the axial shaft moving in an axial back-and-forth motion, as described in further detail hereinbelow with reference to FIG. 7. Alternatively or additionally, the impeller and the axial shaft are configured to move axially back-and-forth within frame 34 in response to forces that are acting upon the impeller, and without requiring the axial shaft to be actively driven to move in the axial back-and-forth motion, as described in further detail hereinbelow, for example, with reference to FIG. 9.

For some applications, by moving in the back-and-forth motion, the portions of the axial shaft that are in contact with proximal bearing 116 and distal bearing 118 are constantly changing. For some such applications, in this manner, the frictional force that is exerted upon the axial shaft by the bearings is spread over a larger area of the axial shaft than if the axial shaft were not to move relative to the bearings, thereby reducing wear upon the axial shaft, ceteris paribus. Alternatively or additionally, by moving in the back-and-forth motion with respect to the bearing, the axial shaft cleans the interface between the axial shaft and the bearings from any residues, such as blood residues.

For some applications, when frame 34 and impeller 50 are in non-radially-constrained configurations thereof (e.g., when the frame and the impeller are deployed within the left ventricle), the length of the frame exceeds the length of the impeller by at least 2 mm (e.g., at least 4 mm, or at least 8 mm). Typically, the proximal bearing 116 and distal bearing 118 are each 2-4 mm in length. Further typically, the impeller and the axial shaft are configured to move axially within the frame in the back-and-forth motion at least along the length of each of the proximal and distal bearings, or at least along twice the length of each of the bearings. Thus, during the back-and-forth axial movement of the axial shaft, the axial shaft is wiped clean on either side of each of the bearings.

Reference is again made to FIGS. 6A and 6B, and reference is also made to FIG. 6C, which is a schematic illustration of an axial-shaft-receiving tube 126 and a distal tip portion 120 of ventricular assist device 20, in accordance with some applications of the present invention. For some applications, the distal tip portion of the ventricular assist device is configured to be soft, such that the distal tip portion is configured not to injure tissue of the subject, even if the distal tip portion comes into contact with the tissue (e.g., tissue of the left ventricle). For example, the distal tip portion may be made of silicone. For some applications, the distal tip portion defines a lumen 122 therethrough. For some such applications, during insertion of the ventricular assist device into the left ventricle, guidewire 10 (FIG. 1B) is first inserted into the left ventricle, for example, in accordance with known techniques. The distal tip portion of the ventricular assist device is then guided to the left ventricle by advancing the distal tip portion over the guidewire, with the guidewire disposed inside lumen 122. For some applications, a hemostasis valve 152 is disposed at the distal end of the lumen 122 of distal tip portion 120, such that the distal tip portion becomes sealed after the guidewire is retracted from lumen 122. Typically, during the insertion of the ventricular assist device into the subject's ventricle, delivery catheter 143 is placed over impeller 50 and frame 34 and maintains the impeller and the frame in their radially-constrained configurations. For some applications, distal tip portion 120 extends distally from the delivery catheter during the insertion of the delivery catheter into the subject's ventricle. For some applications, at the proximal end of the distal tip portion, the distal tip portion has a flared portion 124 that acts as a stopper and prevents the delivery catheter from advancing beyond the flared portion.

For some applications, axial-shaft-receiving tube 126 extends proximally from distal tip portion 120. As described hereinabove, typically, the axial shaft undergoes axial back-and-forth motion during the operation of impeller 50. Shaft-receiving tube 126 defines lumen 127, which is configured to receive the axial shaft when the axial shaft extends beyond distal bearing 118. For some applications, the shaft-receiving tube defines a stopper 128 at its distal end, the stopper being configured to prevent advancement of the axial shaft beyond the stopper. For some applications, the stopper comprises a rigid component that is inserted (e.g., embedded into the distal end of the shaft-receiving tube. Alternatively, the stopper comprises a shoulder between lumen 127 of the axial-shaft-receiving tube and lumen 122 of tip portion 120. Typically, such a shoulder is present since lumen 122 of tip portion 120 is narrower than lumen 127. (This is because lumen 127 is typically configured to accommodate the axial shaft, while lumen 122 is configured to accommodate guidewire 10, and the axial shaft is typically wider than guidewire 10, since the axial shaft is itself configured to accommodate guidewire 10 within internal lumen 132 (shown in FIGS. 10B and 10C) of the axial shaft). Typically, during normal operation of the impeller, the axial shaft does not extend to stopper 128, even when drive cable 130 (shown in FIG. 7) is maximally elongated. However, stopper 128 is configured to prevent the axial shaft from protruding into the tip portion when the delivery catheter is advanced over impeller 50 and frame 34, during retraction of ventricular assist device 20 from the subject's ventricle. In some cases, during the advancement of the delivery catheter over the frame and the impeller, the drive cable is at risk of snapping. In the absence of stopper 128, in such cases the axial shaft may protrude into the tip portion. Stopper 128 prevents this from happening, even in the event that the drive cable snaps.

Typically, during operation of the ventricular assist device, and throughout the back-and-forth axial motion cycle of the impeller, the impeller is disposed in relatively close proximity to the distal tip portion. For example, the distance of the impeller to the distal tip portion may be within the distal-most 50 percent, e.g., the distal-most 30 percent (or the distal-most 20 percent) of tube 24, throughout the back-and-forth motion axial cycle of the impeller.

For some applications (not shown), a portion of frame 34 extends into a proximal portion of distal tip portion 120. The portion of the frame is configured to cause the proximal portion of the tip to undergo radial expansion upon being deployed within the subject's left ventricle, by the portion of the frame being shape set to a radially-expanded configuration. For some applications, the entire tip portion is made of a material having a uniform stiffness, but a portion of the frame 34 that extends into the proximal portion of the tip portion imparts rigidity to the proximal portion of the tip portion, such that the proximal portion of the tip portion has a greater rigidity than the distal portion of the tip portion.

For some applications, the tip portion has a different configuration to that shown in FIG. 6C, as described in further detail hereinbelow, for example, with reference to FIGS. 18-24B. For some applications, the distal tip portion combines certain features described with respect to FIG. 6C with features described hereinbelow, for example, with reference to FIG. 13 and to FIGS. 18-24B. For example, the internal structure of the tip portion and the proximal extension of axial-shaft-receiving tube 126 from the tip portion may be as described with reference to FIG. 6 and/or FIG. 13, and the external shape of the tip portion may be as described with reference to any one of FIGS. 18-24B.

Figure 7:
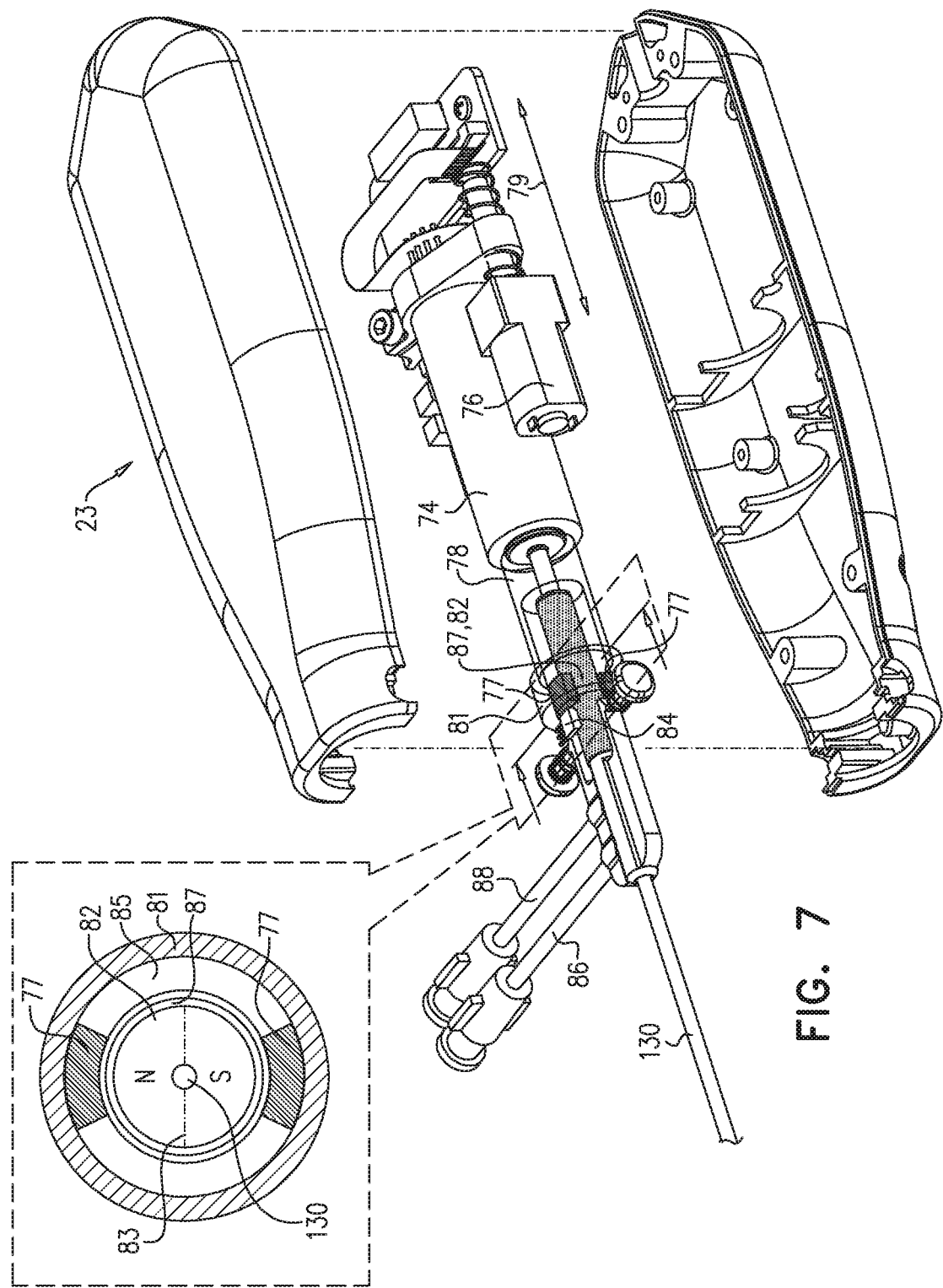
FIG. 7 is a schematic illustration of a motor unit of a ventricular assist device, in accordance with some applications of the present invention.
Figure 8:
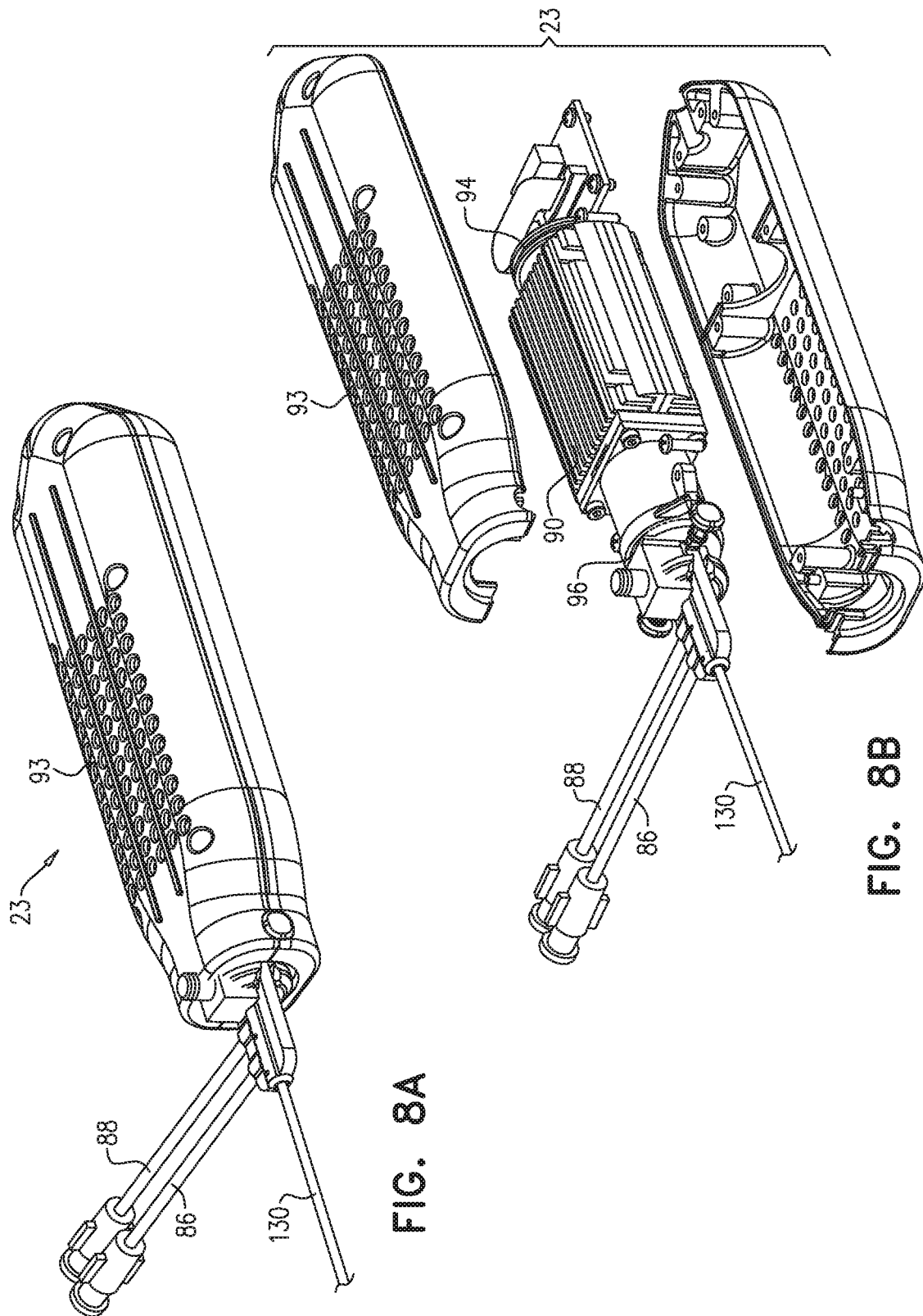
FIGS. 8A and 8B are schematic illustrations of a motor unit of a ventricular assist device, in accordance with some applications of the present invention.

Reference is now made to FIG. 7, which is a schematic illustration of an exploded view of motor unit 23 of ventricular assist device 20, in accordance with some applications of the present invention. For some applications, computer processor 25 of control console 21 (FIG. 1A) that controls the rotation of impeller 50 is also configured to control the back-and-forth motion of the axial shaft. Typically, both types of motion are generated using motor unit 23. The scope of the present invention includes controlling the back-and-forth motion at any frequency. For some applications, an indication of the subject's cardiac cycle is detected (e.g., by detecting the subject's ECG), and the back-and-forth motion of the axial shaft is synchronized to the subject's cardiac cycle.

Typically, motor unit 23 includes a motor 74 that is configured to impart rotational motion to impeller 50, via drive cable 130. As described in further detail hereinbelow, typically, the motor is magnetically coupled to the drive cable. For some applications, an axial motion driver 76 is configured to drive the motor to move in an axial back-and-forth motion, as indicated by double-headed arrow 79. Typically, by virtue of the magnetic coupling of the motor to the drive cable, the motor imparts the back-and-forth motion to the drive cable, which it turn imparts this motion to the impeller. As described hereinbelow, for some applications, the drive cable, the impeller, and/or the axial shaft undergo axial back-and-forth motion in a passive manner, e.g., due to cyclical changes in the pressure gradient against which the impeller is pumping blood. Typically, for such applications, motor unit 23 does not include axial motion driver 76.

For some applications, the magnetic coupling of the motor to the drive cable is as shown in FIG. 7. As shown in FIG. 7, a set of driving magnets 77 are coupled to the motor via a driving magnet housing 78. For some applications, the driving magnet housing includes ring 81 (e.g., a steel ring), and the driving magnets are adhered to an inner surface of the ring. For some applications a spacer 85 is adhered to the inner surface of ring 81, between the two driving magnets, as shown. A driven magnet 82 is disposed between the driving magnets such that there is axial overlap between the driving magnets and the driven magnet, and is coupled to the proximal end of drive cable 130. For example, the driven magnet may be cylindrical and define a hole therethrough, and the proximal end of the drive cable may be adhered to an inner surface of the driven magnet that defines the hole. For some applications, the driven magnet is cylindrical, and the magnet includes a North pole and a South pole, which are divided from each other along the length of the cylinder along a line 83 that bisects the cylinder, as shown. For some applications, the driven magnet is housed inside a cylindrical housing 87.

Magnetic coupling is strongest when the field density is maximized Therefore, it is desirable to use relatively strong magnets for the driving magnets and the driven magnet, to have a small air gap between the driving magnets and the driven magnet, and to try to minimize field line leakage. Typically, the driving magnets and the driven magnet are neodymium magnets, which are relatively strong. Further typically, the gap between each of the driving magnets and the driven magnet is less than 2 mm, e g, approximately 1 mm. In order to reduce field line leakage, typically fewer than 4 magnets (e.g., exactly two magnets, as shown) are used as the driving magnets, for the following reason.

Typically, it is desirable to minimize the diameter of the driven magnet, for example, in order to stabilize the driven magnet. As described hereinabove, the driven magnet is cylindrical, and the magnet includes a North pole and a South pole, which are divided from each other along the length of the cylinder along dividing line 83. In the region of the circumference of the driven magnet that is closest to the dividing line between the North and South poles of the magnet, the magnetic field lines pass directly from the North of the magnet to the South rather than crossing the air gap to the first outer magnet, passing through the outer magnet, around ring 81, and across the second driving magnet back to the South pole of the driven magnet. As an approximation, any field line which can be drawn between the North pole and the South pole, the length of which is less than at least the total sum of the air gaps between the driven magnet and the driving magnets will pass from the North pole of the driven magnet to the South pole of the driven magnet rather than taking the alternative route. Assuming that this adds up to all field lines extending around 2 mm of the circumference of the driven magnet on either side of the dividing line between the North and South poles of the driven magnet, that is a total of 4 mm out of the total circumference of the driven magnet that does not contribute toward the magnetic coupling between the driving magnets and the driven magnet. If instead of just two poles, the driven magnet had four poles, and correspondingly there were four driving magnets, then there would be 2-mm-long wasted circumference sections four times throughout the circumference, which would result in a total of 8 mm out of 12 mm of the circumference of the inner magnet with wasted field lines. Some of this loss would be compensated by the addition of two extra driving magnets, which add to the field strength. However, the additional outer magnets would be relatively close to each other, which would result in magnetic field leaking between the driving magnets. In view of the above, typically, the motor unit includes fewer than 4 magnets (e.g., exactly two magnets, as shown) as driving magnets, and the driven magnet is divided into fewer than four poles (e.g., exactly two poles, as shown).

It is noted that in the application shown in FIG. 7, the driving magnets are disposed outside the driven magnet. However, the scope of the present application includes reversing the configurations of the driving magnets and the driven magnet, mutatis mutandis. For example, the proximal end of the drive cable may be coupled to two or more driven magnets, which are disposed around a driving magnet, such that there is axial overlap between the driven magnets and the driving magnet. The above discussion regarding the number of magnets that should be used as the outer magnets, and the number of poles into which the inner magnet should be divided, is equally applicable to such a configuration. Namely, that for such a configuration, typically, the motor unit includes fewer than 4 magnets (e.g., exactly two magnets, as shown) as driven magnets, and the driving magnet is divided into fewer than four poles (e.g., exactly two poles, as shown).

As described hereinabove, typically purging system 29 (shown in FIG. 1A) is used with ventricular assist device 20. Typically, motor unit 23 includes an inlet port 86 and an outlet port 88, for use with the purging system. For some applications, a purging fluid is continuously or periodically pumped into the ventricular assist device via inlet port 86 and out of the ventricular assist device via outlet port 88. For some applications, the purging fluid is pumped into the ventricular assist device and the inlet and outlet ports are placed in fluid communication with each other, such that a given volume of purging fluid circulates within the device for a period of time. Additional aspects of the purging system are described hereinbelow.

Reference is now made to FIGS. 8A and 8B, which are schematic illustrations of motor unit 23, in accordance with some applications of the present invention. In general, motor unit 23 as shown in FIGS. 8A and 8B is similar to that shown in FIG. 7, and unless described otherwise, motor unit 23 as shown in FIGS. 8A and 8B contains similar components to motor unit 23 as shown in FIG. 7. For some applications, the motor unit includes a heat sink 90 that is configured to dissipate heat that is generated by the motor. Alternatively or additionally, the motor unit includes ventilation ports 93 that are configured to facilitate the dissipation of heat that is generated by the motor. For some applications, the motor unit includes vibration dampeners 94 and 96 that are configured to dampen vibration of the motor unit that is caused by rotational motion and/or axial back-and-forth motion of components of the ventricular assist device.

For some applications, impeller 50 and axial shaft 92 are configured to move axially back-and-forth within frame 34 in response to forces that act upon the impeller, and without requiring the axial shaft to be actively driven to move in the axial back-and-forth motion. Typically, over the course of the subject's cardiac cycle, the pressure difference between the left ventricle and the aorta varies from being approximately zero during ventricular systole (hereinafter "systole") to a relatively large pressure difference (e.g., 60-100 mmHg) during ventricular diastole (hereinafter "diastole"). For some applications, due to the increased pressure difference that the impeller is pumping against during diastole, the impeller is pushed distally with respect to frame 34 during diastole, relative to the location of the impeller with respect to frame 34 during systole. In turn, since the impeller is connected to the axial shaft, the axial shaft is moved forward. During systole, the impeller (and, in turn, the axial shaft) move back to their systolic positions. In this manner, the axial back-and-forth motion of the impeller and the axial shaft is generated in a passive manner, i.e., without requiring active driving of the axial shaft and the impeller, in order to cause them to undergo this motion.

Figure 9:
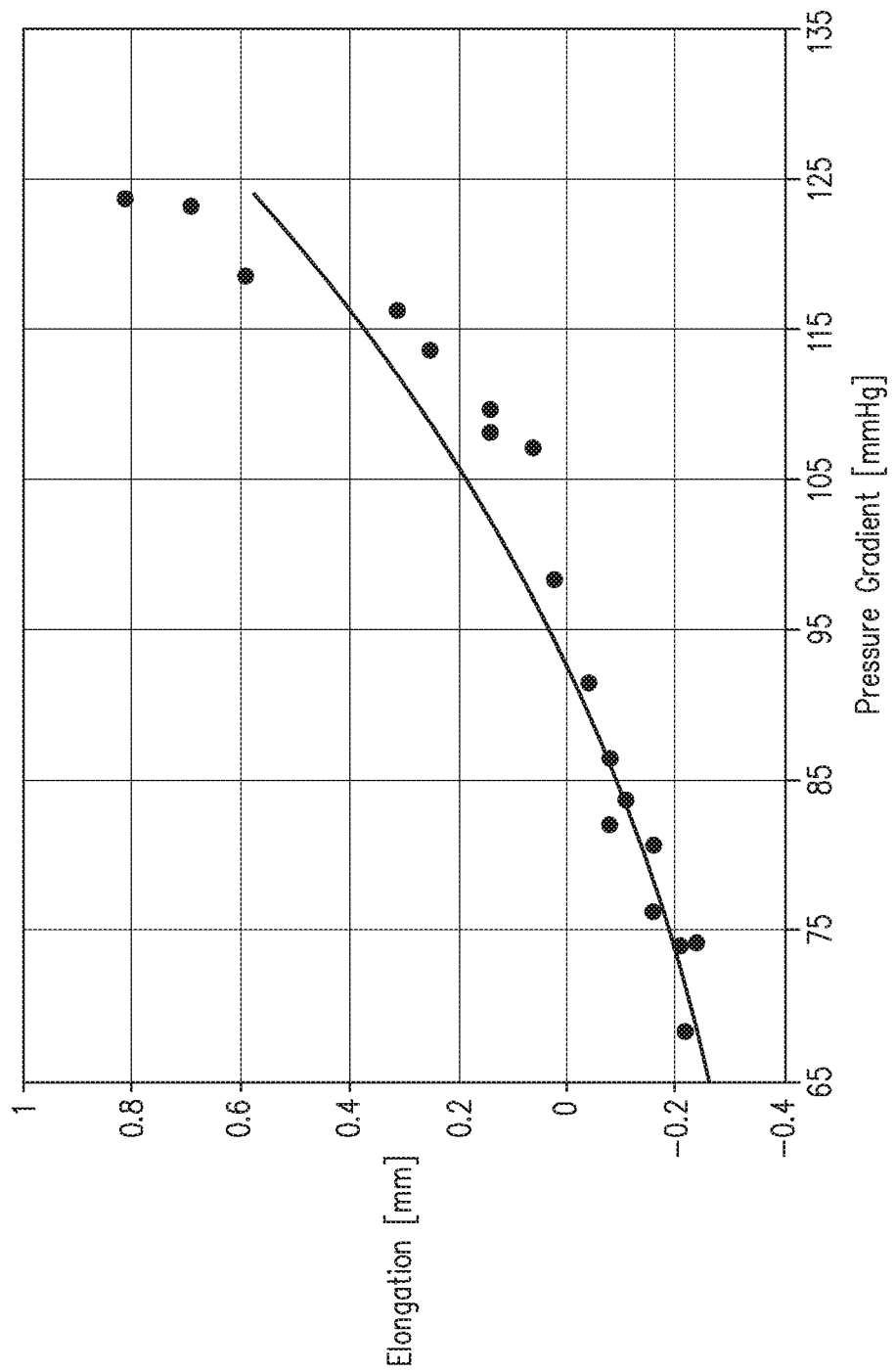
FIG. 9 is a graph indicating variations in the length of a drive cable of a ventricular assist device as a pressure gradient against which the impeller of the blood pump varies, as measured in experiments performed by the inventors of the present application.

Reference is now made to FIG. 9, which is a graph indicating variations in the length of a drive cable of a ventricular assist device, as a pressure gradient against which the impeller of the ventricular assist device varies, as measured in experiments performed by inventors of the present application. An impeller and a drive cable as described herein were used to pump a glycerin-based solution through chambers, with the chambers set up to replicate the left ventricle and the aorta, and the solution having properties (such as, density and viscosity) similar to those of blood. The pressure gradient against which the impeller was pumping varied, due to an increasing volume of fluid being disposed within the chamber into which the impeller was pumping. At the same time, movement of the drive cable was imaged and changes in the length of the drive cable were determined via machine-vision analysis of the images. The graph shown in FIG. 9 indicates the changes in the length of the drive cable that were measured, as a function of the pressure gradient. The y-axis of the graph shown in FIG. 9 is such that 0 mm elongation represents the length of the drive cable when the impeller is at rest. It is noted that the graph starts at a pressure gradient value of 65 mmHg, and that at this pressure the elongation is negative (at approximately −0.25 mm), i.e., the drive cable is shortened relative to the length of the drive cable prior to initiation of rotation of the impeller. This is because the drive cable was configured such that, when the impeller first started pumping, the drive cable shortened (relative to the length of the drive cable before the impeller was activated), due to coils within the drive cable unwinding, as described in further detail hereinbelow. As seen in the section of the curve that is shown in FIG. 9, after the initial shortening of the drive cable that resulted from the aforementioned effect, it was then the case that as the pressure gradient increased, the drive cable became increasingly elongated.

As indicated by the results shown in FIG. 9 and as described hereinabove, it is typically the case that, in response to variations in the pressure against which the impeller is pumping blood (e.g., the pressure difference between the left ventricle and the aorta), the impeller moves back and forth with respect to frame 34. In turn, the movement of the impeller causes drive cable 130 to become more or less elongated.

For some applications, during operation of the ventricular assist device, computer processor 25 of control console 21 (FIG. 1A) is configured to measure an indication of the pressure exerted upon the impeller (which is indicative of the pressure difference between the left ventricle and the aorta), by measuring an indication of tension in drive cable 130, and/or axial motion of the drive cable. For some applications, based upon the measured indication, the computer processor detects events in the subject's cardiac cycle, determines the subject's left-ventricular pressure, and/or determines the subject's cardiac afterload. For some applications, the computer processor controls the rotation of the impeller, and/or the axial back-and-forth motion of the axial shaft in response thereto.

For some applications, generally similar techniques are applied to a right ventricular assist device that is configured to pump blood from the right ventricle to the pulmonary artery, and the computer processor is configured to determine the pressure difference between the right ventricle and the pulmonary artery in a generally similar manner, mutatis mutandis. For some applications, generally similar techniques are applied to a cardiac assist device that is configured to pump blood from a first location to a second location (such as, from the vena cava to the right ventricle, from the right atrium to the right ventricle, from the vena cava to the pulmonary artery, and/or from right atrium to the pulmonary artery), and the computer processor is configured to determine the pressure difference between the first location and the second location in a generally similar manner, mutatis mutandis.

Referring again to FIG. 7, for some applications, ventricular assist device 20 includes a sensor 84. For example, the sensor may include a Hall sensor that is disposed within motor unit 23, as shown in FIG. 7. For some applications, the Hall sensor measures variations in the magnetic field that is generated by one of the magnets in order to measure the axial motion of drive cable 130, and, in turn, to determine the pressure against which the impeller is pumping. For example, the inner, driven magnet 82 may be axially longer than the outer, driving magnets 77. Due to the inner magnet being longer than the outer magnets, there are magnetic field lines that emanate from the inner magnet that do not pass to the outer magnets, and the magnetic flux generated by those field lines, as measured by the Hall sensor, varies as the drive cable, and, in turn, the inner magnet moves axially. During operation, motor 74 rotates, creating an AC signal in the Hall sensor, which typically has a frequency of between 200 Hz and 800 Hz. Typically, as the tension in the drive cable changes due to the subject's cardiac cycle, this gives rise to a low frequency envelope in the signal measured by the Hall sensor, the low frequency envelope typically having a frequency of 0.5-2 Hz. For some applications, the computer processor measures the low frequency envelope, and derives the subject's cardiac cycle from the measured envelope. It is noted that typically the axial motion of the magnet is substantially less than that of the impeller, since the full range of motion of the impeller isn't transmitted along the length of the drive cable. However, it is typically the case that the axial back-and-forth motion of the impeller gives rise to a measurable back-and-forth motion of the magnet.

For some applications, the Hall sensor measurements are initially calibrated, such that the change in magnetic flux per unit change in pressure against which the impeller is pumping (i.e., per unit change in the pressure difference between the left ventricle and the aorta) is known. It is known that, in most subjects, at systole, the left-ventricular pressure is equal to the aortic pressure. Therefore, for some applications, the subject's aortic pressure is measured, and the subject's left-ventricular pressure at a given time is then calculated by the computer processor, based upon (a) the measured aortic pressure, and (b) the difference between the magnetic flux measured by the Hall sensor at that time, and the magnetic flux measured by the Hall sensor during systole (when the pressure in the left ventricle is assumed to be equal to that of the aorta).

Figure 10A:
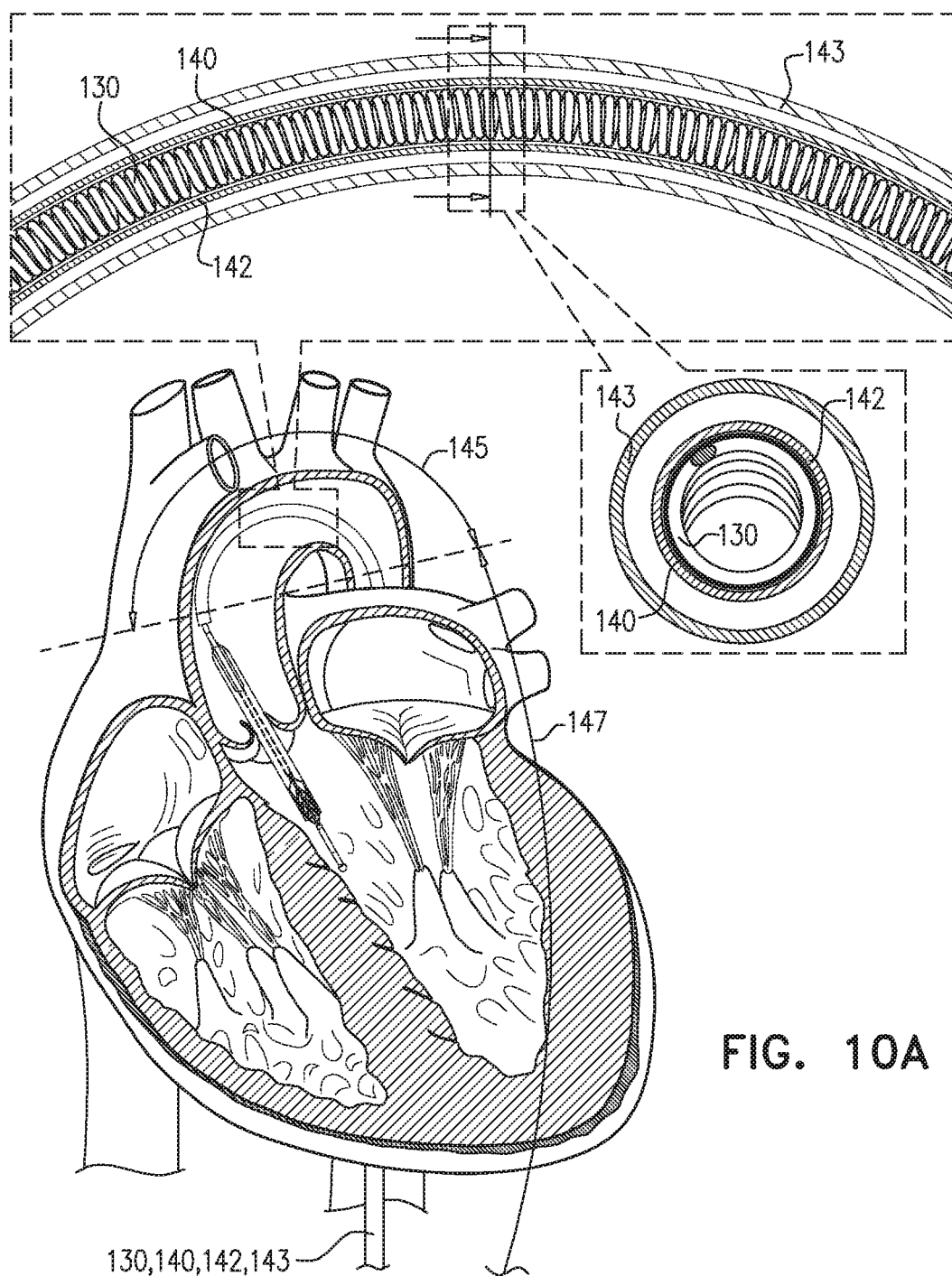

Reference is now made to FIGS. 10A, 10B, and 10C, which are schematic illustrations of drive cable 130 of ventricular assist device 20, in accordance with some applications of the present invention. Typically, the rotational motion of the impeller (which is imparted via the axial shaft), as well as the axial back-and-forth motion of the axial shaft described hereinabove, is imparted to the axial shaft via the drive cable, as described hereinabove. Typically, the drive cable extends from motor unit 23 (which is typically disposed outside the subject's body) to the proximal end of axial shaft 92 (as shown in FIG. 10C, which shows the connection between the distal end of the drive cable and the proximal end of the axial shaft). For some applications, the drive cable includes a plurality of wires 134 that are disposed in a tightly-coiled configuration in order to impart sufficient strength and flexibility to the drive cable, such that a portion of the cable is able to be maintained within the aortic arch (the portion corresponding to arrow 145 in FIG. 10A), while the cable is rotating and moving in the axial back-and-forth motion. The drive cable is typically disposed within a first outer tube 140, which is configured to remain stationary while the drive cable undergoes rotational and/or axial back-and-forth motion. The first outer tube is configured to effectively act as a bearing along the length of the drive cable. Typically, the first outer tube is made of a polymer (such as, polyether ether ketone) that is configured to be highly resistant to fatigue even under the frictional forces that are generated by the relative motion between the drive cable and the first outer tube. However, since such polymers are typically relatively rigid, only a thin layer of the polymer is typically used in the first outer tube. For some applications, the first outer tube is disposed within a second outer tube 142, which is made of a material having greater flexibility than that of the first outer tube (e.g., nylon, and/or polyether block amide), and the thickness of the second outer tube is greater than that of the first outer tube.

Typically, during insertion of the impeller and the cage into the left ventricle, impeller 50 and frame 34 are maintained in a radially-constrained configuration by delivery catheter 143. As described hereinabove, in order for the impeller and the frame to assume non-radially-constrained configurations, the delivery catheter is retracted. For some applications, as shown in FIG. 10A, the delivery catheter remains in the subject's aorta during operation of the left ventricular device, and outer tube 142 is disposed inside the delivery catheter. In order to retract the left ventricular device from the subject's body, the delivery catheter is advanced over the impeller and the frame, such that the impeller and the frame assume their radially-constrained configurations. The catheter is then withdrawn from the subject's body.

Referring to FIG. 10C, typically, the axial shaft and the cable define a continuous lumen 132 therethrough. For some applications, the left ventricular device is guided to the aorta and to the left ventricle by placing the axial shaft and the cable over guidewire 10 (described hereinabove), such that the guidewire is disposed inside lumen 132. For some applications, by using the lumen of the axial shaft and the cable in this manner, it is not necessary to provide an additional guidewire guide to be used during insertion of left ventricular assist device 20. For some applications, the axial shaft and the cable each have outer diameters of more than 0.6 mm (e.g., more than 0.8 mm), and/or less than 1.2 mm (e.g., less than 1 mm), e.g., 0.6-1.2 mm, or 0.8-1 mm. For some applications, the diameter of lumen 132, defined by the shaft and the cable, is more than 0.3 mm (e.g., more than 0.4 mm), and/or less than 0.7 mm (e.g., less than 0.6 mm), e.g., 0.3-0.7 mm, or 0.4-0.6 mm. For some applications, drive cable 130 has a total length of more than 1 m (e.g., more than 1.1 m), and/or less than 1.4 m (e.g., less than 1.3 m), e.g., 1-1.4 m, or 1.1-1.3 m. As described hereinabove, for some applications, the guidewire additionally passes through lumen 122 of distal tip portion 120. Typically, the diameter of lumen 122 is generally similar to that of lumen 132.

Referring to FIG. 10B, for some applications, drive cable 130 is made up of a plurality of coiled wires 134. Typically, due to the impeller having to pump against a pressure gradient during diastole, the impeller is pushed distally with respect to frame 34, relative to the position of the impeller with respect to the frame during systole, as described hereinabove. If the direction of rotation of the impeller is such that rotation of the drive cable in this direction results in the coiled wires of the drive cable at least partially tightening, then this would also cause the impeller to advance with respect to the frame when the rotation of the impeller is initiated, due to the coiled wires tightening (i.e., becoming wound up such that the radius of the coil decreases), and thereby axially elongating. For some applications, at least a portion of the drive cable is configured such that (a) in response to the impeller pumping blood from the left ventricle to the aorta, by rotating in a predefined direction of rotation, (b) rotation of the drive cable in this direction results in the coiled wires of the drive cable along the portion of the drive cable at least partially unwinding, such that the portion of the drive cable axially shortens. By configuring the drive cable in the aforementioned manner, the length of frame 34 does not need to accommodate distal movement of the impeller resulting from the drive cable axially elongating, in addition to accommodating the distal movement of the impeller within the frame resulting from the changes in pressure due to the subject's cardiac cycle (as described hereinabove). For some applications, the extent to which the drive cable is able to unwind and thereby axially shorten is limited by the outer tube in which the drive cable is disposed preventing the drive cable from radially expanding. Therefore, for some applications, the axial shortening of the drive cable is by a relatively small amount. For some applications, due to the outer tube limiting the extent to which the drive cable is able to unwind and thereby axially shorten, the drive cable doesn't shorten. However, even in such applications, the drive cable is typically configured not to elongate, due to the windings of the coil being configured as described hereinabove.

Alternatively or additionally, the impeller is inserted into frame 34, such that the drive cable is already in a preloaded state (i.e., such that the impeller exerts tension on the drive cable that causes the drive cable to be axially elongated relative to its rest state). Due to the preloading of the drive cable, when the rotation of the impeller is initiated, this does not cause the drive cable to axially elongate, since the drive cable is already in an axially elongated state relative to its rest state. For some such applications, the impeller is still configured to undergo axial back-and-forth motion as a result of changes in pressure due to the subject's cardiac cycle (as described hereinabove).

For some applications, debris is generated by frictional forces between the drive cable and outer tube 140. Alternatively or additionally, a fluid (e.g., purging fluid) is disposed between the drive cable and the outer tube. Typically, due to the windings of the coiled drive cable, the drive cable acts as an impeller and pumps the debris and/or the fluid axially with respect to outer tube 140. For some applications, the direction of the windings of the drive cable is such that the drive cable is configured, by rotating in a predefined rotation direction, to pump the debris and/or the fluid toward a proximal end of the ventricular assist device, and not to pump the debris and/or the fluid toward the distal end of the ventricular assist device toward the patient's left ventricle.

Reference is now made to FIGS. 11A and 11B, which are schematic illustrations of an interface component 154 that forms an interface between respective portions of drive cable 130 of ventricular assist device 20, in accordance with some applications of the present invention. For some applications, the drive cable includes first and second portions. Reference is also again made to FIG. 10A, typically, the first portion is configured to be disposed in the subject's aortic arch (i.e., the portion of the aorta corresponding to arrow 145), and the second portion is configured to be disposed along the descending aorta (the portion of the aorta corresponding to arrow 147), and typically to extend until motor unit 23, outside the subject's body. Typically, at locations at which drive cable 130 undergoes substantial curvature, such as the aortic arch, it is desirable for the drive cable to be relatively flexible. However, a drive cable having greater flexibility is typically also more axially stretchable than a drive cable having less flexibility. Therefore, for some applications, there is a tradeoff between wanting the drive cable being flexible enough to conform to the curvature of the aortic arch, but on the other hand not wanting the drive cable to undergo substantial axial stretching (which may result in a loss of control over the axial positions of the impeller). For some applications, the respective portions of the drive cable have respective levels of flexibility. For example, the first portion of the drive cable that is configured to be disposed in the aortic arch may have a first flexibility, while the second portion of the drive cable that is configured to be disposed in the descending aorta may have a second flexibility, the first flexibility being greater than the second flexibility.

For some applications, the first portion is configured to have greater flexibility than the second portion, by the coil of wires 134 in the first portion including fewer wires than in the second portion. For example, as shown in FIGS. 11A-B, the first portion may include more than 4 wires and fewer than 8 wires (e.g., 4-8 wires, or 5-7 wires, e.g., 6 wires), and the second portion may include more than 8 wires and fewer than 12 wires (e.g., 8-12 wires, or 9-11 wires, e.g., 10 wires). For some applications, the length of the first portion of the drive cable is more than 20 cm (e.g., more than 25 cm) and less than 40 cm (e.g., less than 35 cm), e.g., 20-40 cm, or 25-35 cm. For some applications, the length of the second portion of the drive cable is more than 60 cm (e.g., more than 70 cm) and less than 100 cm (e.g., less than 90 cm), e.g., 60-100 cm, or 70-90 cm.

For some applications, the two portions of the drive cable are coupled to each other via interface component 154. Typically, the wires of the two portions are welded to the interface component. For some applications, grooves 157 are cut into the interface component. The grooves are configured such that stress generated by a wire at the interface is spread over the radius of the groove as opposed to being concentrated at the point at which the wire is welded to the interface component. For some such applications, the interface component additionally includes protrusions 158 that hold the wires in place during welding of the wires to the interface component.

Reference is now made to FIGS. 11C, 11D, and 11E, which are schematic illustrations of an interface 156 between the drive cable and axial shaft 92 of the ventricular assist device, in accordance with some applications of the present invention. For some applications, generally similar techniques to those described with reference to FIGS. 11A-B are used to couple the drive cable to the axial shaft. For some applications, the proximal end of the axial shaft (which defines interface 156) includes grooves 157 and/or protrusions 158, which are generally as described hereinabove, and which are shown in FIG. 11C.

Referring to FIG. 11D, for some applications, as the coiled wires approach interface 156, the coiled wires are at least partially straightened (i.e., the pitch of the wires is increased), such that the angle that the wires make with the interface is less acute than it would be if the wire were not straightened. By making the angle less acute, stress at the point at which the wires are welded to the interface component is reduced. Referring to FIG. 11E, for some applications, as the wires approach interface 156, in addition to being straightened, the wires are flattened and pushed radially inward. For some applications, the wires are sufficiently flattened that each of the wires in the coil come into contact with adjacent wires thereto, such as to form a cylinder, as shown. For example, the shapes of the wires may be changed from having a circular cross-section with a radius of approximately 0.2 mm to an elliptical cross-section having a minor axis of 0.12 mm. For some applications, the flattening is performed along a length of between 1 mm and 3 mm. For some applications, the wires are flattened by placing an overtube 159 around the wires, placing the overtube and the wires on a mandrel, and squeezing the overtube and the wires radially inward. Subsequently, the overtube and the flattened wires are welded to axial shaft 92 at the interface.

For some applications, generally similar techniques to those described with reference to FIGS. 11D and 11E are used for coupling the two portions of the drive cable to each other. For some applications, as the coiled wires approach interface component 154, the coiled wires are at least partially straightened (i.e., the pitch of the wires is increased), such that the angle that the wires make with the interface is less acute than it would be if the wires were not straightened. By making the angle less acute, stress at the point at which the wires are welded to the interface component is reduced. For some applications, as the wires approach interface component 154, in addition to being straightened, the wires are flattened and pushed radially inward. For some applications, the wires are sufficiently flattened that each of the wires in the coil come into contact with adjacent wires thereto, such as to form a cylinder. For example, the shapes of the wires may be changes from having a circular cross-section with a radius of approximately 0.2 mm to an elliptical cross-section having a minor axis of 0.12 mm. For some applications, the flattening is performed along a length of between 1 mm and 3 mm. For some applications, the wires are flattened by placing an overtube (not shown, but similar to overtube 159) around the wires, placing the overtube and the wires on a mandrel, and squeezing the overtube and the wires radially inward. Subsequently, the overtube and the flattened wires are welded to interface component 154.

For some applications, swaging techniques are used for coupling the two portions of the drive cable to each other. For some such applications, the ends of inner and outer tubes are placed respectively inside and outside of the ends of the two portions of the drive cable that will form the interface between the portions. The inner tube is then placed over a rigid mandrel and the inner and outer tubes and the ends of the drive cable are swaged together by applying pressure around the outside of the outer tube. Once the ends of the portions of the drive cable, as well as the inner and outer tubes, have been swaged together, this forms the interface between the portions of the drive cable. For some applications, similar swaging techniques are performed for coupling the drive cable to the axial shaft at interface 156.

Figure 12:
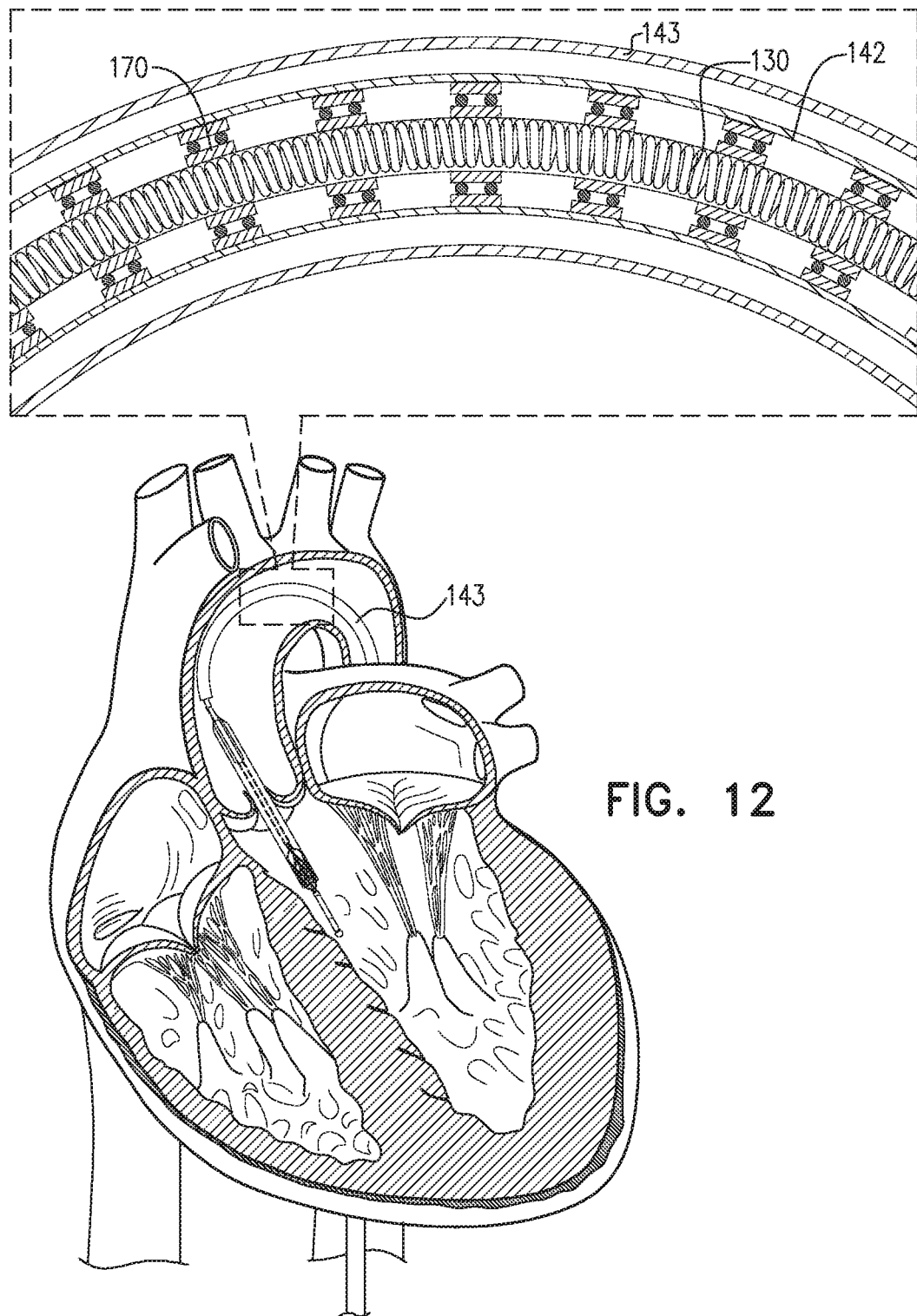
FIG. 12 is a schematic illustration of a drive cable of a ventricular assist device that includes friction-reduction elements disposed around at least a portion of the drive cable, in accordance with some applications of the present invention.

Reference is now made to FIG. 12, which is a schematic illustration of drive cable 130 of ventricular assist device 20 that includes friction-reduction elements 170 disposed around at least a portion of the drive cable, in accordance with some applications of the present invention. For some applications, friction-reduction elements 170 are used to reduce friction between drive cable 130 (which rotates during the operation of the ventricular assist device) and outer tube 142 (which remains stationary during the rotation of the drive cable). In the example shown, friction-reduction elements 170 are ball bearings. However, the scope of the present invention includes using other friction-reduction elements to reduce friction between the drive cable and the outer tube. For example, other rolling-element bearings may be used, such as cylindrical rollers, spherical rollers, gear bearings, tapered rollers, needle rollers, and/or toroidal roller bearings. For some applications, friction-reduction elements are used as an alternative to including first outer tube 140 in addition to second outer tube 142. In the example shown in FIG. 12, the friction-reduction elements are disposed between the drive cable and the second outer tube, and the ventricular assist device does not include first and second outer tubes.

Typically, the ventricular assist device traverses the subject's aortic arch, and/or other portions of the subject's vasculature that are substantially curved. In the absence of the friction-reduction elements, drive cable 130 and tube 142 would typically contact each other, particularly at the curved portions of the vasculature. As described hereinabove, drive cable 130 typically undergoes rotational motion, and for some applications additionally undergoes back-and-forth axial motion, with respect to tube 142. Therefore, in the absence of the friction-reduction elements (or first outer tube 140, as described hereinabove), there would be substantial frictional forces generated at the locations at which the drive cable and outer tube 142 are in contact with each other. Therefore, for some applications, the friction-reduction elements are disposed between drive cable 130 and outer tube 142, in order to reduce frictional forces generated at the locations at which drive cable 130 and outer tube 142 are in contact with each other. For some applications, the friction-reduction elements are disposed between drive cable 130 and outer tube 142 substantially along the full length of drive cable 130 and outer tube 142. Alternatively, the friction-reduction elements are disposed between drive cable 130 and outer tube 142 at locations at which drive cable 130 and outer tube 142 are configured to be substantially curved, e.g., at the location at which drive cable 130 and outer tube 142 are disposed within the aortic arch, during operation of the ventricular assist device.

Figure 13:
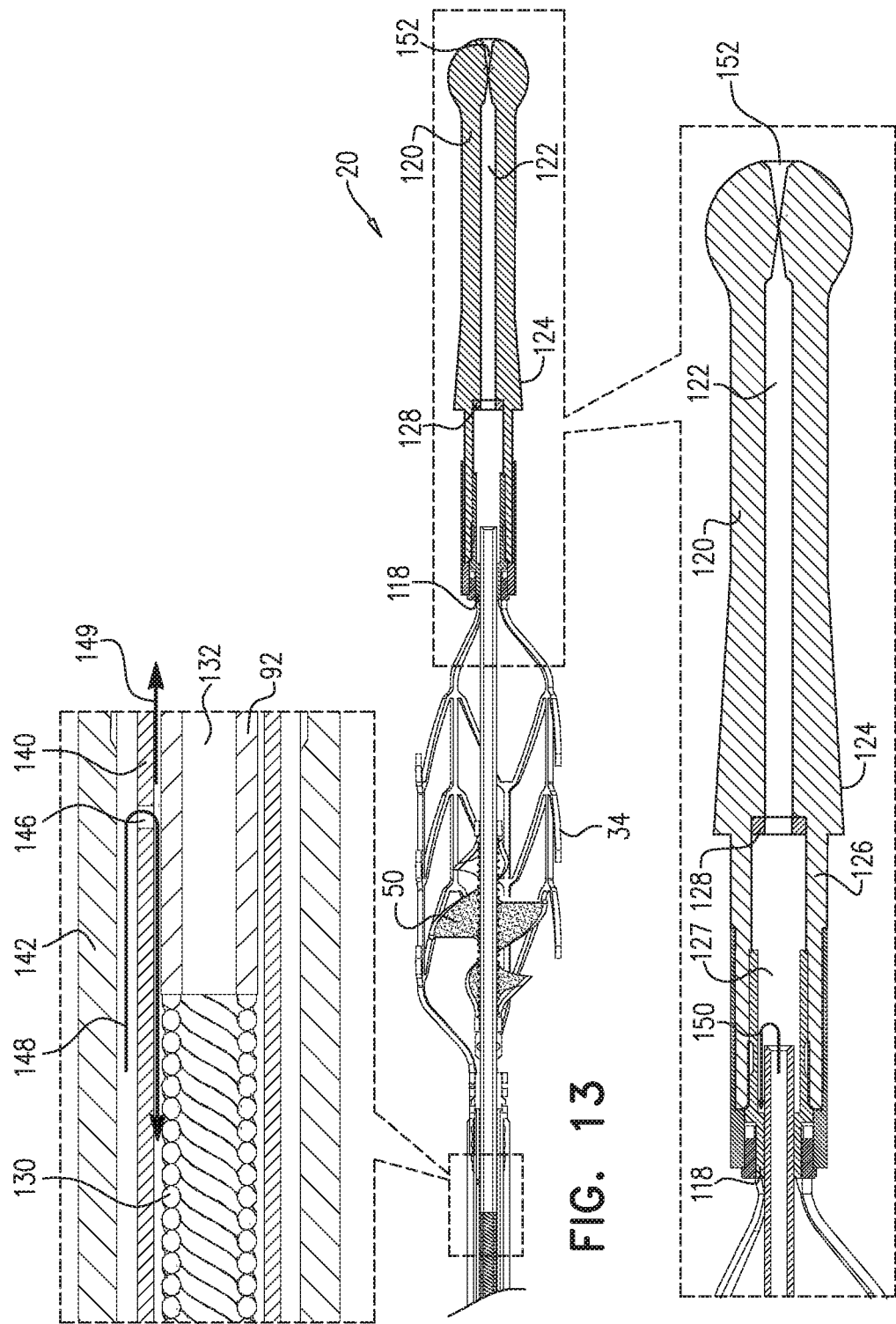
FIG. 13 is a schematic illustration of a procedure for purging a drive cable and/or radial bearings of a ventricular assist device, in accordance with some applications of the present invention.

Reference is now made to FIG. 13, which is a schematic illustration of a procedure for purging drive cable 130 of ventricular assist device 20, in accordance with some applications of the present invention. For some applications, proximal to proximal bearing 116, axial shaft 92 and cable 130 are surrounded by first and second outer tubes 140 and 142, as described hereinabove. Typically, both the first and second outer tubes remain stationary, during rotation of the drive cable. For some applications, a purging fluid (e.g., a fluid containing glucose or dextrose) is pumped between the first and second outer tubes, and there is an opening 146 within the first outer tube in the vicinity of the proximal bearing. As described hereinabove, typically purging system 29 (shown in FIG. 1A) controls the flow of the purging fluid via inlet port 86 and outlet port 88 (shown in FIGS. 7, 8A, and 8B). For some applications, the purging fluid flows between drive cable 130, and first outer tube 140, as indicated by purging-fluid-flow arrow 148 in FIG. 13. In this manner, the interface between drive cable 130 (which rotates), and outer tube 140 (which remains stationary, during rotation of the drive cable) is purged. For some applications, some of the purging fluid additionally flows to the interface between the axial shaft and proximal bearing 116, thereby purging the interface, as indicated by purging-fluid-flow arrow 149 in FIG. 13.

For some applications, purging fluid is pumped through lumen 132 defined by drive cable 130 and axial shaft 92, such that at least some fluid flows all the way to the distal end of the axial shaft. For some applications, in this manner, some of the purging fluid flows to the interface between the axial shaft and distal bearing 118, thereby purging the interface, as indicated by purging-fluid-flow arrow 150 in FIG. 13.

For some applications, hemostasis valve 152 is disposed at the distal end of the lumen 122 of distal tip portion 120, as described hereinabove. Alternatively or additionally, a plug (not shown) is disposed at the distal end of the lumen 122 of tip portion 120. Typically, the hemostasis valve and/or the plug prevents blood from flowing into lumen 122, and/or into lumen 132. Further typically, the plug, by preventing purging fluid from flowing out of the distal end of lumen 122, causes the purging fluid to flow toward the interface between axial shaft 92 and distal bearing 118, as indicated by purging-fluid-flow arrow 150 in FIG. 13.

For some applications, alternative techniques to those described hereinabove are used for introducing fluid (e.g., a fluid containing glucose) to the ventricular assist device. In the application shown in FIG. 13, fluid is allowed to flow distally after passing through opening 146, as indicated by arrow 149, and as described hereinabove. However, for some applications, flow of the fluid in the distal direction is blocked (i.e., the flow of fluid indicated by arrow 149 is absent). For some such applications, fluid is initially released into the space between drive cable 130 (which rotates), and outer tube 140 (which remains stationary, during rotation of the drive cable), such that the fluid fills the space between the drive cable and outer tube 140, proximal to opening 146. For example, the fluid may be pumped into the space via the gap between first outer tube 140 and second outer tube 142, as shown. The fluid is then kept in place, between the drive cable and outer tube 140, proximal to opening 146, typically, throughout the operation of the ventricular assist device. The fluid is configured to remove air from the space between the drive cable and the outer tube, and/or to reduce frictional forces between drive cable 130 (which rotates), and outer tube 140 (which remains stationary, during rotation of the drive cable).

For some applications, a generally similar technique is performed, but the fluid is pumped between the drive cable 130 (which rotates), and outer tube 140 (which remains stationary, during rotation of the drive cable), during operation of the ventricular assist device. For example, the fluid may be pumped into the space via the gap between first outer tube 140 and second outer tube 142, as shown. For some applications, the fluid is continuously pumped between the drive cable and the outer tube, during operation of the ventricular assist device, or is periodically pumped between the drive cable and the outer tube during operation of the ventricular assist device. It is noted that even for such applications, the fluid is pumped between the drive cable and the outer tube, but does not flow into the subject's bloodstream, since flow of the fluid in the distal direction is blocked, as described hereinabove. The pumping of the fluid is configured to remove air from the space between the drive cable and the outer tube, to reduce frictional forces between drive cable 130 (which rotates) and outer tube 140 (which remains stationary, during rotation of the drive cable), and/or to remove debris generated by the ventricular assist device from the interface between the drive cable and the outer tube.

Figure 14A:
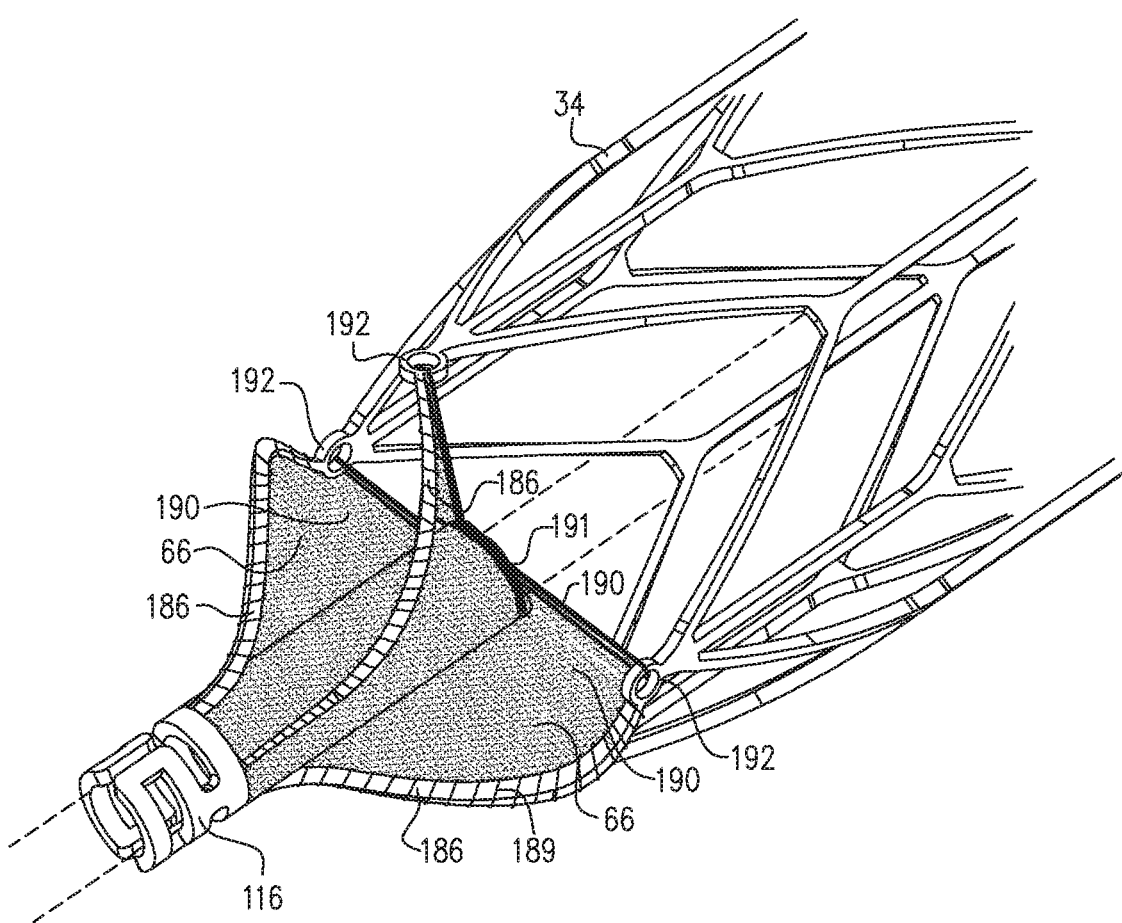
FIGS. 14A and 14B are schematic illustrations of a frame of a ventricular assist device, a stator being coupled to a proximal portion of the frame, in accordance with some applications of the present invention.
Figure 14B:
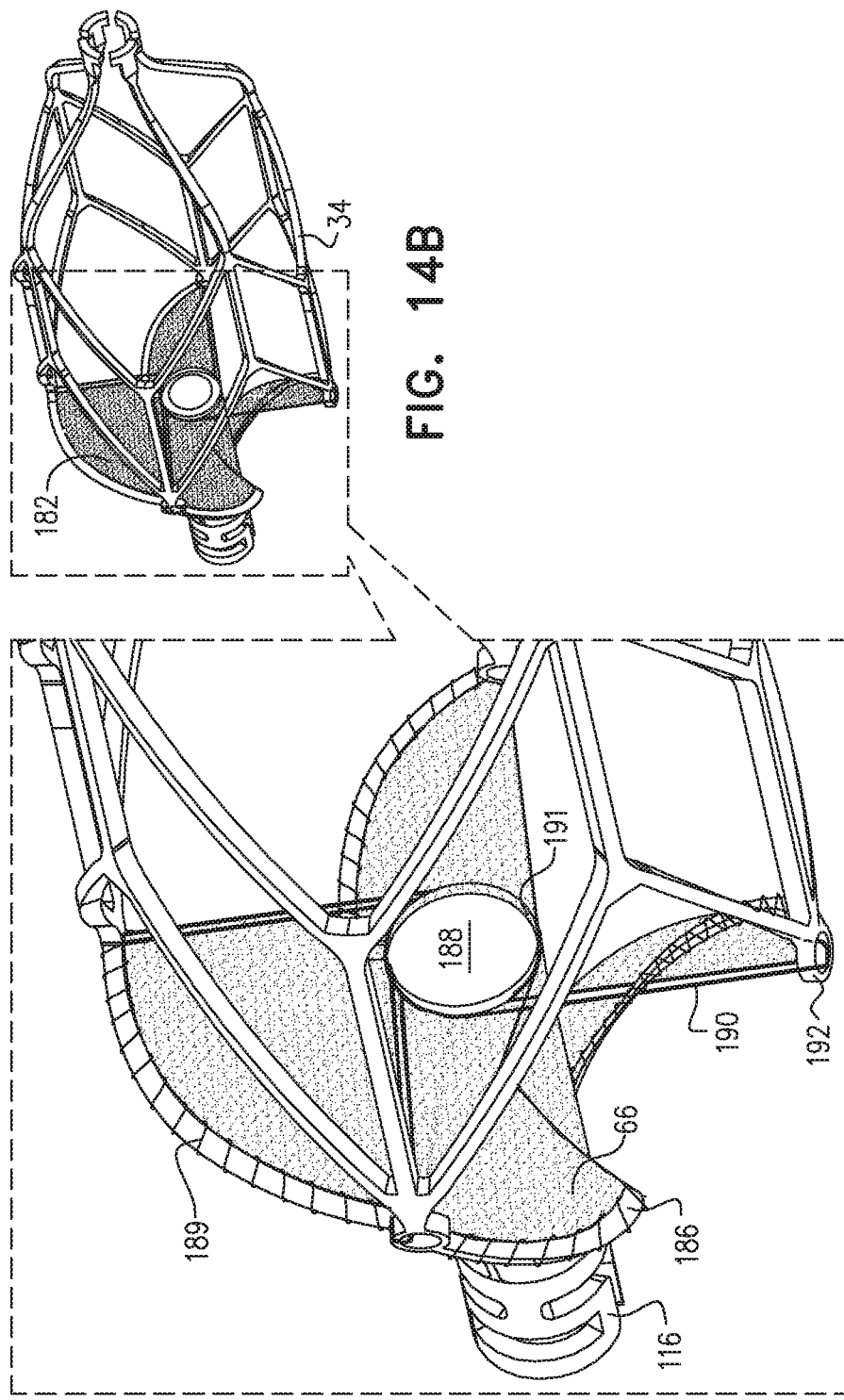

Reference is now made to FIGS. 14A and 14B, which are schematic illustrations of frame 34 of ventricular assist device 20, a stator 182 being coupled to a proximal portion of the frame, in accordance with some applications of the present invention. For some applications, the stator is integrally formed with frame 34, as described in further detail hereinbelow. Typically, the stator includes a plurality of curved projections 66 (e.g., more than 2, and/or less than 8 curved projections 66) that, when device 20 is in a non-radially-constrained configuration, extend from frame 34, and that are made of a flexible material, e.g., a polymer, such as polyurethane, and/or silicone. The curvature of the curved projection is typically such as to oppose the direction of rotation of the impeller, as described in further detail hereinbelow. For some applications, by virtue of using projections that are curved (e.g., curved such as to oppose the direction of rotation of the impeller of the ventricular assist device as described in further detail hereinbelow), stator 182 is configured to reduce rotational flow components from the blood flow prior to the blood flowing from the proximal end of the frame of the ventricular assist device.

As described hereinabove, typically, device 20 is inserted into the subject's ventricle transcatheterally, while frame 34 is in a radially-constrained state. Upon being released from the catheter, the frame automatically assumes its non-constrained shape, due to frame 34 self-expanding. Typically, during the insertion of the frame to the left ventricle, the curved projections of the stator are in folded states, and do not substantially increase the minimal diameter to which the frame can be radially-constrained, relative to if the tube did not contain the curved projections. Upon frame 34 expanding, the curved projections are configured to automatically assume their curved configurations, due to the curved projections being coupled to frame 34.

For some applications, curved projections 66 are made of a flexible material, e.g., a polymer, such as polyurethane, and/or silicone. The curved projections are typically coupled to struts 186 of frame 34 that are curved, the curvature of the curved struts thereby defining the curvature of the curved projections. Typically, the flexible material is coupled to frame 34, such that the flexible material defines a lumen 188 (FIG. 14B) therethrough that is aligned with the longitudinal axis of the frame. Axial shaft 92 of the ventricular assist device typically passes into the proximal end of the frame via lumen 188.

For some applications, in order to facilitate the coupling of the flexible material to the frame, in order to shape the flexible material in a desired shape, and/or in order to facilitate the formation of lumen 188, a plurality of elongate elements 190 (e.g., strings and/or wires, which are typically made of a similar material to elongate elements 67) are tied to the proximal end of the frame. For some applications, curved struts 186 define rings 192 or other coupling elements at distal ends thereof, to which elongate elements 190 are tied. The flexible material is typically coupled to the frame, such that curved films of material are supported by the curved struts and the elongate elements, each of the films defining a respective curved projection. For some applications, the strings and/or wires that are tied to the proximal end of the frame are tied to define a circle 191, which defines one of the ends of lumen 188. For example, during the formation of the stator, a mandrel may be placed through proximal bearing 116, and the elongate elements may be tied to rings 192 and made to encircle the mandrel, such as to define the pattern of elongate elements shown in FIG. 14B. The proximal end of the frame with the elongate elements and the mandrel is then dipped into the material (which is typically a polymer, such as silicone), while the material is in an uncured, liquid state. Subsequently, the material is cured such that it solidifies, e.g., by being left to dry. Once the material has dried, the mandrel is typically removed. For some applications, the other end of lumen 188 is defined by proximal bearing 116 disposed at the proximal end of frame 34. Typically, the flexible material extends from circle 191 defined by the strings and/or wires to proximal bearing 116, such as to define lumen 188. For some applications sutures 189 are tied around curved struts 186, in order to facilitate coupling between the material and the struts, e.g., as described hereinabove with reference to sutures 53 of impeller 50.

Figure 15A:
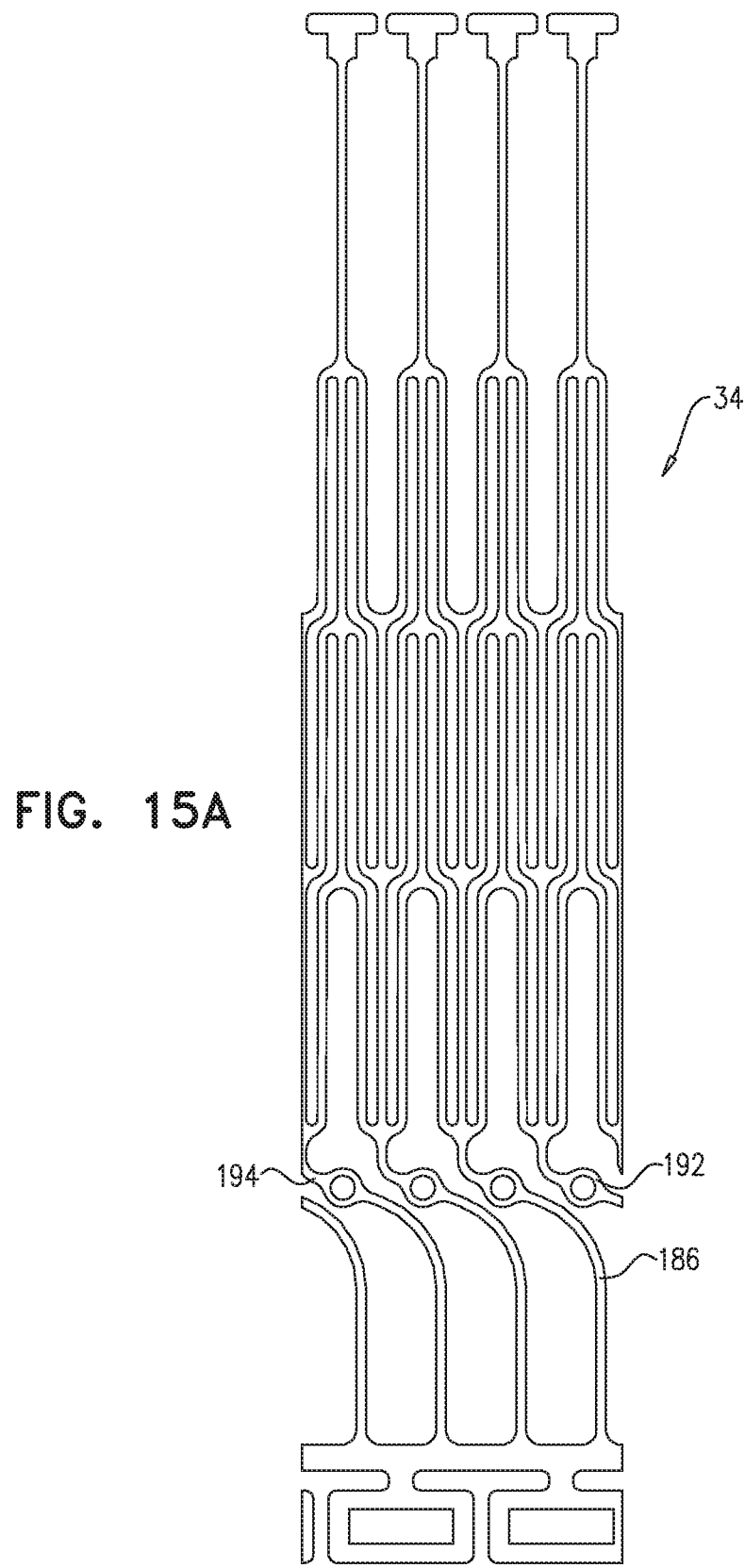
FIG. 15A is a schematic illustration of a flattened profile of a frame of a ventricular assist device, in accordance with some applications of the present invention.
Figure 15B:
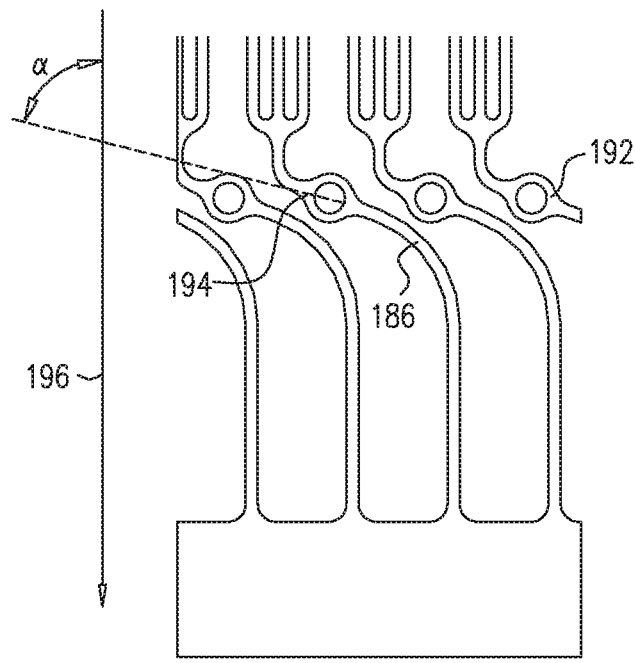
FIG. 15B is a schematic illustration showing an enlarged view of the proximal end of the frame of the ventricular assist device, in accordance with some applications of the present invention.
Figure 15C:
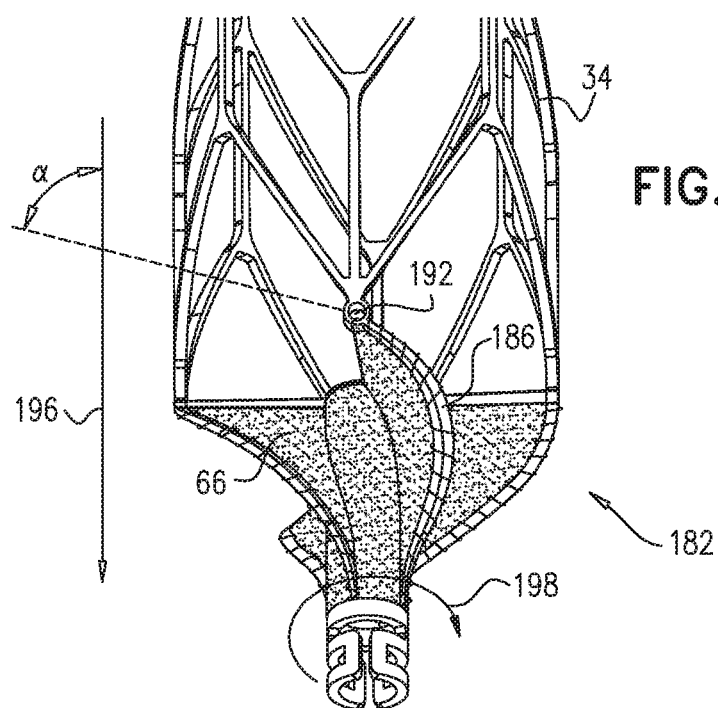
FIG. 15C is a schematic illustration of the frame of the ventricular assist device, a material that defines curved projections being coupled to the frame, in accordance with some applications of the present invention.

Reference is now made to FIG. 15A, which is a schematic illustration of a flattened profile of frame 34 of ventricular assist device 20, in accordance with some applications of the present invention. As shown, the frame includes curved struts 186, at its proximal end, with rings 192 disposed toward the tips of each of the struts. Reference is also made to FIG. 15B, which is a schematic illustration showing an enlarged view of the proximal end of frame 34, in accordance with some applications of the present invention. A tip 194 of curved strut 186 typically defines the orientation of the leading edge of the corresponding blade (i.e., curved projection) of the stator, once the flexible material is coupled to the curved strut. Reference is additionally made to FIG. 15C, which is a schematic illustration of frame 34, showing the frame with the material that defines curved projections 66 coupled to the frame, in accordance with some applications of the present invention. It may be observed that the orientations of the leading edges of the curved projections are defined by the orientations of the corresponding tips of the curved struts.

As shown in FIG. 15B, the tip 194 of curved strut 186 is shaped to define an angle alpha with respect to the axial component of blood flow through the frame, which is indicated by arrow 196, and which is parallel to the longitudinal axis of the frame, and toward the proximal end of the frame. The leading edge of the corresponding curved projections typically also defines an angle that is approximately equal to angle alpha, with respect to the general direction of blood flow, as indicated in FIG. 15C. (For some applications, upon struts 186 undergoing radial expansion, the angle of the leading edges of the curved projections becomes slightly less than alpha.) For some applications, angle alpha is greater than 45 degrees (e.g., greater than 60 degrees), and/or less than 85 degrees (e.g., less than 80 degrees), e.g., 45-85 degrees, or 60-80 degrees.

The direction of rotation of the impeller is indicated by arrow 198 in FIG. 15C. As may be observed in FIG. 15C, the curvature of the curved projections is typically such as to oppose the direction of rotation of the impeller (which is the direction of rotation of rotational flow components within the blood flow, as imparted to the blood flow by the impeller). From the distal ends of the curved projections to their proximal ends, the curved projections curve such as to become progressively closer to being parallel with the longitudinal axis of the frame. The curvature of the curved projections is such as to reduce rotational flow components from the blood flow prior to the blood flowing from the proximal end of the frame of the ventricular assist device.

Reference is now made to FIGS. 16A, 16B, 16C and 16D, which are schematic illustrations of ventricular assist device 20, the ventricular assist device including one or more blood-pressure-measurement tubes 210, in accordance with some applications of the present invention. As described hereinabove, typically, the ventricular assist device includes tube 24, which traverses the subject's aortic valve, such that a proximal end of the tube is disposed within the subject's aorta and a distal end of the tube is disposed within the subject's left ventricle. Typically, a blood pump, which typically includes impeller 50, is disposed within the subject's left ventricle within tube 24, and is configured to pump blood through tube 24 from the left ventricle into the subject's aorta. For some applications, blood-pressure-measurement tube 210 is configured to extend to at least an outer surface 212 of tube 24, such that an opening 214 at the distal end of the blood-pressure-measurement tube is in direct fluid communication with the patient's bloodstream outside tube 24. A pressure sensor 216 (illustrated schematically in FIG. 1A) measures pressure of blood within the blood-pressure-measurement tube. Typically, by measuring pressure of blood within the blood-pressure-measurement tube, the pressure sensor thereby measures the subject's blood pressure outside tube 24. Typically, blood-pressure-measurement tube 210 extends from outside the subject's body to opening 214 at the distal end of the tube, and pressure sensor 216 is disposed toward a proximal end of the tube, e.g., outside the subject's body. For some applications, computer processor 25 (FIG. 1A), receives an indication of the measured blood pressure and controls the pumping of blood by the impeller, in response to the measured blood pressure.

Figure 16B:
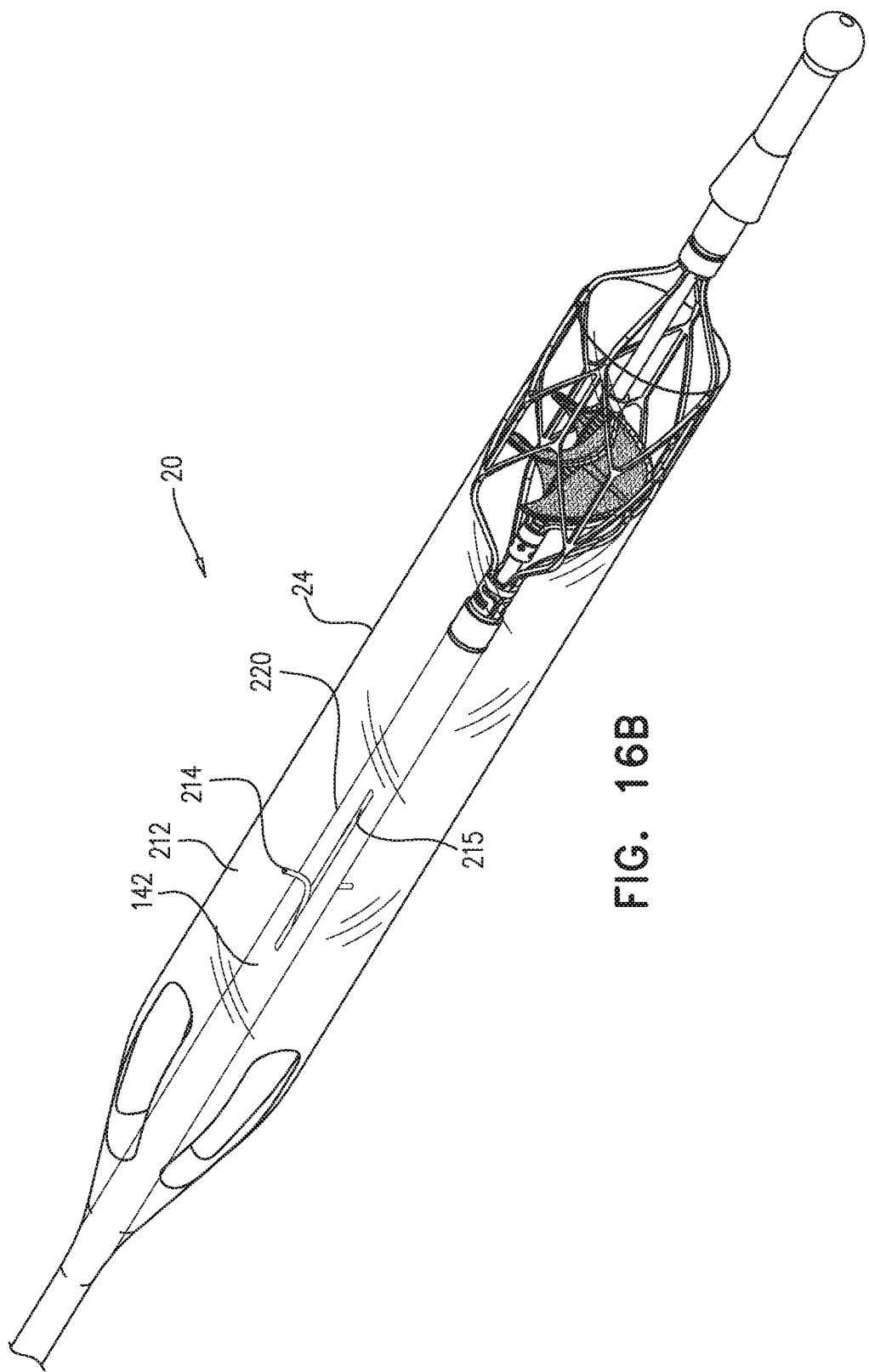

Referring to FIGS. 16A and 16B, for some applications, the one or more blood-pressure-measurement tubes include one or more left ventricular blood-pressure-measurement tubes 220 that are configured to extend to the outer surface of blood-pump tube 24 at a location along the tube that is configured to be within the subject's left ventricle proximal to the blood pump (e.g., proximal to impeller 50). For such applications, the pressure sensor is configured to measure the subject's left-ventricular pressure by measuring pressure of blood within the left-ventricular blood-pressure-measurement tube. For some applications, the ventricular assist device includes two or more such left ventricular blood-pressure-measurement tubes, e.g., as shown in FIGS. 16A and 16B. For some applications, based upon the blood pressures measured within each of the left ventricular blood-pressure-measurement tubes, computer processor 25 determines whether the opening of one of the two or more left-ventricular blood-pressure-measurement tubes is occluded. This may occur, for example, due to the opening coming into contact with the wall of the interventricular septum, and/or a different intraventricular portion. Typically, in response to determining that the opening of one of the two or more left-ventricular blood-pressure-measurement tubes is occluded, the computer processor determines the subject's left-ventricular pressure based upon the blood pressure measured within a different one of the two or more left-ventricular blood-pressure-measurement tubes.

For some applications, the one or more blood-pressure-measurement tubes include one or more aortic blood-pressure-measurement tubes 222 that are configured to extend to the outer surface of the tube at a location along the tube that is configured to be within the subject's aorta, as shown in FIG. 16C. For such applications, the pressure sensor is configured to determine the subject's aortic pressure by measuring pressure of blood within the aortic blood-pressure-measurement tube. For some applications, the ventricular assist device includes two or more such aortic blood-pressure-measurement tubes, e.g., as shown in FIG. 16C. For some applications, based upon the blood pressures measured within each of the aortic blood-pressure-measurement tubes, computer processor 25 determines whether the opening of one of the two or more aortic blood-pressure-measurement tubes is occluded. This may occur, for example, due to the opening coming into contact with the wall of the aorta. Typically, in response to determining that the opening of one of the two or more aortic blood-pressure-measurement tubes is occluded, the computer processor determines the subject's aortic pressure based upon the blood pressure measured within a different one of the two or more aortic blood-pressure-measurement tubes.

For some applications, the ventricular assist device includes both left ventricular blood-pressure-measurement tubes and aortic blood-pressure-measurement tubes all of which extend to the outer surface of tube 24, e.g., as shown in FIG. 16C.

Still referring to FIG. 16C, as described hereinabove, for some applications, drive cable 130 extends from a motor outside the subject's body to axial shaft 92 upon which impeller 50 is disposed. Typically, the drive cable is disposed within outer tube 142. For some applications, the drive cable is disposed within first outer tube 140 and second outer tube 142, as described hereinabove. For some applications, the one or more blood-pressure measurement tubes are disposed within outer tube 142, surrounding the drive cable. For some applications, portions of the one or more blood-pressure-measurement tubes are defined by the walls of outer tube 142, as shown. For some applications, within outer tube 142, the blood pressure measurement tubes have elliptical cross-sections (as shown). Typically, this increases the cross-sectional areas of the tubes, relative to if they were to have circular cross-sections. Typically, within a distal portion of each of the blood-pressure measurement tubes (which extends to opening 214), the tube has a circular cross-section. For some applications, the diameter of the distal portion of the tube is more than 0.2 mm, and/or less than 0.5 mm (e.g., 0.2-0.5 mm).

As shown in FIG. 16A, for some applications, aortic blood pressure is measured using at least one aortic blood-pressure-measurement tube 222 that defines an opening 219 in outer tube 142 at its distal end. The aortic blood-pressure-measurement tube is configured to extend from outside the subject's body to an outer surface of outer tube 142 within the subject's aorta, such that the opening at the distal end of the aortic blood-pressure-measurement tube is in direct fluid communication with the subject's aortic bloodstream. It is noted that, for such applications, the aortic blood-pressure-measurement tube does not extend to the outer surface of tube 24. Blood pressure sensor 216 is configured to measure the subject's aortic blood pressure by measuring blood pressure within the aortic blood-pressure-measurement tube. For some applications, opening 219 in outer tube 142 is disposed within tube 24, as shown in FIG. 16D. Aortic pressure is measured via opening 219, since pressure inside tube 24 at locations downstream of the impeller is typically equal to aortic pressure.

As shown in FIGS. 16A and 16B, for some applications, outer tube 142 defines a groove 215 in a portion of the outer surface of the outer tube that is configured to be disposed within tube 24. Typically, during insertion of the ventricular assist device into the subject's body, the portion of blood-pressure-measurement tube 210 that extends from within tube 24 to at least an outer surface of tube 24, is configured to be disposed within the groove, such that the portion of the blood-pressure-measurement tube does not protrude from the outer surface of the outer tube.

Referring now to FIG. 16D, for some applications, distal portions of blood-pressure-measurement tubes 210 are disposed on the outside of tube 24. For example, as shown, blood-pressure-measurement tubes 210 may extend from outer tube 142 to the proximal end of tube 24, and thereafter the blood pressure measurement tubes may be built into the outer surface of tube 24. For some applications, one or more tubes run along the outer surface of tube 24 in the manner shown in FIG. 16D, but the tubes continue until the distal end of tube 24 until tip portion 120 of the ventricular assist device. The tubes are used to inflate an inflatable portion of the tip portion as described in further detail hereinbelow with reference to FIG. 21C.

Although the ventricular assist device as described with reference to FIGS. 16A-D has been described as including a blood pump that is configured to be disposed within the subject's left ventricle, for some applications, blood-pressure-measurement tube 210 and the techniques described herein for use with blood-pressure-measurement tube 210 are used with a ventricular assist device that includes a blood pump elsewhere, e.g., within the subject's aorta. For some applications generally similar techniques are used with a right ventricular assist device. For example, device 20 may be inserted into the right ventricle and used to pump blood from the right ventricle to the pulmonary artery. For some such applications, the blood-pressure measurement tubes are used to measure pressure in the right ventricle and/or the pulmonary artery. For some applications, a generally similar device to device 20 is used as a cardiac assist device by being used to pump blood in an antegrade direction from the right atrium to the right ventricle, from the vena cava to the right atrium, from the right atrium to the pulmonary artery, and/or from the vena cava to the pulmonary artery. For some such applications, the blood-pressure measurement tubes are used to measure pressure in the right ventricle, the vena cava, the right atrium, and/or the pulmonary artery.

In general, the scope of the present invention includes applying any of the apparatus and methods that are described herein to a right ventricular assist device, mutatis mutandis. The right-ventricular assist device typically has a generally similar configuration to that described herein and is used to pump blood from the right ventricle to the pulmonary artery, with tube 24 passing through the pulmonary semilunar valve. For some applications, components of device 20 are applicable to different types of blood pumps. For example, aspects of the present invention may be applicable to a pump that is used to pump blood from the vena cava and/or the right atrium into the right ventricle, from the vena cava and/or the right atrium into the pulmonary artery, and/or from the renal veins into the vena cava. Such aspects may include features of pump portion 27, impeller 50, features of drive cable 130, apparatus and methods for measuring blood pressure, apparatus and methods for measuring flow, etc.

For some applications, generally similar techniques to those described with reference to blood-pressure-measurement tube 210 are performed using an electrical wire that extends from within blood-pump tube 24 (and that typically extends from outside the subject's body) to the outer surface of tube 24, such that at least a tip of the wire is in electrical communication with the subject's bloodstream outside of tube 24. The subject's blood pressure outside tube 24 (e.g., the subject's ventricular blood pressure and/or the subject's aortic blood pressure) is measured by detecting an electrical parameter using the portion of the wire that is in electrical communication with the subject's bloodstream outside tube 24.

Figure 17A:
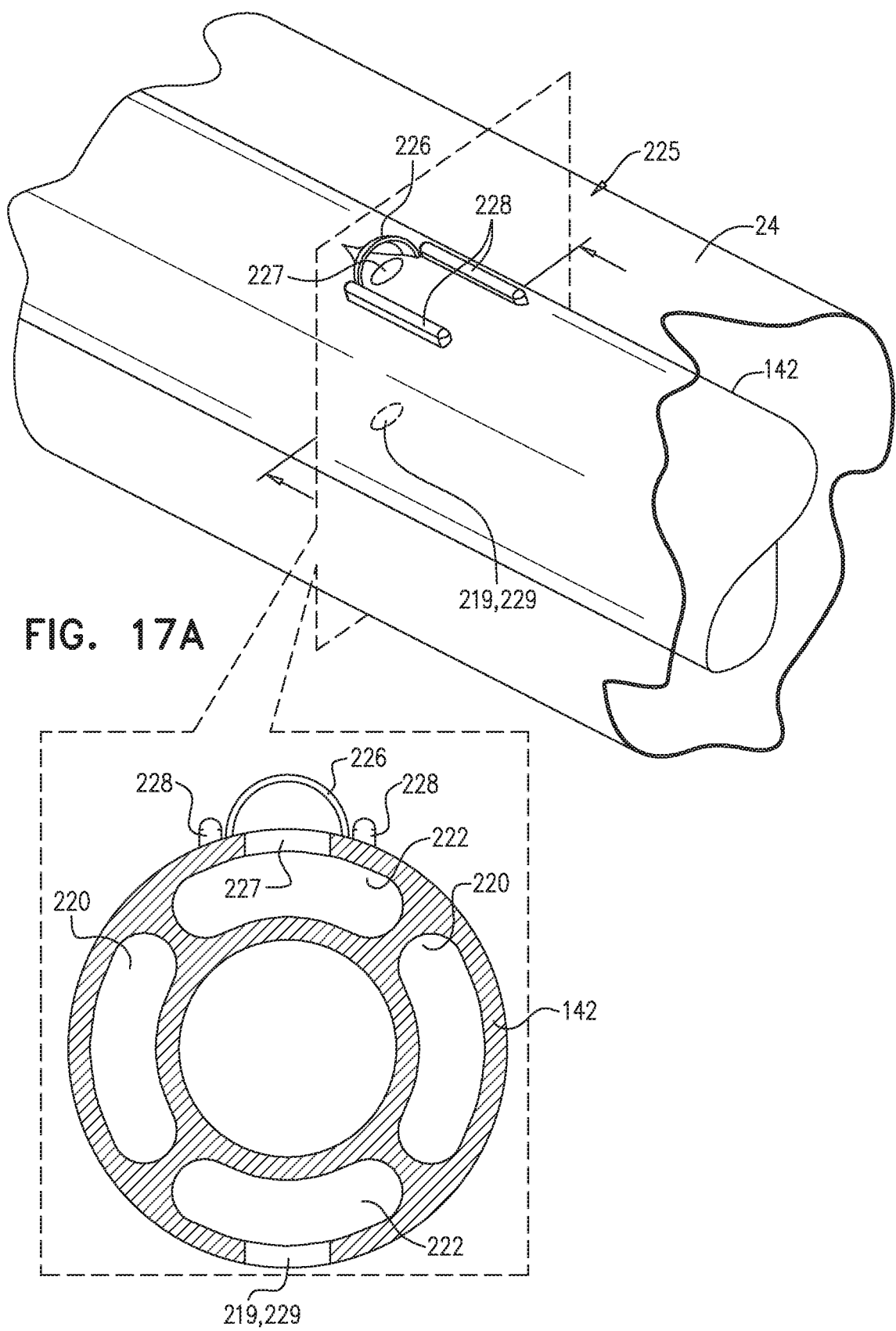
FIGS. 17A, 17B, and 17C are schematic illustrations of a ventricular assist device that includes a pitot tube that is configured to measure blood flow through a tube of the device, in accordance with some applications of the present invention.
Figure 17B:
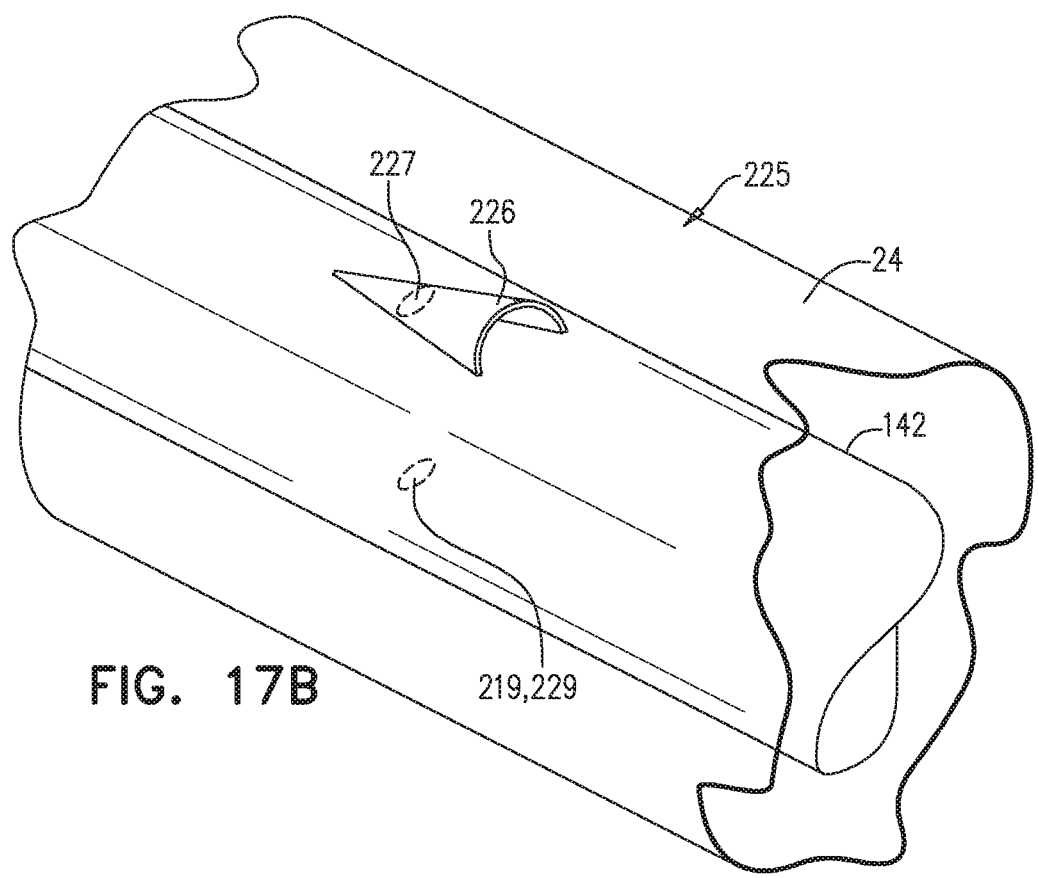
Figure 17C:
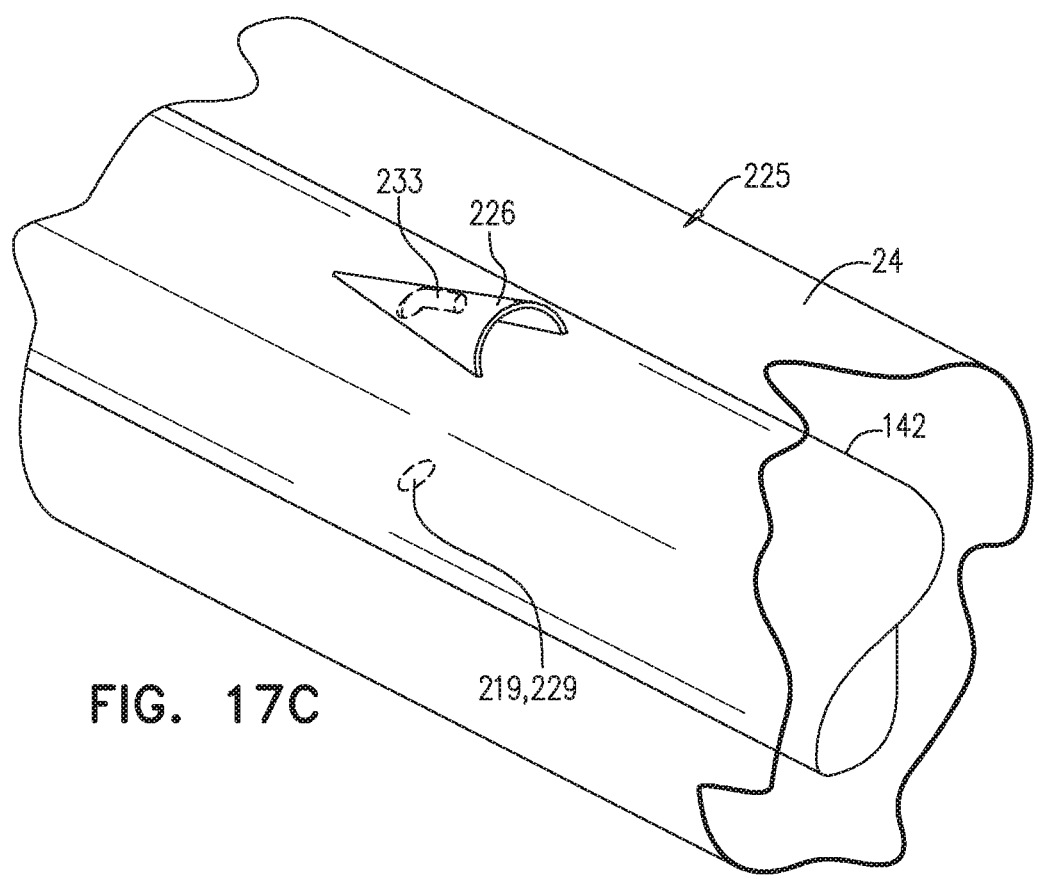

Reference is now made to FIGS. 17A, 17B, and 17C, which are schematic illustrations of outer tube 142 of ventricular assist device 20, the outer tube including a pitot tube 225 that is configured to measure blood flow through tube 24 of the device, in accordance with some applications of the present invention. The portion of outer tube 142 shown in FIGS. 17A-C is typically disposed within tube 24. For some applications, a flow obstacle 226 (which is typically funnel shaped) is configured to create a stagnation region near a stagnation pressure tap 227. For some applications, flow straighteners 228 are added to the outer surface of tube 142, in order remove any swirling component of the flow (which does not contribute to the axial flow rate), as shown in FIG. 17A. Alternatively, the stagnation pressure tap is disposed sufficiently proximally within funnel-shaped flow obstacle 226 that the flow obstacle itself acts to remove the swirling components of the flow, prior to the blood reaching the stagnation pressure tap, as shown in FIG. 17B. For some applications, the stagnation pressure tap includes a short tube 233 that protrudes from outer tube 142 within funnel-shaped flow obstacle 226, such that the opening of short tube 233 faces the direction of axial blood flow through tube 24. Outer tube 142 additionally defines opening 219, which is generally as described hereinabove, and which functions as a static pressure tap 229. The pressure within stagnation pressure tap 227 and within static pressure tap 229 is measured using pressure sensors, e.g., pressure sensors that are disposed outside the subject's body, as described hereinabove with reference to FIGS. 16A-D.

In some applications, flow through tube 24 is calculated based upon the pressure measurements. For example, flow through tube 24 may be calculated using the following equation:

$$Q = C \cdot A \cdot \sqrt{\frac{2\Delta P}{\rho}}$$

in which:

Q is the flow through tube 24,

C is a calibration constant that is empirically determined and accounts for factors such as impeller velocity and the geometries of pressure taps 227 and 229, A is the cross-sectional area of tube 24 (not including the area that outer tube 142 occupies), $\Delta P$ is the difference between the stagnation pressure (measured via pressure tap 227), and the static pressure (measured via pressure tap 229)

$\rho$ is the fluid density of blood.

Figure 18:
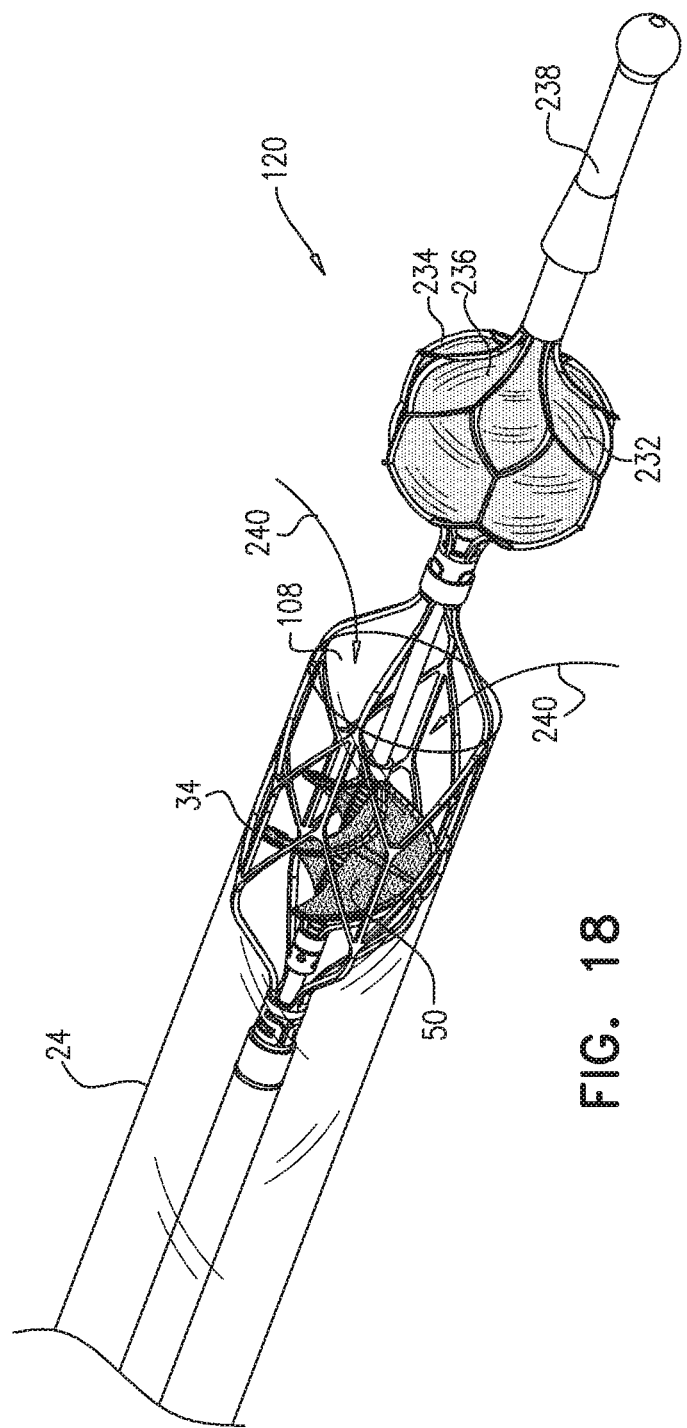
FIG. 18 is a schematic illustration of a ventricular assist device, a tip portion of the device, being a radially-expandable atraumatic distal tip portion, in accordance with some applications of the present invention.

Reference is now made to FIG. 18, which is a schematic illustration of ventricular assist device 20, distal tip portion 120 of the device, being a radially-expandable atraumatic distal tip portion, in accordance with some applications of the present invention. As described hereinabove, the ventricular assist device typically includes tube 24, which traverses the subject's aortic valve, such that a proximal portion of the tube is disposed within the subject's aorta, and a distal portion of the tube is disposed within the subject's left ventricle. Tube 24 defines one or more blood inlet openings 108 within the distal portion of the tube, and one or more blood outlet openings 109 within the proximal portion of the tube. A blood pump of the ventricular assist device, which is configured to be disposed within tube 24, pumps blood from the left ventricle into tube 24 through the one or more blood inlet openings, and out of tube 24 into the aorta through the one or more blood outlet openings. Typically, radially-expandable atraumatic distal tip portion 120 is disposed within the subject's left ventricle distally with respect to the one or more blood inlet openings. The distal tip portion is configured to be inserted into the left ventricle in a radially-constrained configuration. Typically, at least a portion of the distal tip portion is disposed inside delivery catheter 143 (shown in FIG. 1B, for example) during insertion of the distal tip portion into the left ventricle, and the delivery catheter maintains the distal tip portion in the radially-constrained configuration. The distal tip portion is configured to assume a non-radially-constrained configuration within the subject's left ventricle, in which at least a portion 232 of the distal tip portion is radially expanded relative to the radially-constrained configuration of the distal tip.

For some applications, radially-expandable atraumatic distal tip portion 120 includes a frame 234 made of a shape-memory material (such as nitinol), which is shape set, such that the frame radially expands upon being released from the delivery catheter. Typically, the frame is covered with a biocompatible blood-impermeable material 236, such as polyurethane, polyester, and/or silicone, which is typically configured to form a continuous surface that covers the frame. For some applications, the distal tip portion additionally includes an atraumatic distal tip 238, which may have a similar shape to distal tip portion 120, as described hereinabove with reference to FIG. 6C and/or hereinbelow with reference to FIG. 21B.

Radially-expandable atraumatic distal tip portion 120 is typically configured such that, in the non-radially-constrained configuration of the distal tip portion, radially-expandable portion 232 of the distal tip portion separates one or more blood inlet openings 108 from inner structures of the left ventricle in three dimensions. In this manner, radially-expandable portion 232 of the distal tip portion separates one or more blood inlet openings 108 from the interventricular septum, chordae tendineae, papillary muscles, and/or the apex of the left ventricle. For some applications, the radially-expandable portion 232 of the distal tip portion is shaped such as to direct blood flow from the left ventricle into the one or more blood inlet openings, as indicated by arrows 240 in FIG. 18.

Reference is now made to FIGS. 19A-19B, which are schematic illustrations of ventricular assist device 20, the ventricular assist device distal tip portion 120 of the device, being a radially-expandable atraumatic distal tip portion, in accordance with some applications of the present invention. Reference is also made to FIGS. 20A-20B, which are schematic illustrations of ventricular assist device 20, the ventricular assist device distal tip portion 120 of the device, being a radially-expandable atraumatic distal tip portion, in accordance with some alternative applications of the present invention. FIGS. 19A and 20A show the distal tip portion in its radially-constrained configuration, while disposed at least partially inside delivery catheter 143, and FIGS. 19B and 20B show the distal tip portion in its non-radially-constrained configuration. In general, distal tip portion 120 as shown in FIGS. 19A-B and 20A-B has generally similar functionality to that described hereinabove with reference to distal tip portion 120 as shown in FIG. 18.

As described hereinabove, typically, at least a portion of distal tip portion 120 is disposed inside delivery catheter 143 during insertion of the distal tip into the left ventricle, and the delivery catheter maintains the distal tip portion in the radially-constrained configuration, as shown in FIGS. 19A and 20A. For some applications, the distal tip portion is configured such that, when the delivery catheter maintains the distal tip portion in the radially-constrained configuration, a distal region 244 of the distal tip portion protrudes from a distal end of the delivery catheter. Typically, at least in the radially-constrained configuration of the distal tip portion, the distal region is at least semi-rigid, and is shaped to converge radially in the longitudinal direction toward a distal end 246 of the distal tip portion. Typically, the delivery catheter is inserted into the subject's vasculature via a puncture. For some applications, the radially-converging semi-rigid distal region of the distal tip portion is configured to act as a dilator, by dilating the puncture during insertion of the delivery catheter via the puncture. In this manner, the delivery catheter and components of the ventricular assist device that are disposed within the delivery catheter can be inserted into the puncture without requiring pre-dilation of the puncture, and without requiring a separate introducer device, for facilitating insertion of the delivery catheter through the puncture. For some applications, the distal region is configured to allow percutaneous insertion of the catheter into a punctured vessel, by placing a first guidewire through the distal region of the distal tip portion. Subsequently, the distal region is used to guide the catheter along an arched anatomy (e.g., the aortic arch) by tracking the course and shape of a second guidewire that is less stiff than the first guidewire. For some such applications, delivery catheter 143 itself acts as an introducer. Typically, the delivery catheter has an inner diameter of less than 9 mm. For example, the delivery catheter may be an 8 French catheter. For some applications, the delivery catheter is inserted through the puncture via a short introducer device.

For some applications, distal tip portion 120 is configured such that in the non-radially-constrained configuration of the distal tip portion, distal end 246 of the distal tip portion is enveloped within radially-expandable portion 232 of the distal tip portion. For some applications, the distal end is retracted proximally, such that the distal end is enveloped within the radially-expandable portion. For example, the distal tip portion may include a spring 249 and/or an elastomeric material that is configured to retract the distal end of the distal tip portion, as shown in the transition from FIG. 19A to FIG. 19B. For some applications, the distal end inverts, such that the distal end becomes enveloped within the radially-expandable portion of the distal tip portion. For example, the transition from FIG. 20A to 20B shows distal end 246 of distal tip portion 120 inverting, as indicated by arrows 264. For some applications, by the distal end becoming enveloped within the radially-expandable portion, the distal tip is prevented from becoming entangled within the chordae tendineae, and/or is prevented from causing trauma to an internal structure of the left ventricle.

Referring to FIG. 19B, for some applications, the distal tip portion includes a plurality of longitudinal struts 248, which are shape set to curve radially outwardly. Typically, the struts are made of a shape-memory material, such as nitinol. For some applications, the struts are covered with a biocompatible blood-impermeable material 250, such as polyurethane, polyester, and/or silicone, which is typically configured to form a continuous surface that covers the struts. Referring to FIG. 20B, for some applications, the distal tip portion includes a braided shape-memory material 260. For some applications, the braided shape-memory material is at least partially covered with a biocompatible blood-impermeable material 262, such as polyurethane, polyester, and/or silicone, which is typically configured to form a continuous surface that covers the braided shape-memory material. Alternatively, the braided shape-memory material is not covered.

Figure 21A:
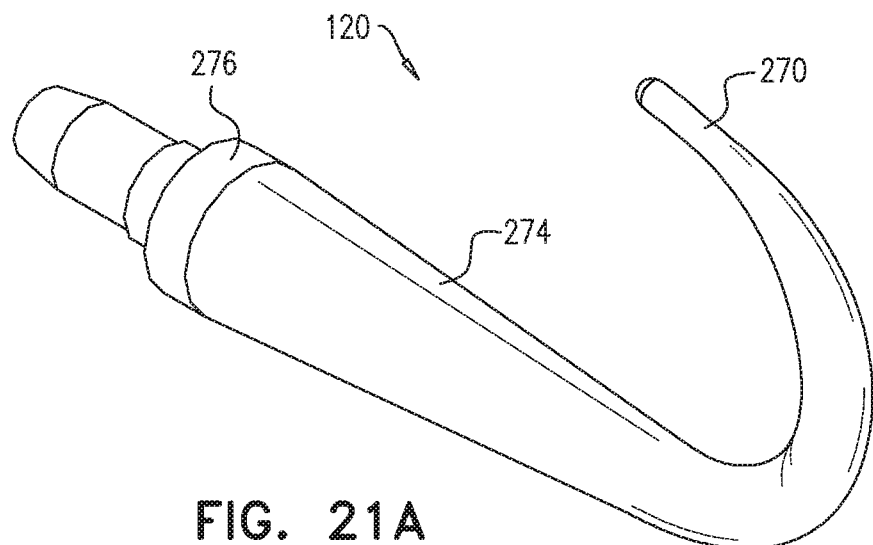
FIGS. 21A, 21B, 21C, and 21D are schematic illustrations of a distal tip portion of a ventricular assist device, in accordance with some applications of the present invention.
Figure 21B:
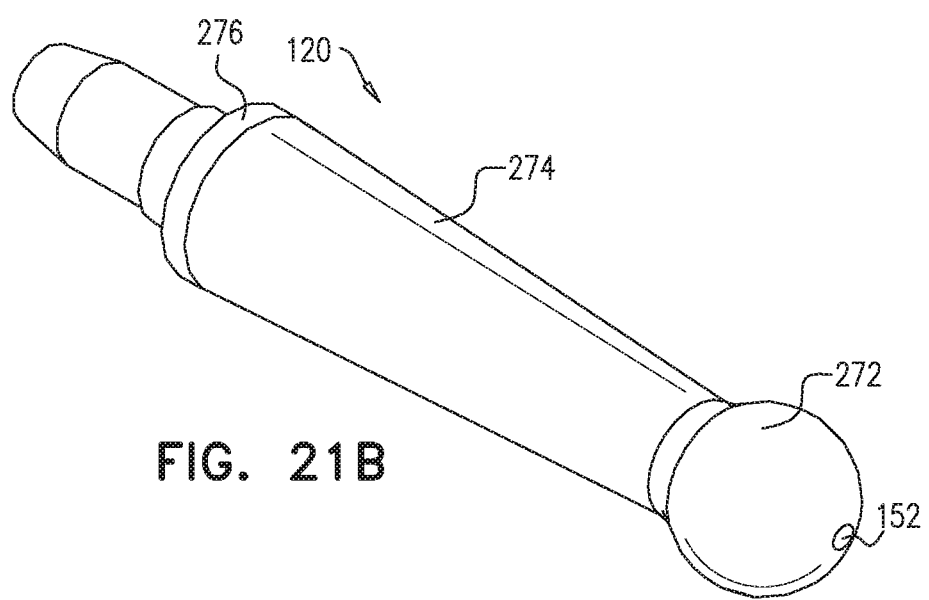

Reference is now made to FIGS. 21A, 21B, 21C, and 21D, which are schematic illustrations of distal tip portion 120 of ventricular assist device 20, the distal tip portion being configured to be atraumatic, in accordance with some applications of the present invention. As shown in FIG. 21A, for some applications, the distal tip portion includes a J-tip 270 at its distal end. As shown in FIG. 21B, for some applications, the distal tip portion includes a bulbous tip 272 at its distal end. As shown in FIGS. 21A and 21B, for some applications, proximal to the J-tip or the bulbous tip, the distal tip portion is externally shaped to define a frustum 274. Typically, a proximal end 276 of the frustum acts as a stopper for preventing advancement of delivery catheter 143 past the proximal end, in a generally similar manner to that described with respect to flared portion 124, with reference to FIG. 6C.

For some applications, the tip portion has a straightened configuration in which the tip portion is shaped to define a frustum that extends from the proximal end of the frustum until the distal tip of the distal tip portion. For example, a guidewire (such as guidewire 10) that is inserted through lumen 122 (shown in FIGS. 6A-C) defined by the tip portion may maintain the tip portion in its straightened configuration. For some such applications, the tip portion has a non-constrained configuration (which the tip portion is configured to assume inside the ventricle (e.g., due to the guidewire being removed from inside the tip portion)), in which a distal portion of the frustum is shaped as a J-tip, as shown in FIG. 21A.

Figure 21C:
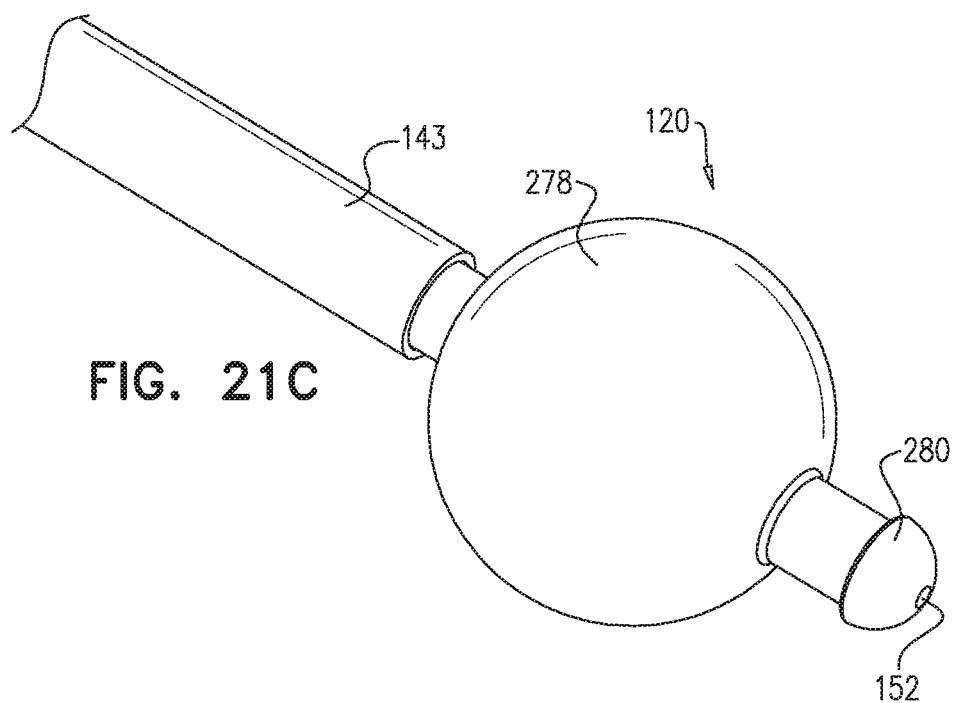

As shown in FIG. 21C, for some applications, the outer surface of the distal tip portion includes an inflatable portion 278 (e.g., a balloon), which is configured to be inflated when the distal tip portion is disposed inside the subject's left ventricle. For some such applications, an inflation lumen for inflating the inflatable portion is configured to pass through outer tube 142, and to then pass along the outer surface of tube 24, and to the inflatable portion of the distal tip portion. For example, the inflation lumen may be configured in a generally similar manner to blood-pressure measurement tube 210 as shown in FIG. 16D, but may continue to run along the outer surface of tube 24 until the distal end of the tube, and then continue to the inflatable portion of the distal tip portion. For some applications, the distal end of the distal tip portion includes a rounded portion 280. As described hereinabove, typically, the distal tip portion includes a hemostasis valve 152 at its distal end.

Figure 21D:
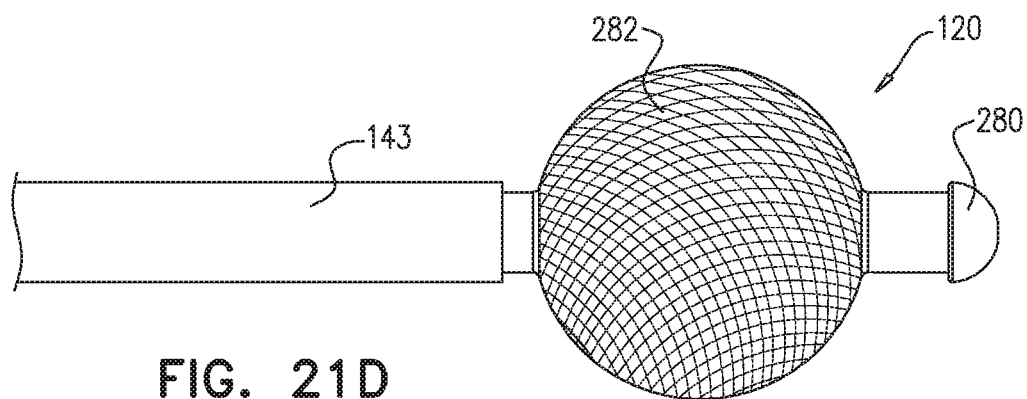

As shown in FIG. 21D, for some applications, the outer surface of the distal tip portion includes a radially expandable portion 282 (e.g., a radially expandable mesh, as shown, and/or a radially-expandable frame), which is configured to self-expand when the distal tip portion is disposed inside the subject's left ventricle.

Atraumatic distal tip portion 120, as shown in FIGS. 21C and 21D, is typically configured such that, in the inflated or radially-expanded configuration of the distal tip portion, the inflated portion or the radially expanded portion of the distal tip portion separates one or more blood inlet openings 108 from inner structures of the left ventricle in three dimensions. In this manner, the inflated portion or the radially expanded portion of the distal tip portion separates one or more blood inlet openings 108 from the interventricular septum, chordae tendineae, papillary muscles, and/or the apex of the left ventricle. For some applications, the inflated portion or the radially expanded portion of the distal tip portion is shaped such as to direct blood flow from the left ventricle into the one or more blood inlet openings, as described hereinabove with reference to distal tip portion 120 as shown in FIG. 18.

Figure 22A:
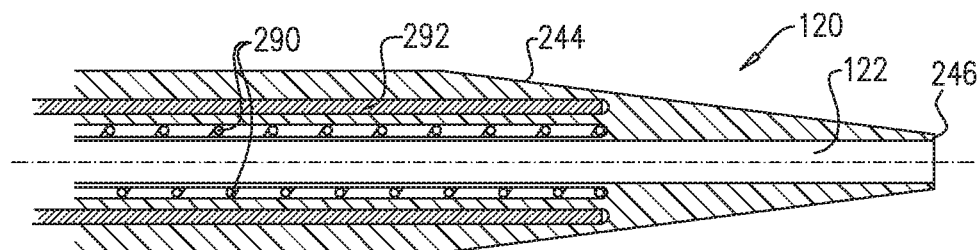
FIGS. 22A and 22B are schematic illustrations of a distal tip portion of a ventricular assist device, respectively, in an axially-stiffened configuration and a non-axially-stiffened configuration, in accordance with some applications of the present invention.
Figure 22B:
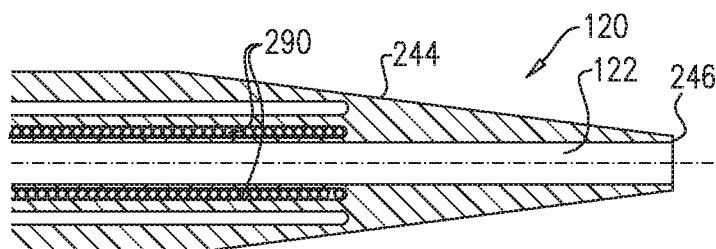

Reference is now made to FIGS. 22A and 22B, which are schematic illustrations of distal tip portion 120 of ventricular assist device 20, respectively, in an axially-stiffened configuration and a non-axially-stiffened configuration, in accordance with some applications of the present invention. As described hereinabove, for some applications, the distal tip portion is configured such that, when the delivery catheter maintains the distal tip portion in the radially-constrained configuration, a distal region 244 of the distal tip portion protrudes from a distal end of the delivery catheter. Typically, at least in the axially-stiffened configuration of the distal tip portion, the distal region is at least semi-rigid, and is shaped to converge radially in the longitudinal direction toward a distal end 246 of the distal tip portion. Typically, the delivery catheter is inserted into the subject's vasculature via a puncture. Further typically, the distal tip portion defines lumen 122, through which guidewire 10 is inserted, as described hereinabove. For some applications, the radially-converging semi-rigid distal region of the distal tip portion is configured to act as a dilator, by dilating the puncture during insertion of the delivery catheter via the puncture. In this manner, the delivery catheter and components of the ventricular assist device that are disposed within the delivery catheter can be inserted into the puncture without requiring pre-dilation of the puncture, and without requiring a separate introducer device, for facilitating insertion of the delivery catheter through the puncture. For some applications, the distal region is configured to allow percutaneous insertion of the catheter into a punctured vessel, by placing a first guidewire through the distal region of the distal tip portion. Subsequently, the distal region is used to guide the catheter along an arched anatomy (e.g., the aortic arch) by tracking the course and shape of a second guidewire that is less stiff than the first guidewire. For some such applications, delivery catheter 143 itself acts as an introducer. Typically, the delivery catheter has an inner diameter of less than 9 mm. For example, the delivery catheter may be an 8 French catheter. For some applications, the delivery catheter is inserted through the puncture via a short introducer device.

For some applications, the distal tip portion is made of a flexible material (such as silicone) with a spring 290 disposed around lumen 122. During insertion of the ventricular assist device into the subject's body, a rigid or semi-rigid stiffening element 292 (e.g., a rigid or semi-rigid tube) is placed inside distal region 244 of the distal tip portion, such as to stiffen the distal region. This configuration is shown in FIG. 22A. Subsequently, the stiffening element is retracted, such that the distal region of the distal tip portion becomes atraumatic (e.g., springy and flexible), as shown in FIG. 22B.

Figure 23A:
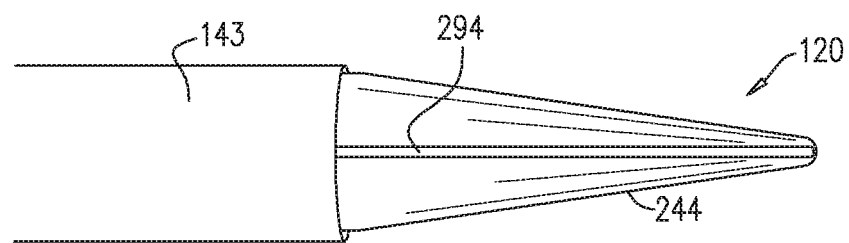
FIGS. 23A and 23B are schematic illustrations of a distal tip portion of a ventricular assist device, respectively, in a radially-constrained configuration and a non-radially-constrained configuration, in accordance with some applications of the present invention.
Figure 23B:
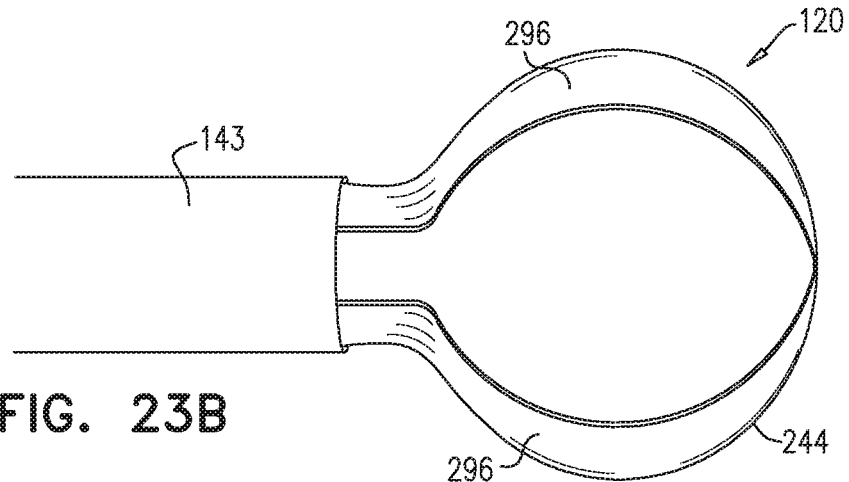

Reference is now made to FIGS. 23A and 23B, which are schematic illustrations of distal tip portion 120 of ventricular assist device 20, respectively, in a radially-constrained configuration and a non-radially-constrained configuration, in accordance with some applications of the present invention. For some applications, distal region 144 of the distal tip portion is shaped as a cone with slits 294 (e.g., two slits) in the cone. During insertion of the ventricular assist device into the subject's body, the distal region is maintained in its conical shape by delivery catheter 143. This configuration is shown in FIG. 23A. Subsequently, when the delivery catheter is retracted, the distal region is configured to form a two-dimensional circular or elliptical shape, by splitting into two semi-circles 296 or semi-ellipses around the slits, as shown in FIG. 23B. In the configuration shown in FIG. 23B, the distal tip portion is typically configured to be atraumatic and to separate the one or more blood inlet openings 108 from inner structures of the left ventricle in two dimensions. In this manner, the distal tip portion separates one or more blood inlet openings 108 from the interventricular septum, chordae tendineae, papillary muscles, and/or the apex of the left ventricle.

Figure 24A:
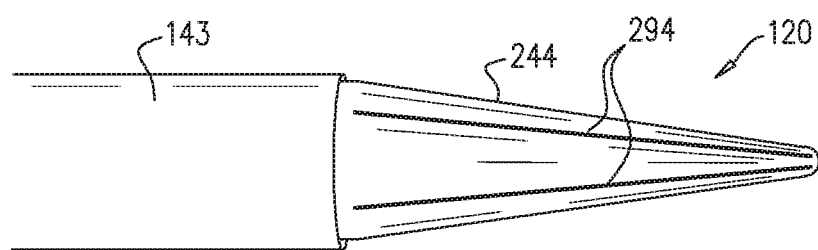
FIGS. 24A and 24B are schematic illustrations of a distal tip portion of a ventricular assist device, respectively, in a radially-constrained configuration and a non-radially-constrained configuration, in accordance with some applications of the present invention.
Figure 24B:
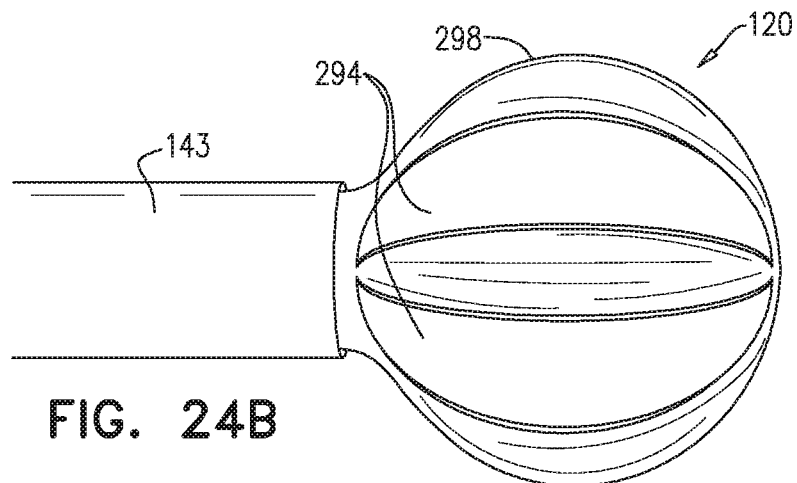

Reference is now made to FIGS. 24A and 24B, which are schematic illustrations of distal tip portion 120 of ventricular assist device 20, respectively, in a radially-constrained configuration and a non-radially-constrained configuration, in accordance with some applications of the present invention. For some applications, distal region 244 of the distal tip portion is shaped as a cone with slits 294 (e.g., four slits) in the cone. During insertion of the ventricular assist device into the subject's body, the distal region is maintained in its conical shape by delivery catheter 143. This configuration is shown in FIG. 24A.

Subsequently, when the delivery catheter is retracted, the distal region is configured to form a three-dimensional basket shape, by splitting into four arms 298 around the slits, as shown in FIG. 24B. (It is noted that the fourth arm is hidden from view in FIG. 24B.) In the configuration shown in FIG. 24B, the distal tip portion is typically configured to be atraumatic and to separate the one or more blood inlet openings 108 from inner structures of the left ventricle in three dimensions. In this manner, the distal tip portion separates one or more blood inlet openings 108 from the interventricular septum, chordae tendineae, papillary muscles, and/or the apex of the left ventricle.

For some applications, distal tip portion 120 has a pointed distal region 244, the diameter of the distal tip portion at the proximal end of the distal region being approximately equal to that of delivery catheter 143. Typically, pointed distal region 244 has a length of less than half (e.g., less than a quarter) of the total length of the distal tip portion. Further typically, the flexibility of the pointed distal region is greater than that of a proximal region of the distal tip portion. Typically, the distal region is configured to be straightened to a generally conical shape when a sufficiently stiff guidewire is inserted into it. For some applications, the distal region is configured to curl to a J-shape, in the absence of any external forces acting on the distal region (e.g., as shown in FIG. 21A).

Typically, the distal region of the distal tip portion acts as a dilator for delivery catheter 143, to allow percutaneous insertion of the catheter into a punctured vessel, by placing a first guidewire through the distal region of the distal tip portion. Subsequently, the distal tip portion is used to guide the catheter along an arched anatomy (e.g., the aortic arch) by tracking the course and shape of a second guidewire that is less stiff than the first guidewire. For some applications, the distal region of the distal tip portion is configured to curl, when the second guidewire is withdrawn, as described hereinabove.

For some applications, features of distal tip portion 120 described with reference to FIGS. 18-24B, as well as techniques for practicing therewith, are combined with features described with reference to tip portion 120, described hereinabove with reference to FIGS. 6A-C, and/or 13, as well as techniques for practicing therewith.

Figure 25A:
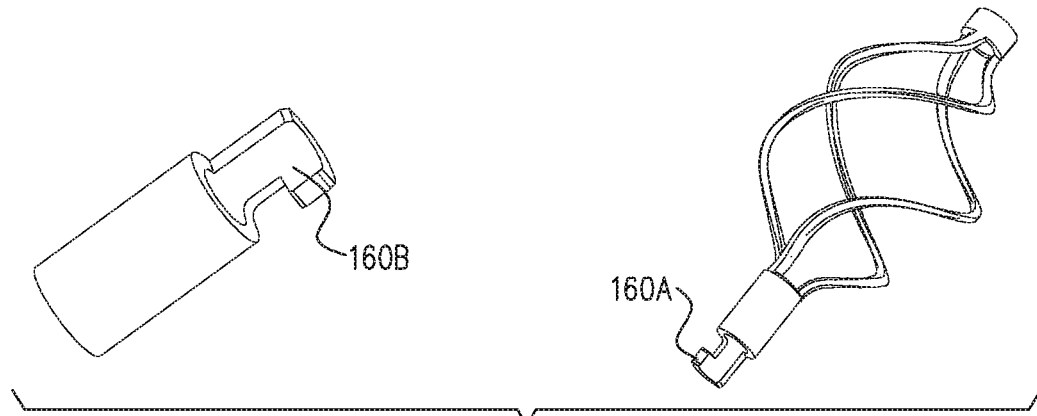
FIG. 25A is a schematic illustration of a first portion and a second portion of a coupling element configured to facilitate radial constriction (e.g., during crimping) of an impeller, in accordance with some applications of the present invention.

Reference is now made to FIG. 25A, which is a schematic illustration of first portion 160A and second portion 160B of a coupling element configured to facilitate radial constriction (e.g., during crimping) of an impeller (e.g., impeller 50 described hereinabove) independently of other components of a ventricular assist device, in accordance with some applications of the present invention. First and second portions 160A and 160B are configured to become engaged with each other. The first portion is disposed on the impeller, and the second portion is disposed on frame 34, e.g., on distal bearing 118 of frame 34. It is noted that only certain portions of the impeller are show in FIG. 25A, for illustrative purposes.

Figure 25B:
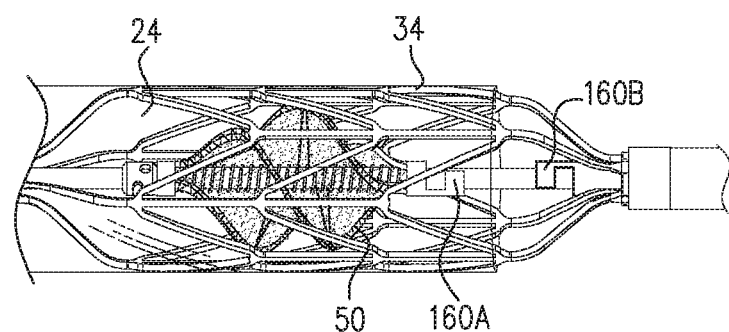
FIGS. 25B and 25C are schematic illustrations of respective stages of the crimping of the impeller, in accordance with some applications of the present invention.
Figure 25C:
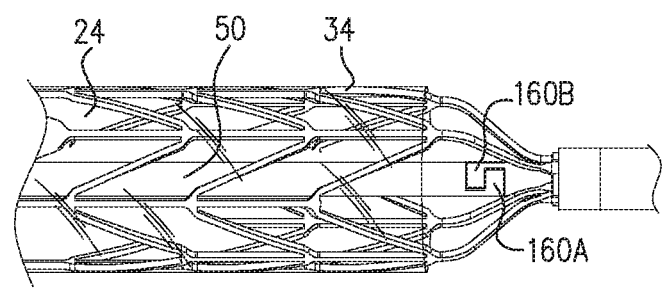

Reference is also made to FIGS. 25B and 25C, which are schematic illustrations of respective stages of the crimping of the impeller, in accordance with some applications of the present invention. For some applications, prior to crimping an outer portion of the ventricular assist device (e.g., frame 34 of left ventricular assist device 20, as shown), the impeller is radially constricted, by engaging portions 160A and 160B with each other and axially elongating the impeller, such as to radially constrict the impeller. Subsequently, the outer portion of the left ventricular assist device is radially constricted. For some applications, crimping the impeller in this manner reduces a likelihood of the impeller becoming damaged during the crimping of the outer portion of the left ventricular assist device. Subsequently, when the impeller and the frame are disposed in the subject's left ventricle, the first and second portions of the coupling element are decoupled from each other, such that the impeller is able to move with respect to frame 34.

Alternatively or additionally to the crimping technique shown in FIGS. 25A-C, the impeller is configured to become crimped by virtue of only one of the ends of the impeller (e.g., the proximal end of the impeller) being coupled to the axial shaft, and the other end (e.g., the distal end) being slidable with respect to the axial shaft, as described hereinabove. The impeller becomes crimped by the other end of the impeller sliding along the shaft, such that the impeller becomes axially elongated.

Figure 26:
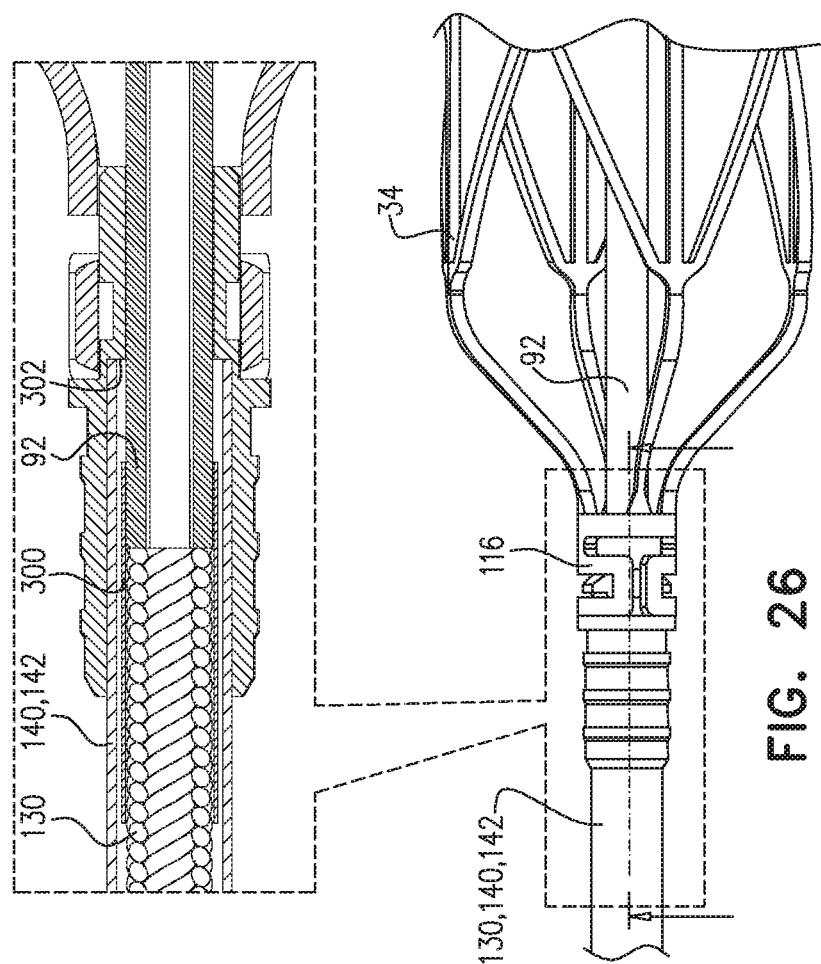
FIG. 26 is a schematic illustration of a stopper configured to prevent distal advancement of an impeller of a ventricular assist device during withdrawal of the ventricular assist device from the subject's body, in accordance with some applications of the present invention.

Reference is now made to FIG. 26, which is a schematic illustration of a stopper 300 configured to prevent distal advancement of impeller 50 of ventricular assist device 20 during withdrawal of the ventricular assist device from the subject's body, in accordance with some applications of the present invention. As described hereinabove, typically, in order to withdraw the ventricular assist device from the subject's body, delivery catheter 143 is advanced distally over frame 34 and impeller 50, in order to cause the frame and the impeller to assume their radially-constrained configurations. In some cases, there is a risk that, as the impeller is pushed distally by the delivery catheter, drive cable 130 may snap. For some applications, in the event that the drive cable snaps, then distal advancement of the proximal end of the impeller causes stopper 300 to engage with a shoulder 302, thereby preventing further advancement of the proximal end of the impeller. It is noted that the stopper is configured such that, during regular operation of the ventricular assist device (and throughout the axial back-and-forth motion cycle described hereinabove), the stopper does not engage with shoulder 302.

For some applications (not shown), a plurality of electrodes are disposed upon a distal portion of a left-ventricular assist device. Computer processor 25 (FIG. 1A) applies a current between the most distal electrode, which is typically configured to be disposed near the apex of the heart, and the most proximal electrode, which is typically configured to be disposed above the aortic valve. Conductance of that current between each pair of the electrodes is then measured by the computer processor. For some applications, the application of the current, and the conductance measurements, are performed using generally similar techniques to those described in an article entitled "The Conductance Volume Catheter Technique for Measurement of Left Ventricular Volume in Young Piglets," by Cassidy et al. (Pediatric Research, Vol. 31, No. 1, 1992, pp. 85-90). For some applications, the computer processor is configured to derive the subject's real-time left-ventricular pressure-volume loop based upon the conductance measurements. For some applications, the computer processor controls a rate of rotation of the impeller responsively to the derived pressure-volume loop.

With regards to all aspects of ventricular assist device 20 described with reference to FIGS. 1A-26, it is noted that, although FIGS. 1A and 1B show ventricular assist device 20 in the subject's left ventricle, for some applications, device 20 is placed inside the subject's right ventricle, such that the device traverses the subject's pulmonary valve, and techniques described herein are applied, mutatis mutandis. For some applications, components of device 20 are applicable to different types of blood pumps. For example, aspects of the present invention may be applicable to a pump that is used to pump blood from the vena cava and/or the right atrium into the right ventricle, from the vena cava and/or the right atrium into the pulmonary artery, and/or from the renal veins into the vena cava. Such aspects may include features of impeller 50, features of pump portion 27, drive cable 130, apparatus and methods for measuring blood pressure, etc. Alternatively or additionally, device 20 and/or a portion thereof (e.g., impeller 50, even in the absence of tube 24) is placed inside a different portion of the subject's body, in order to assist with the pumping of blood from that portion. For example, device 20 and/or a portion thereof (e.g., impeller 50, even in the absence of tube 24) may be placed in a blood vessel and may be used to pump blood through the blood vessel. For some applications, device 20 and/or a portion thereof (e.g., impeller 50, even in the absence of tube 24) is configured to be placed within the subclavian vein or jugular vein, at junctions of the vein with a lymph duct, and is used to increase flow of lymphatic fluid from the lymph duct into the vein, mutatis mutandis. Since the scope of the present invention includes using the apparatus and methods described herein in anatomical locations other than the left ventricle and the aorta, the ventricular assist device and/or portions thereof are sometimes referred to herein (in the specification and the claims) as a blood pump.

Figure 27A:
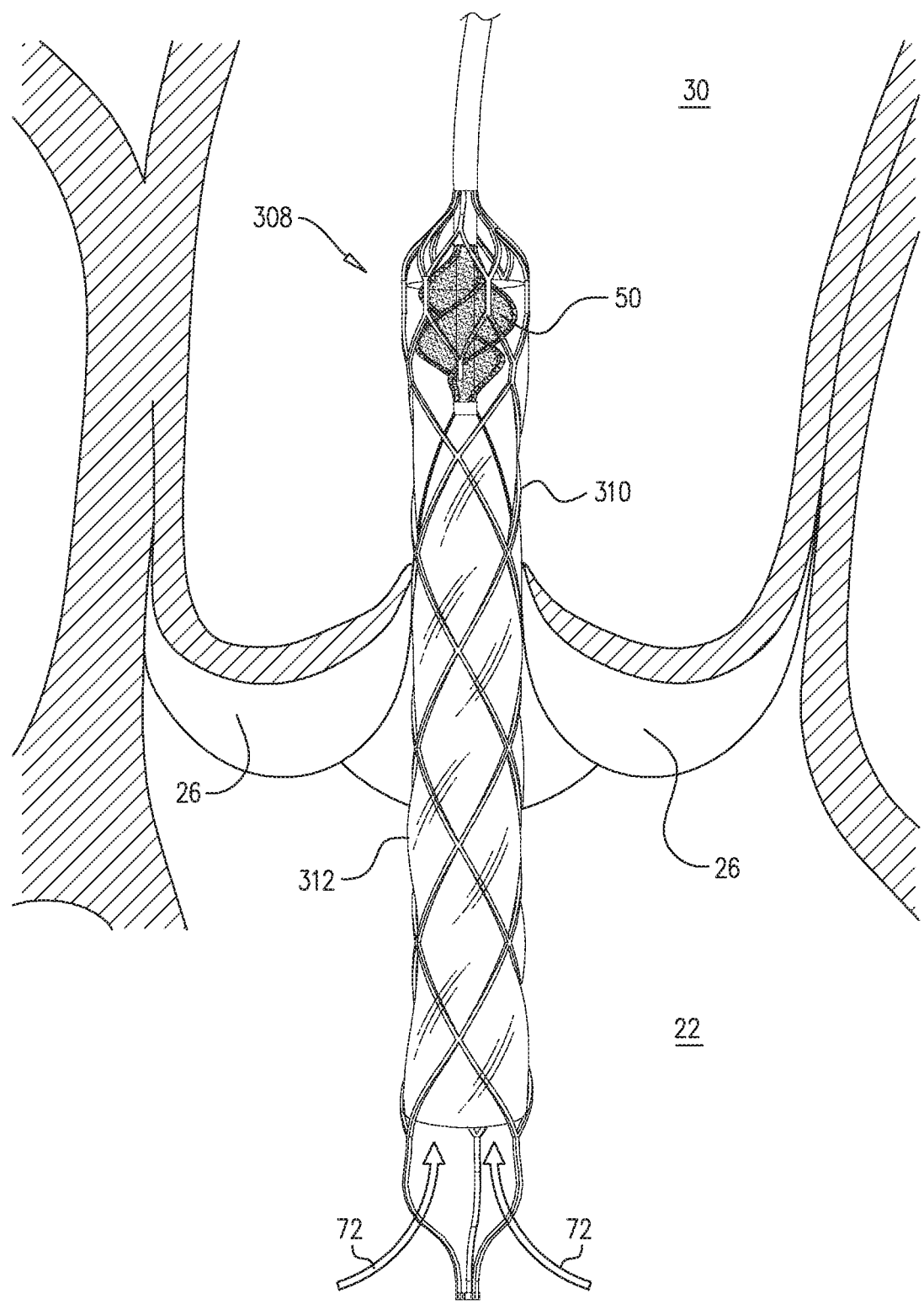
FIGS. 27A and 27B are schematic illustrations of a ventricular assist device, the device including a valve to prevent backflow of blood, for example, in the event that an impeller of the ventricular assist device malfunctions, in accordance with some applications of the present invention.
Figure 27B:
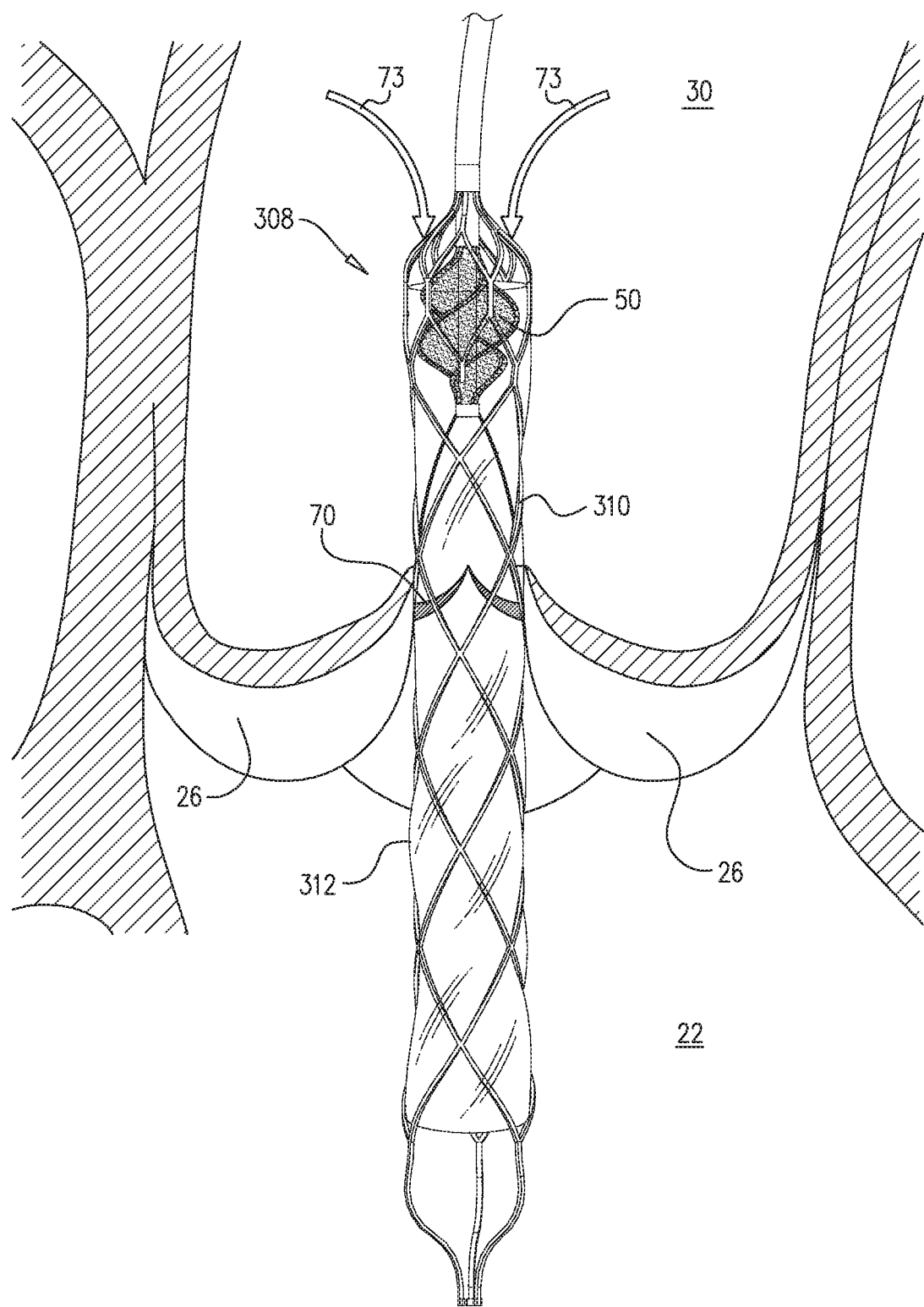

Reference is now made to FIGS. 27A and 27B, which are schematic illustrations of a ventricular assist device 308, the device including a valve 70 to prevent backflow of blood, for example, in the event that impeller 50 of the ventricular assist device malfunctions, in accordance with some applications of the present invention. Unlike ventricular assist device 20 described hereinabove with reference to FIGS. 1A-26, ventricular assist device 308 includes an impeller disposed within the aorta, and not in the left ventricle (e.g., as described in WO 18/078615 to Tuval, which is incorporated herein by reference). For some applications, the impeller is configured in a generally similar manner to impeller 50 described hereinabove. The impeller is disposed at a proximal end of a tube 312 (e.g., a polyester tube), which traverses the aortic valve, and a frame 310 supports the tube in an open configuration. FIG. 27A shows the ventricular assist device as configured when the impeller of the ventricular assist device is functioning normally, such that there is blood flow from left ventricle 22 to aorta 30, via tube 312 (which traverses aortic valve 26), the blood flow being indicated by arrows 72.

For some applications, tube 312 includes valve 70 at a region of the tube that is configured to be disposed distally with respect to impeller 50 and in the vicinity of the aortic valve, as shown in FIG. 27B. In the event that, for example, impeller 50 malfunctions, such that there is backflow of blood via tube 312 (as indicated by blood flow arrows 73 in FIG. 27B), leaflets of valve 70 are configured to close, such that there is substantially no retrograde blood flow from the aorta to the left ventricle. For some applications (not shown), tube 312 includes valve 70 at a proximal end of the tube, which is configured to be disposed in the aorta.

Figure 28A:
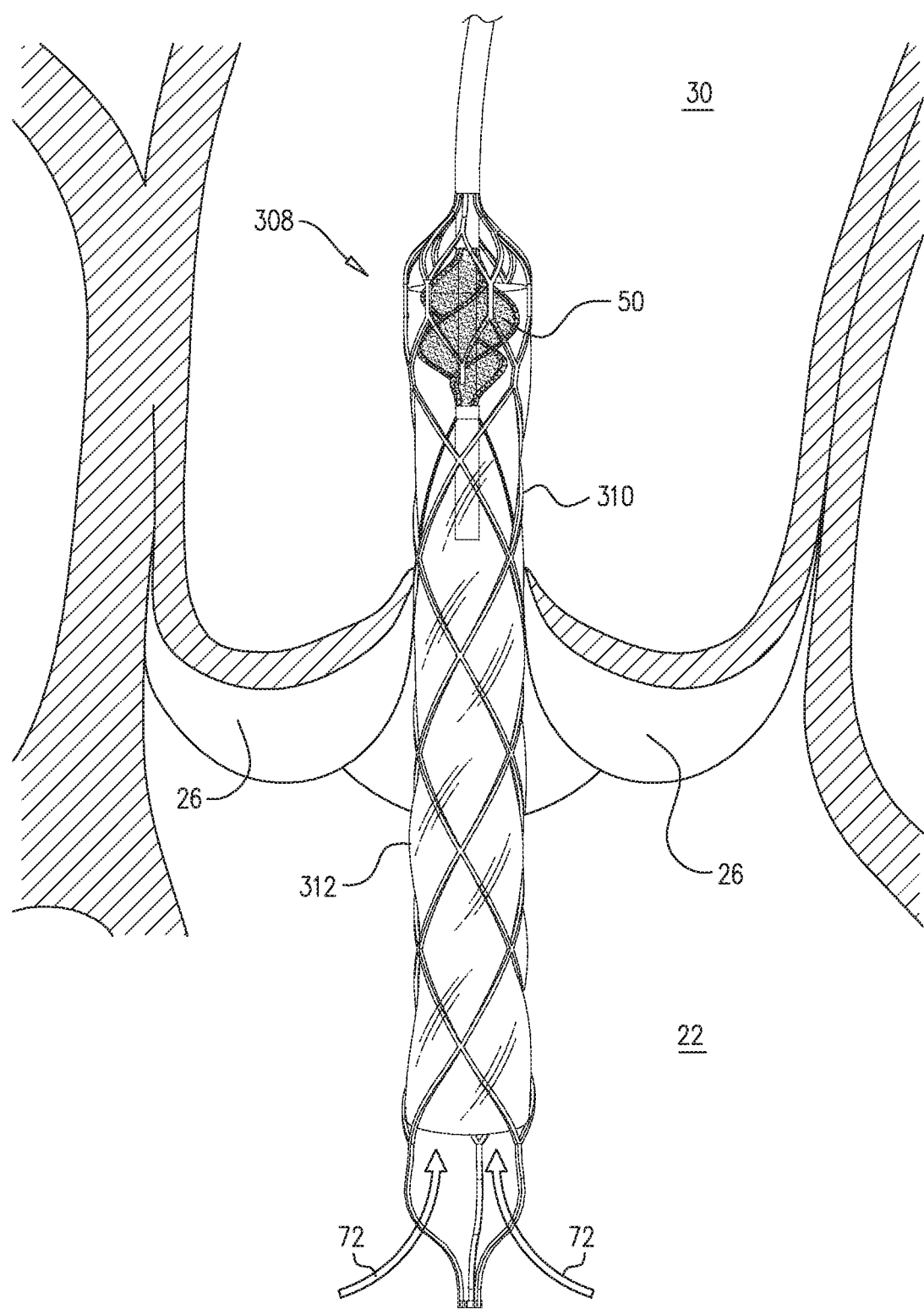
FIGS. 28A, 28B, and 28C are schematic illustrations of a ventricular assist device, the device including a safety balloon to prevent backflow of blood, for example, in the event that an impeller of the ventricular assist device malfunctions, in accordance with some applications of the present invention.
Figure 28B:
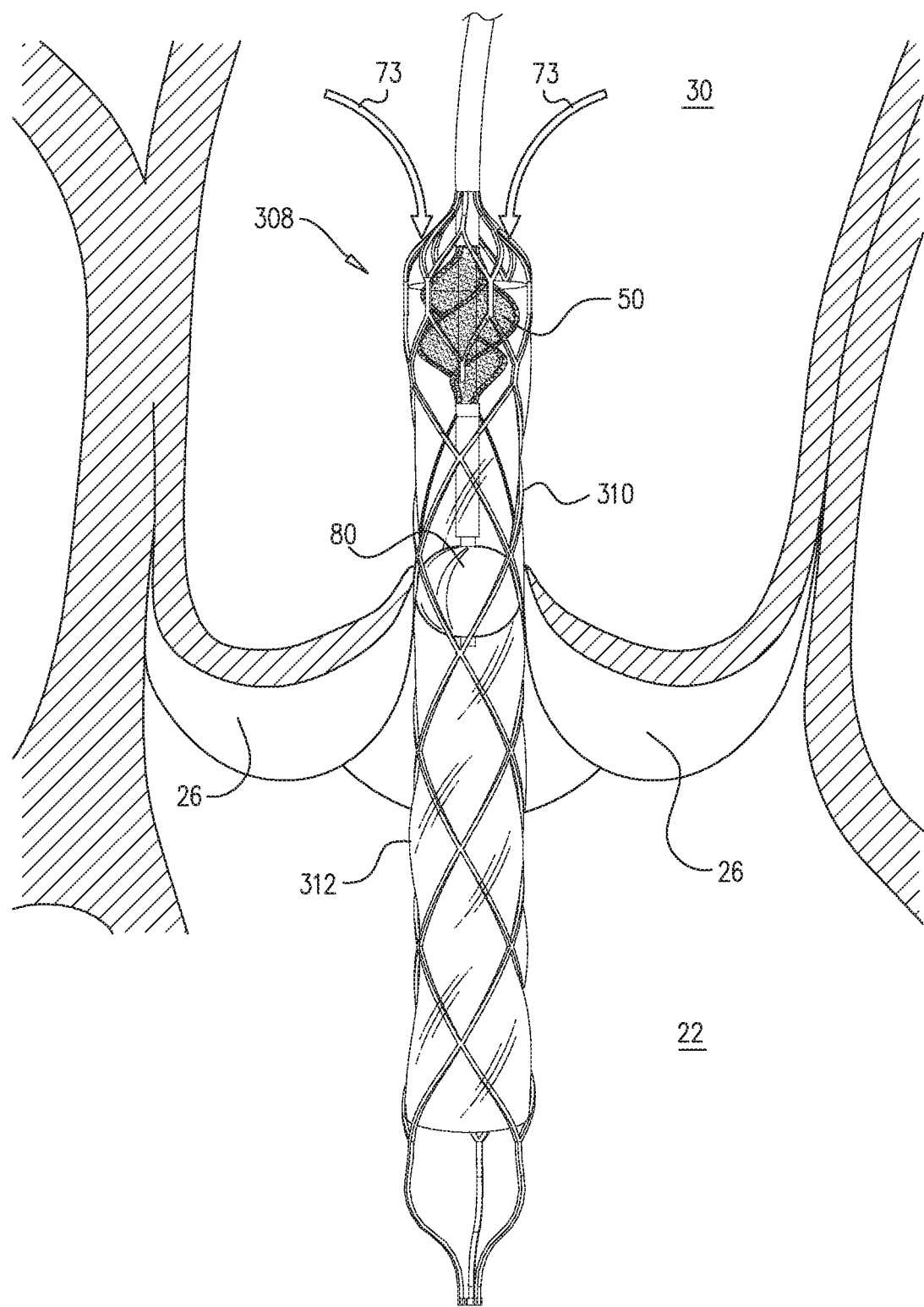
Figure 28C:
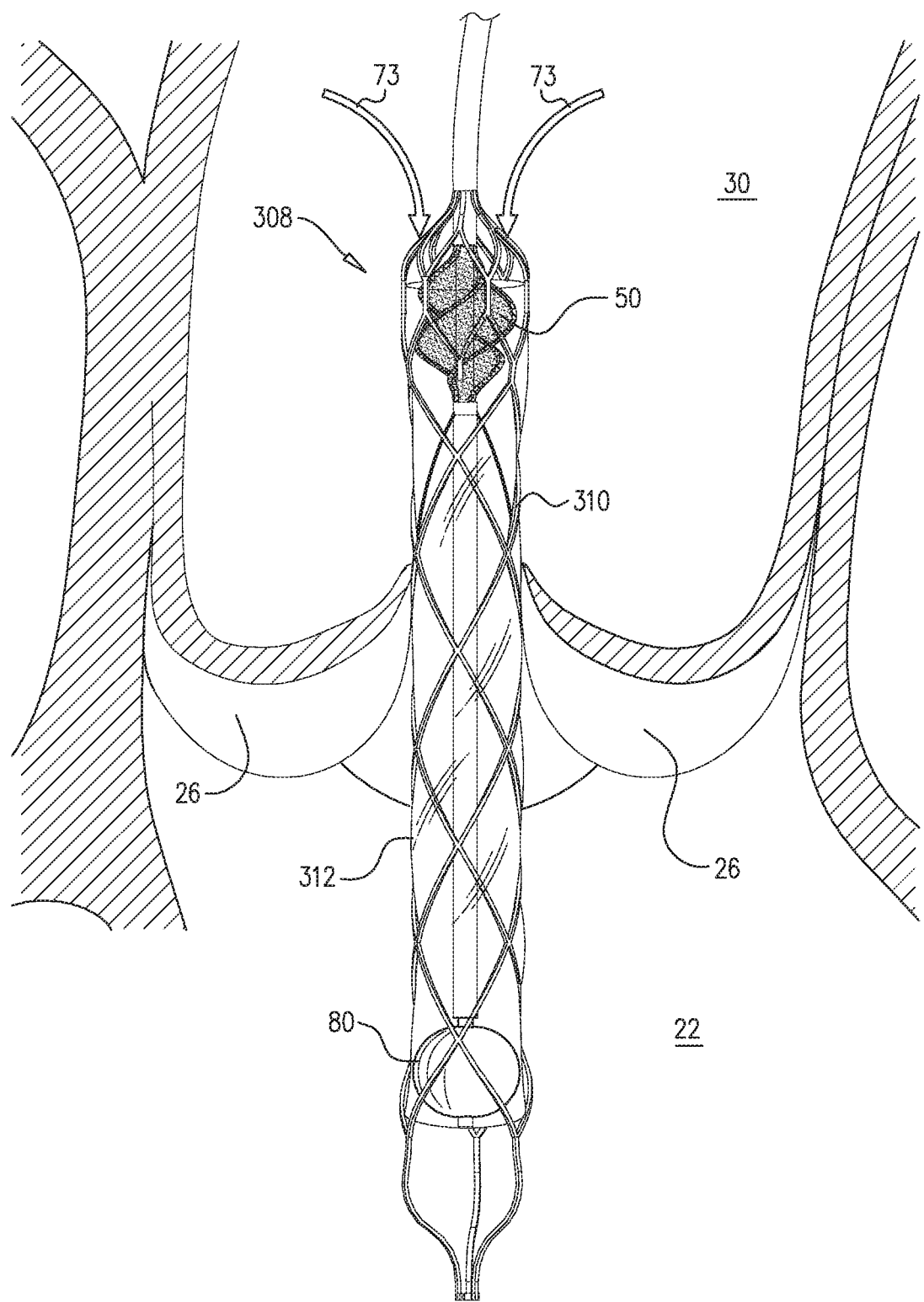

Reference is now made to FIGS. 28A, 28B, and 28C, which are schematic illustrations of ventricular assist device 308, the device including a safety balloon 80 to prevent backflow of blood, for example, in the event that the impeller of the ventricular assist device malfunctions, in accordance with some applications of the present invention. Unlike ventricular assist device 20 described hereinabove with reference to FIGS. 1A-26, ventricular assist device 308 includes an impeller disposed within the aorta, and not in the left ventricle (e.g., as described in WO 18/078615 to Tuval, which is incorporated herein by reference). For some applications, the impeller is configured in a generally similar manner to impeller 50 described hereinabove. The impeller is disposed at a proximal end of tube 312 (e.g., a polyester tube), which traverses the aortic valve, and frame 310 supports the tube in an open configuration. FIG. 28A shows the ventricular assist device as configured when the impeller of the ventricular assist device is functioning normally, such that there is blood flow from left ventricle 22 to aorta 30, via tube 312 (which traverses aortic valve 26), the blood flow being indicated by arrows 72. For some applications, ventricular assist device 308 includes balloon 80 at a region of the tube that is configured to be disposed distally with respect to impeller 50 and in the vicinity of the aortic valve, as shown in FIG. 28B. In the event that, for example, impeller 50 malfunctions, such that there is backflow of blood via tube 312 (as indicated by blood flow arrows 73 in FIG. 28B), computer processor 25 is configured to inflate the balloon, such that tube 312 becomes occluded and there is substantially no retrograde blood flow from the aorta to the left ventricle.

For some applications, ventricular assist device 308 includes balloon 80 at the distal end of tube 312, which is configured to be disposed in the left ventricle, as shown in FIG. 28C. In the event that, for example, impeller 50 malfunctions, such that there is backflow of blood via tube 312 (as indicated by blood flow arrows 73 in FIG. 28C), computer processor 25 is configured to inflate the balloon, such that tube 312 becomes occluded and there is substantially no retrograde blood flow from the aorta to the left ventricle.

The scope of the present invention includes combining any of the apparatus and methods described herein with any of the apparatus and methods described in one or more of the following applications, all of which are incorporated herein by reference:

International Patent Application PCT/IL2017/051273 to Tuval (published as WO 18/096531), filed Nov. 21, 2017, entitled "Blood pumps," which claims priority from U.S. Provisional Patent Application 62/425,814 to Tuval, filed Nov. 23, 2016;

International Application No. PCT/IL2017/051158 to Tuval (published as WO 18/078615), entitled "Ventricular assist device," filed Oct. 23, 2017, which claims priority from U.S. 62/412,631 to Tuval filed Oct. 25, 2016, and U.S. 62/543,540 to Tuval, filed Aug. 10, 2017;

International Patent Application PCT/IL2017/051092 to Tuval (published as WO 18-061002), filed Sep. 28, 2017, entitled "Blood vessel tube," which claims priority from U.S. Provisional Patent Application 62/401,403 to Tuval, filed Sep. 29, 2016;

US 2018/0169313 to Schwammenthal, which is the US national phase of International Patent Application PCT/IL2016/050525 to Schwammenthal (published as WO 16/185473), filed May 18, 2016, entitled "Blood pump," which claims priority from US Provisional Patent Application 62/162,881 to Schwammenthal, filed May 18, 2015, entitled "Blood pump;"

US 2017/0100527 to Schwammenthal, which is the US national phase of International Patent Application PCT/IL2015/050532 to Schwammenthal (published as WO 15/177793), filed May 19, 2015, entitled "Blood pump," which claims priority from US Provisional Patent Application 62/000,192 to Schwammenthal, filed May 19, 2014, entitled "Blood pump;"

U.S. Pat. No. 10,039,874 to Schwammenthal, which is the US national phase of International Patent Application PCT/IL2014/050289 to Schwammenthal (published as WO 14/141284), filed Mar. 13, 2014, entitled "Renal pump," which claims priority from (a) US Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. Pat. No. 9,764,113 to Tuval, issued Sep. 19, 2017, entitled "Curved catheter," which claims priority from U.S. Provisional Patent Application 61/914,470 to Tuval, filed Dec. 11, 2013, entitled "Curved catheter;" and U.S. Pat. No. 9,597,205 to Tuval, which is the US national phase of International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus comprising:
a ventricular assist device comprising:
an impeller configured to be placed inside a left ventricle of a subject;
a frame configured to be disposed around the impeller; and
a motor configured to drive the impeller to pump blood from the left ventricle to an aorta of the subject, by rotating the impeller,
the entire impeller being configured to undergo axial back-and-forth motion with respect to the frame, in response to cyclical changes in a pressure difference between the left ventricle and the aorta, wherein:
the impeller comprises proximal and distal bushings;
the ventricular assist device comprises proximal and distal radial bearings; and
the ventricular assist device further comprises an axial shaft configured to pass through the proximal and distal radial bearings and the proximal and distal bushings of the impeller, the axial shaft:
being coupled to at least one of the proximal and distal bushings of the impeller, such that the at least one bushing is held in an axially-fixed position with respect to the axial shaft, and
not being held in an axially-fixed position with respect to the proximal and distal radial bearings.

2. An apparatus comprising:
a ventricular assist device comprising:
an impeller configured to be placed inside a left ventricle of a subject;
a frame configured to be disposed around the impeller; and
a motor configured to drive the impeller to pump blood from the left ventricle to an aorta of the subject, by rotating the impeller,
the entire impeller being configured to undergo axial back-and-forth motion with respect to the frame, in response to cyclical changes in a pressure difference between the left ventricle and the aorta,
wherein the ventricular assist device does not include any thrust bearing configured to be disposed within a body of the subject.

3. An apparatus comprising:
a ventricular assist device comprising:
an impeller configured to be placed inside a left ventricle of a subject;
a frame configured to be disposed around the impeller; and
a motor configured to drive the impeller to pump blood from the left ventricle to an aorta of the subject, by rotating the impeller,
the entire impeller being configured to undergo axial back-and-forth motion with respect to the frame, in response to cyclical changes in a pressure difference between the left ventricle and the aorta, wherein the ventricular assist device further comprises one or more thrust bearings configured to be disposed outside a body of the subject, and wherein opposition to thrust generated by the rotation of the impeller is provided solely by the one or more thrust bearings disposed outside the subject's body.

4. An apparatus comprising:
a ventricular assist device comprising:
an impeller configured to be placed inside a left ventricle of a subject;
a frame configured to be disposed around the impeller; and
a motor configured to drive the impeller to pump blood from the left ventricle to an aorta of the subject, by rotating the impeller,
the entire impeller being configured to undergo axial back-and-forth motion with respect to the frame, in response to cyclical changes in a pressure difference between the left ventricle and the aorta, wherein:
the motor is configured to drive the impeller to pump blood from the subject's left ventricle to the subject's aorta, by rotating the impeller in a given direction of rotation; and
the ventricular assist device further comprises:
an axial shaft, the impeller being disposed on the axial shaft; and
a drive cable configured to extend from outside a body of the subject to the axial shaft, the drive cable being configured to impart rotational motion from the motor to the impeller by rotating, at least a portion of the drive cable comprising a plurality of wires disposed in a coiled configuration that is such that, in response to the drive cable rotating in the given direction of rotation, the plurality of wires disposed in the coiled configuration at least partially unwind, such that the portion of the drive cable shortens axially.

5. An apparatus comprising:
a ventricular assist device comprising:
an impeller configured to be placed inside a left ventricle of a subject;
a frame configured to be disposed around the impeller, the entire impeller being configured to undergo axial back-and-forth motion with respect to the frame, in response to cyclical changes in a pressure difference between the left ventricle and the aorta;
a motor configured to drive the impeller to pump blood from the left ventricle to an aorta of the subject, by rotating the impeller,
a sensor configured to detect an indication of axial motion of the impeller, and to generate a sensor signal in response thereto; and
a computer processor configured to receive the sensor signal and to generate an output in response thereto.

6. The apparatus according to claim 5, wherein the computer processor is configured to generate an output indicating a cardiac cycle of the subject, in response to receiving the sensor signal.

7. The apparatus according to claim 5, wherein the computer processor is configured to determine left-ventricular pressure of the subject, at least partially based upon the sensor signal.

8. The apparatus according to claim 5, wherein the computer processor is configured to change a rate of rotation of the impeller, at least partially based upon the sensor signal.

9. The apparatus according to claim 8, wherein the computer processor is configured:
to determine left-ventricular pressure of the subject, at least partially based upon the sensor signal, and
to change a rate of rotation of the impeller, at least partially based upon the determined left-ventricular pressure.

10. The apparatus according to claim 9, wherein the computer processor is configured to reduce the rate of rotation of the impeller, in response to determining that the subject's left-ventricular pressure has decreased.

11. An apparatus comprising:
a ventricular assist device comprising:
an impeller configured to be placed inside a left ventricle of a subject;
a frame configured to be disposed around the impeller, the entire impeller being configured to undergo axial back-and-forth motion with respect to the frame, in response to cyclical changes in a pressure difference between the left ventricle and the aorta;
a motor configured to drive the impeller to pump blood from the left ventricle to an aorta of the subject, by rotating the impeller,
a magnet, the impeller being coupled to the magnet such that axial motion of the impeller causes the magnet to undergo axial motion;
a sensor configured to detect magnetic flux generated by the magnet, and to generate a sensor signal in response thereto; and
a computer processor configured to receive the sensor signal and to generate an output in response thereto.

12. The apparatus according to claim 11, wherein the computer processor is configured to generate an output indicating a cardiac cycle of the subject, in response to receiving the sensor signal.

13. The apparatus according to claim 11, wherein the computer processor is configured to determine left-ventricular pressure of the subject, at least partially based upon the sensor signal.

14. The apparatus according to claim 11, wherein the computer processor is configured to change a rate of rotation of the impeller, at least partially based upon the sensor signal.

15. The apparatus according to claim 14, wherein the computer processor is configured:
to determine left-ventricular pressure of the subject, at least partially based upon the sensor signal, and
to change a rate of rotation of the impeller, at least partially based upon the determined left-ventricular pressure.

16. The apparatus according to claim 15, wherein the computer processor is configured to reduce the rate of rotation of the impeller, in response to determining that the subject's left-ventricular pressure has decreased.

17. An apparatus comprising:
a ventricular assist device comprising:
an impeller configured to be placed inside a left ventricle of a subject;
a frame configured to be disposed around the impeller; and
a motor configured to drive the impeller to pump blood from the left ventricle to an aorta of the subject, by rotating the impeller,
the entire impeller being configured to undergo axial back-and-forth motion with respect to the frame, in response to cyclical changes in a pressure difference between the left ventricle and the aorta, wherein:

the impeller comprises proximal and distal bushings;
the ventricular assist device comprises proximal and distal radial bearings;
the ventricular assist device further comprises an axial shaft configured to pass through the proximal and distal radial bearings and the proximal and distal bushings of the impeller;
the impeller is coupled to the axial shaft such that the impeller causes the axial shaft to undergo axial back-and-forth motion with respect to the proximal and distal radial bearings.

18. The apparatus according to claim 17, wherein the axial shaft is configured to clean interfaces between the axial shaft and the proximal and distal radial bearings, by undergoing the axial back-and-forth motion with respect to the proximal and distal radial bearings.

19. The apparatus according to claim 17, wherein the axial shaft is configured to reduce a build-up of heat at interfaces between the axial shaft and the proximal and distal radial bearings, by undergoing the axial back-and-forth motion with respect to the proximal and distal radial bearings, relative to if the axial shaft did not undergo the axial back-and-forth motion with respect to the proximal and distal radial bearings.

20. A method comprising:
placing an impeller of a ventricular assist device inside a left ventricle of a subject, with a frame disposed around the impeller; and
driving the impeller to pump blood from the left ventricle to an aorta of the subject, by rotating the impeller,
placement of the impeller inside the left ventricle being such that the entire impeller is allowed to undergo axial motion with respect to the frame, in response to cyclical changes in a pressure difference between the left ventricle and the aorta.

21. The method according to claim 20, wherein placing the impeller inside the subject's left ventricle comprises placing the impeller inside the subject's left ventricle in an absence of any thrust bearings of the ventricular assist device being placed within the body of the subject.

22. The method according to claim 20, further comprising providing opposition to thrust generated by the rotation of the impeller solely by using the one or more thrust bearings disposed outside a body of the subject.

23. The method according to claim 20, further comprising:
using a sensor, detecting an indication of axial motion of the impeller; and
generating an output in response to a sensor signal generated in response to the detected indication.

24. The method according to claim 20, wherein a magnet is coupled to the impeller such that axial motion of the impeller causes the magnet to undergo axial motion, and wherein the method further comprises:
using a sensor, detecting a magnetic flux generated by the magnet; and
generating an output in response to a sensor signal generated in response to the detected magnetic flux.

25. The method according to claim 24, wherein generating the output comprises generating an output indicating a cardiac cycle of the subject, in response to the detected magnetic flux.

26. The method according to claim 24, wherein generating the output comprises determining left-ventricular pressure of the subject, in response to the detected magnetic flux.

27. The method according to claim 24, wherein generating the output comprises changing a rate of rotation of the impeller, in response to the detected magnetic flux.

28. The method according to claim 27, wherein generating the output comprises:
determining left-ventricular pressure of the subject, in response to the detected magnetic flux, and
changing a rate of rotation of the impeller, at least partially based upon the determined left-ventricular pressure.

29. The apparatus according to claim 28, wherein changing the rate of rotation of the impeller, at least partially based upon the determined left-ventricular pressure comprises reducing the rate of rotation of the impeller, in response to determining that the subject's left-ventricular pressure has decreased.

30. The method according to claim 20, wherein the ventricular assist device includes proximal and distal radial bearings, and the impeller is disposed on an axial shaft that passes through the proximal and distal radial bearings, and wherein placing the impeller inside the subject's left ventricle comprises placing the impeller inside the subject's left ventricle such that the impeller causes the axial shaft to undergo axial back-and-forth motion with respect to the proximal and distal radial bearings, in response to cyclical changes in a pressure difference between the left ventricle and the aorta.

31. The method according to claim 30, wherein placing the impeller inside the subject's left ventricle such that the impeller causes the axial shaft to undergo axial back-and-forth motion with respect to the proximal and distal radial bearings comprises cleaning interfaces between the axial shaft and the proximal and distal radial bearings, by the axial shaft undergoing the axial back-and-forth motion with respect to the proximal and distal radial bearings.

32. The method according to claim 30, wherein placing the impeller inside the subject's left ventricle such that the impeller causes the axial shaft to undergo axial back-and-forth motion with respect to the proximal and distal radial bearings comprises reducing a build-up of heat at interfaces between the axial shaft and the proximal and distal radial bearings, by undergoing the axial back-and-forth motion with respect to the proximal and distal radial bearings, by the axial shaft undergoing the axial back-and-forth motion with respect to the proximal and distal radial bearings, relative to if the axial shaft did not undergo the axial back-and-forth motion with respect to the proximal and distal radial bearings.

* * * * *